(12) United States Patent
Chancellor et al.

(10) Patent No.: US 8,110,217 B2
(45) Date of Patent: *Feb. 7, 2012

(54) SPHINGOMYELIN LIPOSOMES FOR THE TREATMENT OF HYPERACTIVE BLADDER DISORDERS

(75) Inventors: Michael B. Chancellor, Pittsburgh, PA (US); Pradeep Tyagi, Pittsburgh, PA (US); Matthew O. Fraser, Apex, NC (US); Yao-Chi Chuang, Kaohsiung Hsein (TW); William C de Groat, Pittsburgh, PA (US); Leaf Huang, Durham, NC (US); Naoki Yoshimura, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 1094 days.

This patent is subject to a terminal disclaimer.

(21) Appl. No.: 11/546,025

(22) Filed: Oct. 11, 2006

(65) Prior Publication Data

US 2007/0122466 A1    May 31, 2007

Related U.S. Application Data

(60) Continuation-in-part of application No. 11/438,912, filed on May 22, 2006, now abandoned, which is a division of application No. 10/218,797, filed on Aug. 13, 2002, now Pat. No. 7,063,860, application No. 11/546,025, which is a continuation-in-part of application No. 11/489,748, filed on Jul. 19, 2006, now abandoned.

(60) Provisional application No. 60/725,402, filed on Oct. 11, 2005, provisional application No. 60/311,868, filed on Aug. 13, 2001, provisional application No. 60/701,431, filed on Jul. 20, 2005.

(51) Int. Cl.
    *A61K 9/127*    (2006.01)

(52) U.S. Cl. .................................................. 424/450
(58) Field of Classification Search .............. 424/450, 424/434–435, 443, 45; 514/937, 943
See application file for complete search history.

(56) References Cited

U.S. PATENT DOCUMENTS 4,708,861 A    11/1987    Popescu et al.
(Continued)

FOREIGN PATENT DOCUMENTS
EP    0036277    9/1981

OTHER PUBLICATIONS

Kozubek et al in Acta Biochemica Polonica, vol. 47, # 3, pp. 639-649, 2000.*

(Continued)

*Primary Examiner* — Gollamudi Kishore
(74) *Attorney, Agent, or Firm* — Pabst Patent Group LLP

(57) ABSTRACT

The present invention provides pharmaceutical compositions and methods for the instillation of lipid vehicles comprised of liposomes containing sphingomyelin or sphingomyelin metabolites to prevent, manage, ameliorate and/or treat disorders involving neuropathic pain and aberrant muscle contractions, such as what occurs in bladder hyperactivity disorders such as interstitial cystitis (IC) in animals or humans in need thereof. Also provided is a liposome-based delivery of drugs, e.g., antibiotics, pain treatments and anticancer agents, to the bladder, genitourinary tract, gastrointestinal system, pulmonary system and other organs or body systems. In particular, liposome-based delivery of vanilloid compounds, such as resiniferatoxin, capsaicin, or tinyatoxin and toxins, such as botulinum toxin is provided for the treatment of bladder conditions, including pain, inflammation, incontinence and voiding dysfunction.

9 Claims, 13 Drawing Sheets

U.S. PATENT DOCUMENTS

| | | | |
|---|---|---|---|
| 4,932,936 | A | 6/1990 | Dykstra et al. |
| 5,298,019 | A | 3/1994 | Borodic |
| 5,698,549 | A | 12/1997 | Steers et al. |
| 5,763,399 | A | 6/1998 | Lee |
| 5,837,694 | A | 11/1998 | Barrett |
| 6,207,180 | B1 | 3/2001 | Ottoboni et al. |
| 6,239,180 | B1 | 5/2001 | Robbins |
| 6,239,267 | B1 | 5/2001 | Duckworth et al. |
| 6,271,211 | B1 | 8/2001 | Christ et al. |
| 6,365,164 | B1 | 4/2002 | Schmidt |
| 6,630,515 | B2 * | 10/2003 | Cruz et al. ............ 514/691 |
| 6,677,309 | B1 * | 1/2004 | Taatjes et al. ............ 514/35 |
| 7,063,860 | B2 | 6/2006 | Chancellor et al. |
| 2001/0018415 | A1 | 8/2001 | Aoki et al. |
| 2002/0115992 | A1 | 8/2002 | Utley et al. |
| 2003/0203030 | A1 | 10/2003 | Achton et al. |
| 2004/0241244 | A1 | 12/2004 | Lin et al. |
| 2007/0003610 | A1 | 1/2007 | Chancellor et al. |

OTHER PUBLICATIONS

De Paiva, A. et al., entitled "Light chain of botulinum neurotoxin is active in mammalian motor nerve terminals when delivered via liposomes", FEBS Lett., 277(1-2):pp. 171-174, 1990.

Paavola, A. et al., entitled "Controlled release injectable liposomal gel of ibuprofen for epidural analgesia", Int. J. Pharm., 199(1):pp. 85-93, 2000.

Boogaerts, J.G et al., entitled "Epidural administration of liposome-associated bupivacaine for the management of postsurgical pain: A first study", J. Clin. Anesth., 6(4):pp. 315-320, 1994.

LaFont, N. D. et al., entitled "Use of liposome-associated bupivacaine in a cancer pain syndrome", Anaesthesia, 51(6):pp. 578-579, 1996.

Sharma, A. et al., entitled "Paclitaxel-liposomes for intracavitary therapy of intraperitoneal P388 leukemia", Cancer Letters, 107(2):pp. 265-272, 1996.

Fagerli, J. et al., entitled "Intravesical capsaicin for the treatment of interstitial cystitis: a pilot study", Canadian Journal of Urology, 6(2):pp. 737-744, Apr. 1999.

Lazzeri, M. et al., entitled "Intravesical capsaicin for treatment of severe bladder pain: a randomized placebo controlled study", J. Urol., 156(3):pp. 947-952, Sep. 1996.

Meddings, J.B. et al., entitled "Capsaicin effects on non-neuronal plasma membranes", Biochimica Biophysica Acta, 1070(1):pp. 43-50, 1991.

Tsuchiya, H., entitled "Biphasic membrane effects of capsaicin, an active component in *Capsicum* species", J. Ethnopharmacol., 75(2-3):pp. 295-299, 2001.

Johnson, J.W. et al., entitled "Binding of liposomes to human bladder tumor epithelial cell lines: implications for an intravesical drug delivery system for the treatment of bladder cancer", Selective Cancer Therapeutics, 5(4):pp. 147-155, 1989.

Kiyokawa, H. et al., entitled "Distribution of doxorubicin in the bladder wall and regional lymph nodes after bladder submucosal injection of liposomal doxorubicin in the dog", J. Urol., 161(2):665-667, 1999.

Barton, K.N. et al., entitled "Effects of urea and trimethylamine *N*-oxide on fluidity of liposomes and membranes of an elasmobranch", Am. J. Physiol., 276(2 Pt 2):pp. R397-R406, 1999.

Zhou, F. et al., entitled "Mucosal IgA response to rectally administered antigen formulated in IgA-coated liposomes", Vaccine, 13(7):pp. 637-644, 1995.

Egerdie, R.B. et al., entitled "The effect of liposome encapsulated antineoplastic agents on transitional cell carcinoma in tissue culture", J. Urol., 142(2 Pt 1):pp. 390-398, 1989.

Wright, E.M. et al., entitled "Thermodynamic analysis of nonelectrolyte permeation across the toad urinary bladder", J. Membr. Biol., 29(3):pp. 289-312, 1976.

Filion, M. C. et al., "Anti-inflammatory activity of cationic lipids", British J. Pharmacology, 122:pp. 551-559, 1997.

Kozubek et al., entitled "Liposomal drug delivery, a novel approach: PLARosomes", Acta Biochimica Polonica, 47(3):pp. 639-646, 2000.

Duque et al., AACR meeting, Abstract No. 2177, 1993.

Yamamota, Y. et al., entitled "Inhibition of CD62L+T-cell response in vitro via a novel sulfo-glycolipid, β-SQAG9 liposome that binds to CD62L molecule on the cell surface", Cellular Immunology, 232:pp. 105-115, 2004.

* cited by examiner

SPHINGOMYELIN LIPOSOMES FOR THE TREATMENT OF HYPERACTIVE BLADDER DISORDERS

CROSS-REFERENCE TO RELATED APPLICATIONS

This application claims the benefit of U.S. Provisional Application No. 60/725,402, filed Oct. 11, 2005. This application is also a Continuation-in-Part of U.S. application Ser. No. 11/438,912, filed May 22, 2006 now abandoned, which is a Divisional of U.S. Ser. No. 10/218,797, filed Aug. 13, 2002, now U.S. Pat. No. 7,063,860, which claims the benefit of U.S. Provisional Application No. 60/311,868 filed Aug. 13, 2001. This application is also a Continuation-in-Part of U.S. application Ser. No. 11/489,748, filed Jul. 19, 2006 now abandoned, which claims the benefit of U.S. Provisional Application No. 60/701,431 filed Jul. 20, 2005, all of which are incorporated herein by reference.

BACKGROUND OF THE INVENTION

1. Field of the Invention

The present invention relates to compositions and methods for the instillation of lipid vehicles comprised of liposomes for the treatment of various disorders, including bladder inflammation and dysfunction. The liposomes of the present invention are used alone or as lipid vehicles for prolonged delivery of drugs such as antibiotics and anticancer agents to the bladder, genitourinary tract, gastrointestinal system, pulmonary system, and other organs or body systems. Specifically, the present invention relates to pharmaceutical compositions comprised of liposomes containing lipids having a phosphaditylcholine (PC) head group, and preferably is sphingomyelin or sphingomyelin metabolites, for preventing, managing, ameliorating and/or treating hyperactive bladder disorders such as interstitial cystitis. The present invention also relates to liposome-based delivery of resiniferatoxin, capsaicin, tinyatoxin, and other vanilloid compounds for the treatment of bladder pain, inflammation, incontinence, and voiding dysfunction. Also related is liposome-based delivery of toxins, such as botulinum toxin, for the treatment of involuntary muscle contractions including those associated with urethral dyssynergia and bladder spasticity.

2. Description of Related Art

Neuropathic pain is thought to occur because of a sensitization in the peripheral and central nervous systems after an initial injury to the peripheral nervous system. Direct injury to the peripheral nerves as well as many systemic diseases, such as HIV/AIDS, herpes zoster, syphilis, diabetes and various autoimmune diseases, can induce neuropathic pain. Such pain also is associated with conditions of the bladder, including interstitial cystitis. Neuropathic pain typically is experienced as burning, shooting and unrelenting in its intensity, and sometimes can be more debilitating than the initial injury or disease process from which it was induced. For example, a person afflicted with interstitial cystitis typically urinates about sixteen times a day, although it is not unusual for urination frequency to occur up to forty times in one day. Unfortunately, the few remedies that have been reported to alleviate this condition are effective in only a small percentage of patients.

Interstitial cystitis (IC) is an incurable, chronic, debilitating disease of the urinary bladder that is characterized by bladder pain, chronic pelvic pain, irritative voiding symptoms and sterile urine. In IC, the bladder wall typically shows inflammatory infiltration with mucosal ulceration and scarring which causes smooth muscle contraction, diminished urinary capacity, hematuria and frequent, painful urination.

Although IC once was thought to be rare, the U.S. National Institutes of Health currently estimate the prevalence of IC to range between 700,000 to one million people in the United States. Ninety percent of clinical cases of IC occur in women, but this percentage could be inflated because many men currently diagnosed with non-bacterial prostatitis may actually be suffering from IC. Additionally, the pelvic pain associated with IC often is misdiagnosed initially, resulting in patients being treated with antibiotics for a urinary tract bacterial infection with no relief. Urine cultures subsequently rule out a bacterial infection and, ultimately, IC is diagnosed by cystoscopy/hydrodistention.

The specific cause of IC is unknown. Etiological theories for IC currently being investigated include congenital defects of the bladder lining, an autoimmune syndrome, or neurogenic inflammation. Genetic studies have pointed to an inherited susceptibility to IC, although to date no specific gene has been implicated for IC.

Although the pathogenesis of IC is uncertain, it seems likely that a dysfunctional epithelium results in the transepithelial migration of solutes, such as potassium, which depolarizes sensory nerves and produces the above-described symptoms. Previous reports have shown that IC patients have defects in the glycosaminoglycan (GAG) layers of the uroepithelium (Parsons, C. L. et al., J. Urol., 73:504, 1994; Hohlbrugger, G., Br. J. Urol., 83(2):22, 1999). Therapies that restore the mucosal lining or surface GAG layer, such as, for example, administration of heparin, hyaluronic acid, or pentosanpolysulfate, have been shown to reduce the leakage of irritant(s) and result in palliation of IC symptoms.

Capsaicin is a homovanillic acid derivative (8-methyl-N-vanillyl-6-nonenamid). It is the active component of the red pepper of the genus *Capsicum*, and has been used in humans for topical treatment of cluster headache, herpes zoster, and vasomotor rhinitis (see P. Holzer, 1994, Pharmacol. Rev. 43:143; Sicuteri et al., 1988, Med. Sci. Res. 16:1079; Watson et al., 1988, Pain 33:333; Marabini et al., 1988, Regul. Pept. 22:1). In vitro capsaicin modulates cellular growth, collagenase synthesis, and prostaglandin secretion from rheumatoid arthritis synoviocytes (see Matucci-Cerinic et al., 1990, Ann. Rheum. Dis. 49:598). Capsaicin also has been shown to be immunomodulatory, as indicated by its ability to modulate lymphocyte proliferation, antibody production and neutrophil chemotaxis (see Nilsson et al., 1988, J. Immunopharmac. 10:747; Nilsson et al., 1991, J. Immunopharmac. 13:21; and Eglezos et al., 1990, J. Neuroimmunol. 26:131). These effects play an important role in the use of capsaicin for treatment of arthritis. In addition, capsaicin induces mitochondrial swelling, inhibits NADH oxidase, induces apoptosis of transformed cells, stimulates adenylate cyclase, activates protein kinase C, inhibits superoxide anion generation and alters the redox state of the cell.

The various effects of capsaicin are mediated through a specific cellular receptor referred to as a vanilloid receptor. This receptor is shared by resiniferatoxin, an alkaloid derived from plants of the genus *Euphorbia*. Resiniferatoxin is a structural homologue of capsaicin, and has been shown to mimic many of the actions of capsaicin. Resiniferatoxin also is structurally similar to phorbol esters (phorbol myristate acetate), which interact with distinct binding sites and activate protein kinase C (see Szallasi, et al., 1989, Neurosci. 30:515; and Szallasi and Blumberg, 1989, Neurosci. 30:515). Unlike resiniferatoxin, capsaicin has no homology to phorbol myristate acetate. However, capsaicin can activate protein kinase C, suggesting that such activation is not due entirely to the phorbol ester-like moiety on resiniferatoxin.

Capsaicin has been used as an experimental tool because of its selective action on small diameter afferent nerve fibers, or C fibers, which mediate pain. From studies in animals, capsaicin appears to trigger C fiber membrane depolarization by opening cation selective channels for calcium and sodium. Although detailed mechanisms of action are not yet known, capsaicin-mediated effects include: (i) activation of nociceptors in peripheral tissues; (ii) eventual desensitization of peripheral nociceptors to one or more stimulus modalities; (iii) cellular degeneration of sensitive unmyelinated C fiber afferents; (iv) activation of neuronal proteases; (v) blockage of axonal transport; and (vi) a decrease in the absolute number of C fibers without affecting the number of myelinated fibers.

Because of the ability of capsaicin to desensitize nociceptors in peripheral tissues, its potential analgesic effects have been assessed in various clinical trials. U.S. Pat. No. 5,431, 914 suggests that a topical preparation containing a concentration of capsaicin of about 0.01% to about 0.1% could be used to treat internal organ pathologies. U.S. Pat. No. 5,665, 378 discusses a transdermal therapeutic formulation comprising capsaicin, a non-steroidal anti-inflammatant, and pamadorm (a diuretic agent) where the composition is said to contain from about 0.001-5% by weight capsaicin and to be useful in treating the pain and discomfort associated with menstrual cramps, bloating, and/or muscular pain such as muscular back pain. Several studies have assessed intravesical capsaicin as a treatment for urge incontinence in patients with spinal detrusor hyperreflexia or bladder hypersensitivity disorders (see F. Cruz, 1998, Int. Urogynecol. J. Pelvic Floor Dysfunct. 9:214-220).

Capsaicin application frequently causes burning pain and hyperalgesia apart from the neuropathic pain being treated, and thus patient compliance has been poor and drop out rates during clinical trials have exceeded fifty percent. The spontaneous burning pain and heat hyperalgesia are believed to be due to intense activation and temporary sensitization of the peripheral nociceptors at the site of capsaicin application (primary hyperalgesia). Mechanical hyperalgesia evident in areas surrounding the site of topical application appears to originate from central sensitization of dorsal horn neurons involved in pain transmission (secondary hyperalgesia). Because of these side effects, the maximal capsaicin concentration used in previous human studies usually has been limited to 0.075%.

Dystonias are neurological movement disorders characterized by involuntary muscle contractions that force certain parts of the body into abnormal, sometimes painful, movements or postures (see S. B. Bressman, 2000, Clin. Neuropharmacol. 23(5):239-51). Dystonia disorders cause uncontrolled movement and prolonged muscle contraction, which can result in spasms, twisting body motions, tremor, or abnormal posture. These movements may involve the entire body or only an isolated area, such as the arms and legs, trunk, neck, eyelids, face, bladder sphincter, or vocal cords. Dystonias result from environmental or disease-related damage to the basal ganglia, birth injury, (particularly due to lack of oxygen), certain infections, reactions to certain drugs, heavy-metal or carbon monoxide poisoning, trauma, or stroke. Dystonias also can be symptomatic of other diseases, some of which may be hereditary.

Urinary detrusor-sphincter dyssynergia (UDSD; also called detrusor-external sphincter dyssynergia and urethral dyssynergia) is a specific type of neurological movement disorder (see H. Madersbacher, 1990, Paraplegia 28(4):217-29; J. T. Andersen et al., 1976, J. Urol. 116(4):493-5). UDSD is characterized by involuntary urinary sphincter spasms occurring simultaneously with bladder contractions. The lack of coordination between detrusor contraction and urethral relaxation causes urinary obstruction (i.e., partial or complete block of urination). As a result of UDSD, the bladder cannot empty completely. This creates a buildup of urinary pressure, which can lead to severe urinary tract damage and life-threatening consequences. UDSD results from lesions of the corticospinal tract, which are caused by spinal cord injury, multiple sclerosis, or related conditions.

Another neurological movement disorder is hyperactive (also called contracted; spastic) neurogenic bladder (see M. H. Beers and R. Berkow (eds), 1999, The Merck Manual of Diagnosis and Therapy, Section 17: Genitourinary Disorders, Chapter 216: Myoneurogenic Disorders). In hyperactive bladder, the bladder contracts more frequently than normal due to instability and inappropriate contraction of detrusor muscles (see, e.g., C. F. Jabs et al., 2001, Int. Urogynecol. J. Pelvic Floor Dysfunct. 12(1):58-68; S. K. Swami and P. Abrams, 1996, Urol. Clin. North Am. 23(3):417-25). Hyperactive bladders can empty spontaneously and result in urinary incontinence (urge incontinence). Additionally, the uncoordinated contraction between the bladder and bladder outlet (vesical neck or external urinary sphincter) can result in vesico-ureteral reflux with concomitant renal damage. Hyperactive bladder usually is due to brain or suprasacral spinal cord damage. The most common cause is spinal cord injury from transverse myelitis or traumatic cord transection. Hyperactive bladder also can be caused by conditions such as anxiety, aging, infections (e.g., syphilis), diabetes mellitus, brain and spinal cord tumors, stroke, ruptured intervertebral disk, and demyelinating and degenerative diseases (e.g., multiple sclerosis and amyotrophic lateral sclerosis).

Botulinum toxins are zinc endopeptidases produced by the anaerobic bacterium *Clostridium botulinum*. Previously known as a cause of a serious and often fatal paralysis acquired through ingestion of contaminated food, botulinum neurotoxins are presently used in both therapeutic and cosmetic applications (see N. Mahant et al., 2000, J. Clin. Neurosci. 7(5):389-94; A. Carruthers and J. Carruthers, 2001, Semin. Cutan. Med. Surg. 20(2):71-84). In particular, these toxins are used in the treatment of conditions involving involuntary muscle spasms, frown lines, and facial wrinkles.

There are seven known serotypes of botulinum toxins (designated A-G). The serotypes differ in their cellular targets, potency and duration of action, but all exert their paralytic effect by inhibiting acetylcholine release at the neuromuscular junction (see M. F. Brin, 1997, Muscle Nerve 20(suppl 6):S146-S168). Each serotype acts by cleaving one or more proteins involved in vesicle transport and membrane fusion. For example, botulinum toxin A is internalized by endocytosis at the axon terminal, where it is fully activated by disulfide reduction reactions, and it targets SNAP-25 (see M. F. Brin, 1997, Muscle Nerve 20(suppl 6):S146-S168). The extent of botulinum toxin-mediated paralysis depends on the dose, volume and serotype employed. Botulinum toxin A causes reversible denervation atrophy that is typically terminated by axon sprouting within 2 to 6 months (see M. F. Brin, 1997, Muscle Nerve 20 (suppl 6):S146-S168).

A major drawback of current botulinum toxin therapies is the development of antitoxin antibodies in patients. Antitoxin antibodies result in resistance to botulinum toxin and the reduction or elimination of its therapeutic effect. It has been estimated that the prevalence of neutralizing antibodies among patients receiving chronic treatment at the higher doses for torticollis or spasticity is probably at least 3% (see M. F. Brin, 1997, Muscle Nerve 20(suppl 6):S146 S168).

Patients with botulinum toxin A resistance may benefit from injections with other serotypes, including botulinum toxin B, C or F. However, differences in the duration of the effects of the other serotypes can be significant and cause dramatic reductions in treatment efficacy (see M. F. Brin, 1997, Muscle Nerve 20(suppl 6):S146-S168).

The use of liposomes as vehicles for drug delivery and gene therapy is well known. For example, previous studies have demonstrated that submucosal injection of liposomal doxorubicin into bladder wall provides an effective and safe treatment for bladder cancer with pelvic lymph node metastasis (Tsuruta I. et al., J. Urol., 157:1652, 1997). In a liposome-drug delivery system, an active ingredient, such as a drug, is encapsulated or entrapped in the liposome and then administered to the patient to be treated. Alternatively, if the active ingredient is lipophilic, it may be associated with the lipid bilayer. It is believed that liposomes interact with cells by stable absorption, endocytosis, lipid transfer and fusion (Egerdie, R. B. et al., J. Urol., 142:390, 1989). Liposomes have low antigenicity and appear to act as molecular films that fuse with cells. Thus, for example, liposomes can provide optimal conditions for wound healing (Reimer, K. et al., Dermatology, 195(2):S93).

Based on the pain and suffering associated with hyperactivity bladder disorders and, in particular, with IC, there exists a need to prevent, manage, ameliorate and/or treat those afflicted with such intractable disorders.

SUMMARY OF THE INVENTION

The present invention fulfills this need by providing improved treatments for pain (e.g., neuropathic pain), pain-intensive disorders (e.g., IC), muscle contraction disorders (e.g., IC, hyperactive bladder and UDSD) and related conditions by providing compositions and methods for the administration of lipid vehicles in an animal or human in need thereof. Lipid vehicles provide non-toxic vehicles for the delivery of lipophilic therapeutic agents that have irritative side effects (e.g., vanilloids such as capsaicin) or undesirable antigenicity (e.g., botulinum toxin). Advantageously, the disclosed lipid vehicles can be used simultaneously to deliver and to ameliorate irritation caused by irritating therapeutic agents. The lipid vehicles also can be used to reduce or prevent antibody-mediated resistance to antigenic therapeutic agents. Additionally, the disclosed lipid vehicles can be utilized as an intravesical drug delivery platform for antibiotic and anticancer agents in the bladder and other luminal organ systems, e.g., the distal colon and vagina.

In particular, the present invention provides a pharmaceutical composition comprising a non-cationic liposome and a physiologically acceptable carrier in which the liposome is comprised of at least one lipid.

Suitable lipids used to formulate the liposomes of the present invention can include, for example and without limitation, phospholipids, such as phosphatidylcholine (PC), phosphatidylethanolamine (PE), phosphatidylserine (PS), phosphatidylinositol (PI), phosphatidylglycerol or cardiolipin (CL); glycolipids; sphingophospholipids, such as sphingomyelin; sphingoglycolipids (also known as 1-ceramidyl glucosides), such as ceramide galactopyranoside, gangliosides and cerebrosides; cholesterol; 1,2-distearoyl-sn-glycero-3-phosphocholine (DSPC); or 1,2-dioleoylphosphatidylcholine (DOPC), but also can include various natural (e.g., tissue derived L-.alpha.-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a helper lipid. Preferred helper lipids are non-ionic or uncharged at physiological pH. Non-ionic lipids include, but are not limited to, cholesterol and DOPE (1,2-dioleolylglyceryl phosphatidylethanolamine), with cholesterol being most preferred. The molar ratio of a phospholipid to helper lipid can range from about 3:1 to about 1:1, more preferably from about 1.5:1 to about 1:1, and most preferably, the molar ratio is about 1:1.

The present invention also provides lipid vehicles comprised of a phosphaditylcholine (PC) head group, preferably sphingomyelin.

The present invention further provides a pharmaceutical composition comprising a non-cationic liposome comprised of sphingomyelin and a physiologically acceptable carrier.

The present invention still further provides a pharmaceutical composition comprising a liposome and a physiologically acceptable carrier, in which the liposome is comprised of a sphingomyelin metabolite and at least one lipid.

Sphingomyelin metabolites used to formulate the liposomes of the present invention can include, for example and without limitation, ceramide, sphingosine or sphingosine 1-phosphate.

The concentration of the sphingomyelin metabolites included in the synthetic lipids to formulate the liposomes of the present invention can range from about 0.1 mol % to about 10.0 mol %, more particularly can range from about 2.0 mol % to about 5.0 mol %, and even more particularly can be in a concentration of about 1.0 mol %.

The invention also encompasses methods of preventing, managing, ameliorating and/or treating pain (e.g., neuropathic pain) associated with cancers and/or disorders of the bladder, genitourinary tract, gastrointestinal tract, pulmonary system, and other body systems, using the disclosed lipid vehicles, in which a therapeutically effective amount of the disclosed pharmaceutical compositions is administered to an animal or human in need thereof. The disclosed lipid vehicles can be administered, for example and without limitation, via intravesical instillation to treat pain associated with IC or other conditions of the bladder, such as bladder infections and bladder cancer. In specific embodiments, these lipid vehicles may comprise vanilloids, e.g., capsaicin, resiniferatoxin, or tinyatoxin and may further comprise surface antibodies, e.g., uroplakin or NGF receptor antibodies, to target pain relief to the affected sites.

The invention includes compositions comprising lipid vehicles (e.g., micelles, microemulsions, macroemulsions and liposomes) for use as instillation vehicles, such as, for example and without limitation, intravesical vehicles, for cells or tissues. Such vehicles may further include antibodies, for example, uroplakin or NGF receptor antibodies. These antibodies may be conjugated to the surface of the liposome and act to target the liposome to specific cell types and/or receptors. Additionally, the vehicles may include compositions, including capsaicin, resiniferatoxin, tinyatoxin and other vanilloids, which can be delivered to the cells. The lipid vehicles also may include compositions comprising bioactive agents (e.g., antisense nucleic acids or peptides), drugs (e.g., pain therapeutics, anticancer treatments, or antibiotics), toxins (e.g., botulinum toxin), or other agents.

The present invention further encompasses methods of treating various disorders, e.g., defects or diseases of the genitourinary tract, gastrointestinal tract, pulmonary system, and other body systems, using the disclosed lipid vehicles. In particular, the disclosed lipid vehicles can be administered via intravesical instillation to treat interstitial cystitis (IC), urinary detrusor-sphincter dyssynergia (UDSD), spastic neurogenic bladder, hyperactive bladder, or other conditions of the genitourinary system. The disclosed lipid vehicles also can be administered intravesically to treat systemic infections and cancers, utilizing the unique interaction of the disclosed vehicles as a novel route for prolonged delivery of such therapies.

The invention also encompasses methods of treating pain (e.g., neuropathic pain) associated with cancers and/or disorders of the bladder, genitourinary tract, gastrointestinal tract, pulmonary system, and other body systems, using the disclosed lipid vehicles. In particular, the disclosed vehicles can be administered, for example and without limitation, via intravesical instillation to treat pain associated with IC, or other conditions of the bladder, such as bladder infections and bladder cancer. In specific embodiments, these vehicles may comprise vanilloids, e.g., capsaicin, resiniferatoxin, or tinyatoxin, and may further comprise surface antibodies, e.g., uroplakin or NGF receptor antibodies, to target pain relief to the affected sites.

Further encompassed are methods of treating disorders associated with involuntary muscle contraction (e.g., dystonia, dyssynergia, and spasticity) affecting the genitourinary tract, gastrointestinal tract, pulmonary system, or other body systems, using the disclosed lipid vehicles. In one aspect, the disclosed vehicles can be administered via intravesical instillation to treat muscle contractions caused by IC, UDSD, spastic neurogenic bladder, or related conditions. The lipid vehicles may be empty or may carry toxins, e.g., botulinum toxins, to deliver relief from muscle contractions at the affected sites.

BRIEF DESCRIPTION OF THE DRAWINGS

The appended drawings of the figures are presented to further describe the invention and to assist in its understanding through clarification of its various aspects.

FIGS. 9B, 9D, and 8F show saline infusion (control), PS/KCl infusion and KCl infusion, respectively, in the control animal. FIGS. 9A, 9C and 9E show saline infusion (control), PS/KCl infusion and liposomal infusion in the presence of maintenance KCl, respectively;

FIGS. 10B, 10D and 10F show saline infusion (control), AA infusion and saline infusion, respectively, in the control animal. FIGS. 10A, 10C and 10E show saline infusion (control), AA infusion and liposomal infusion in the presence of maintenance AA, respectively;

FIG. 11A shows a control CMG measured before PS treatment. FIG. 11B shows a CMG measured during treatment with low concentrations of PS. FIG. 11C shows a control CMG measured before PS treatment. FIG. 10D shows a CMG measured during treatment with high concentrations of PS.

FIG. 12A shows a control CMG measured before KCl treatment. FIG. 12B shows a CMG measured during treatment with 100 mM KCl. FIG. 11C shows a control CMG measured before KCl treatment. FIG. 12D shows a CMG measured during treatment with 300 mM KCl. FIG. 12E shows a control CMG measured before KCl treatment. FIG. 12F shows a CMG measured during treatment with 500 mM KCl.

FIG. 13A shows a control CMG measured before KCl treatment. FIG. 13B shows a CMG measured during KCl treatment.

DETAILED DESCRIPTION OF THE INVENTION

Figure 1:
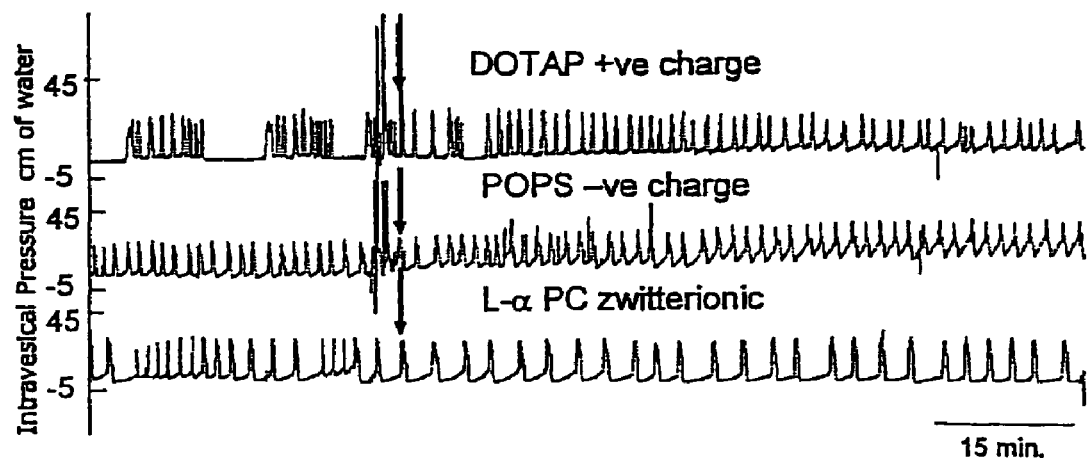
FIG. 1 is a cystometrogram (CMG) showing the effect of charge carried on a lipid headgroup in reducing bladder hyperactivity. The black arrow marks the start of infusion of liposomes in the presence of KCl (500 mM)

The present invention encompasses improved treatments for pain (e.g., neuropathic pain), pain-intensive disorders (e.g., IC), muscle contraction disorders (e.g., IC, hyperactive bladder and UDSD) and related conditions by providing compositions and methods for the administration of lipid vehicles in an animal or human in need thereof. Lipid vehicles provide non-toxic vehicles for the delivery of lipophilic therapeutic agents that have irritative side effects (e.g., vanilloids such as capsaicin) or undesirable antigenicity (e.g., botulinum toxin). Advantageously, the disclosed lipid vehicles can be used simultaneously to deliver and to ameliorate irritation caused by irritating therapeutic agents. The lipid vehicles also can be used to reduce or prevent antibody-mediated resistance to antigenic therapeutic agents. Additionally, the disclosed lipid vehicles can be utilized as an intravesical drug delivery platform for antibiotic and anticancer agents in the bladder and other luminal organ systems, e.g., the distal colon and vagina.

In an embodiment, the present invention provides a pharmaceutical composition comprising a non-cationic liposome and a physiologically acceptable carrier in which the liposome is comprised of at least one lipid.

Suitable lipids used to formulate the liposomes of the present invention can include, for example and without limitation, phospholipids, such as phosphatidylcholine (PC), phosphatidylethanolamine (PE), phosphatidylserine (PS), phosphatidylinositol (PI), phosphatidylglycerol or cardiolipin (CL); glycolipids; sphingophospholipids, such as sphingomyelin; sphingoglycolipids (also known as 1-ceramidyl glucosides), such as ceramide galactopyranoside, gangliosides and cerebrosides; cholesterol; 1,2-distearoyl-sn-glycero-3-phosphocholine (DSPC); or 1,2-dioleoylphosphatidylcholine (DOPC), but also can include various natural (e.g., tissue derived L-.alpha.-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a helper lipid. Preferred helper lipids are non-ionic or uncharged at physiological pH. Non-ionic lipids include, but are not limited to, cholesterol and DOPE (1,2-dioleolylglyceryl phosphatidylethanolamine), with cholesterol being most preferred. The molar ratio of a phospholipid to helper lipid can range from about 3:1 to about 1:1, more preferably from about 1.5:1 to about 1:1, and most preferably, the molar ratio is about 1:1.

In another embodiment, the present invention provides lipid vehicles comprised of a phosphaditylcholine (PC) head group, preferably sphingomyelin.

In a further embodiment, the present invention provides a pharmaceutical composition comprising a non-cationic liposome comprised of sphingomyelin and a physiologically acceptable carrier.

In still a further embodiment, the present invention provides a pharmaceutical composition comprising a liposome and a physiologically acceptable carrier, in which the liposome is comprised of a sphingomyelin metabolite and at least one lipid.

Sphingomyelin metabolites used to formulate the liposomes of the present invention can include, for example and without limitation, ceramide, sphingosine or sphingosine 1-phosphate.

The concentration of the sphingomyelin metabolites included in the synthetic lipids to formulate the liposomes of the present invention can range from about 0.1 mol % to about 10.0 mol %, more particularly can range from about 2.0 mol % to about 5.0 mol %, and even more particularly can be in a concentration of about 1.0 mol %.

The invention also encompasses methods of preventing, managing, ameliorating and/or treating pain (e.g., neuropathic pain) associated with cancers and/or disorders of the bladder, genitourinary tract, gastrointestinal tract, pulmonary system, and other body systems, using the disclosed lipid vehicles, in which a therapeutically effective amount of the disclosed pharmaceutical compositions is administered to an animal or human in need thereof. The disclosed lipid vehicles can be administered, for example and without limitation, via intravesical instillation to treat pain associated with IC or other conditions of the bladder, such as bladder infections and bladder cancer. In specific embodiments, these lipid vehicles may comprise vanilloids, e.g., capsaicin, resiniferatoxin, or tinyatoxin and may further comprise surface antibodies, e.g., uroplakin or NGF receptor antibodies, to target pain relief to the affected sites.

The invention includes compositions comprising lipid vehicles (e.g., micelles, microemulsions, macroemulsions and liposomes) for use as instillation vehicles, such as, for example and without limitation, intravesical vehicles, for cells or tissues. Such vehicles may further include antibodies, for example, uroplakin or NGF receptor antibodies. These antibodies may be conjugated to the surface of the liposome and act to target the liposome to specific cell types and/or receptors. Additionally, the vehicles may include compositions, including capsaicin, resiniferatoxin, tinyatoxin and other vanilloids, which can be delivered to the cells. The lipid vehicles also may include compositions comprising bioactive agents (e.g., antisense nucleic acids or peptides), drugs (e.g., pain therapeutics, anticancer treatments, or antibiotics), toxins (e.g., botulinum toxin), or other agents.

The present invention further encompasses methods of treating various disorders, e.g., defects or diseases of the genitourinary tract, gastrointestinal tract, pulmonary system, and other body systems, using the disclosed lipid vehicles. In particular, the disclosed lipid vehicles can be administered via intravesical instillation to treat interstitial cystitis (IC), urinary detrusor-sphincter dyssynergia (UDSD), spastic neurogenic bladder, hyperactive bladder, or other conditions of the genitourinary system. The disclosed lipid vehicles also can be administered intravesically to treat systemic infections and cancers, utilizing the unique interaction of the disclosed vehicles as a novel route for prolonged delivery of such therapies.

The invention also encompasses methods of treating pain (e.g., neuropathic pain) associated with cancers and/or disorders of the bladder, genitourinary tract, gastrointestinal tract, pulmonary system, and other body systems, using the disclosed lipid vehicles. In particular, the disclosed vehicles can be administered, for example and without limitation, via intravesical instillation to treat pain associated with IC, or other conditions of the bladder, such as bladder infections and bladder cancer. In specific embodiments, these vehicles may comprise vanilloids, e.g., capsaicin, resiniferatoxin, or tinyatoxin, and may further comprise surface antibodies, e.g., uroplakin or NGF receptor antibodies, to target pain relief to the affected sites.

Further encompassed are methods of treating disorders associated with involuntary muscle contraction (e.g., dystonia, dyssynergia, and spasticity) affecting the genitourinary tract, gastrointestinal tract, pulmonary system, or other body systems, using the disclosed lipid vehicles. In one aspect, the disclosed vehicles can be administered via intravesical instillation to treat muscle contractions caused by IC, UDSD, spastic neurogenic bladder, or related conditions. The lipid vehicles may be empty or may carry toxins, e.g., botulinum toxins, to deliver relief from muscle contractions at the affected sites.

The administration of the disclosed lipid vehicles are capable of providing long-lasting treatment to diseased or dysfunctional cells, tissues, or body systems. In particular, the present invention provides treatments for urinary system components, e.g., kidneys, ureters, bladders, sphincter muscles, and urethras. Specifically encompassed are treatments for bladder irritation and irritation-induced bladder dysfunction. In accordance with the present invention, non-cationic, nonionic liposomes are formulated to act as a drug with prolonged efficacy for topical bladder instillation, and bladder-protective effects. The efficacy and protective effects of such formulations are unexpected and surprising. Advantageously, the disclosed liposomes can be used simultaneously to deliver and ameliorate irritation caused by irritating therapeutic agents, e.g., resiniferatoxin or other vanilloid agents. The disclosed methods of administering the liposomes, such as by intravesical administration, provide novel treatments for IC patients. Such methods also can be employed for the treatment of other disorders of the urinary system, bladder, genitourinary tract, gastrointestinal tract, pulmonary system, and other body organs and systems, including cancers, infections, and spasticity.

In one embodiment, the present invention encompasses a pharmaceutical composition comprising a non-cationic liposome and a physiologically acceptable carrier in which the liposome is comprised of at least one lipid.

Suitable lipids used to formulate the liposomes of the present invention can include, for example and without limitation, phospholipids, such as phosphatidylcholine (PC), phosphatidylethanolamine (PE), phosphatidylserine (PS), phosphatidylinositol (PI), phosphatidylglycerol or cardiolipin (CL); glycolipids; sphingophospholipids, such as sphingomyelin; sphingoglycolipids (also known as 1-ceramidyl glucosides), such as ceramide galactopyranoside, gangliosides and cerebrosides; cholesterol; 1,2-distearoyl-sn-glycero-3-phosphocholine (DSPC); or 1,2-dioleoylphosphatidylcholine (DOPC), but also can include various natural (e.g., tissue derived L-.alpha.-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a helper lipid. Preferred helper lipids are non-ionic or uncharged at physiological pH. Non-ionic lipids include, but are not limited to, cholesterol and DOPE (1,2-dioleolylglyceryl phosphatidylethanolamine), with cholesterol being most preferred. The molar ratio of a phospholipid to helper lipid can range from about 3:1 to about 1:1, more preferably from about 1.5:1 to about 1:1, and most preferably, the molar ratio is about 1:1.

In an embodiment, the lipid vehicles comprise a phosphatidylcholine (PC) head group, and more preferably is sphingomyelin.

In another embodiment, the pharmaceutical composition of the present invention comprises a non-cationic liposome comprised of sphingomyelin and a physiologically acceptable carrier.

In a further embodiment, the present invention encompasses a pharmaceutical composition comprising a liposome and a physiologically acceptable carrier, in which the liposome is comprised of a sphingomyelin metabolite and at least one lipid.

Sphingomyelin metabolites used to formulate the liposomes of the present invention can include, for example and without limitation, ceramide, sphingosine or sphingosine 1-phosphate.

The concentration of the sphingomyelin metabolites included in the synthetic lipids to formulate the liposomes of the present invention can range from about 0.1 mol % to about 10.0 mol %, more particularly can range from about 2.0 mol % to about 5.0 mol %, and even more particularly can be in a concentration of about 1.0 mol %.

In a further embodiment, the present invention provides methods of preventing, managing, ameliorating and/or treating hyperactivity bladder disorders in an animal or a human in need thereof, in which a therapeutically effective amount of the disclosed pharmaceutical compositions is administered to the animal or human.

The methods of the present invention can be used to treat an animal, preferably a mammal, more preferably a human subject. The dosage and frequency of administration of the pharmacological compositions of the present invention typically will vary according to factors specific for each patient depending on the severity and type of disorder, the route of administration, as well as age, body weight, response, and the past medical history of the patient. Suitable regimens can be selected by one skilled in the art by considering such factors and by following, for example, dosages reported in the literature and recommended in the Physician's Desk Reference (56th ed., 2002). In some embodiments, therapeutically effective dosage amounts of the pharmaceutical compositions of the present invention can range from about 0.1 mg to about 20 mg, preferably from about 0.5 mg to about 10 mg, and more preferably from about 1.0 mg to about 5.0 mg of active ingredient per kilogram body weight of the patient per day.

The pharmaceutical compositions of the invention can include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a liposome of the present invention and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, adjuvant, or other composition with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, also can contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with anions such as those derived from hydrochloric, phosphoric, acetic, oxalic, tartaric, mandelic acids, etc.; those formed with cations such as those derived from sodium, potassium, ammonium, calcium, ferric hydroxides, isopropylamine, triethylamine, 2-ethylamino ethanol, histidine, procaine, etc.; and those formed with organic bases such as those derived from isopropylamine, trimethylamine, 2-ethylamino ethanol, histidine, procaine, etc.

Further guidance in preparing pharmaceutical formulations is found in, e.g., Gilman et al. (eds), 1990, Goodman and Gilman's: The Pharmacological Basis of Therapeutics, 8th ed., Pergamon Press; and Remington's Pharmaceutical Sciences, 17th ed., 1990, Mack Publishing Co., Easton, Pa.; Avis et al. (eds), 1993, Pharmaceutical Dosage Forms: Parenteral Medications, Dekker, NY; Lieberman et al. (eds), 1990, Pharmaceutical Dosage Forms: Disperse Systems, Dekker, NY.

Various methods of administering a vehicle of the invention include, but are not limited to, parenteral administration (e.g., intradermal, intramuscular, intraperitoneal, intravenous, subcutaneous, intravesical, transdermal, intra-arterial, intrathecal, and enteral), epidural, and mucosal (e.g., intranasal, inhaled, sublingual, oral, and rectal routes). The vehicles of the invention may be administered by any convenient route, for example by infusion or bolus injection, by absorption through epithelial or mucocutaneous linings (e.g., oral, nasal, rectal, intestinal, and vaginal mucosa, etc.). In preferred embodiments, the vehicles of the invention are administered through a catheter to the desired area (including, but not limited to, the bladder, genitourinary tract, gastrointestinal tract). Administration can be systemic or local and may be done together with other biologically active agents.

In a specific embodiment, the lipid vehicles of the present invention are administered by intravesical instillation.

The lipid vehicles of the present invention encompass micelles, microemulsions, macroemulsions, liposomes, and similar carriers. The term micelle refers to a colloidal aggregate of amphipathic (surfactant) molecules which are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. As described herein, microemulsions are essentially swollen micelles, although not all micellar solutions can be swollen to form microemulsions. Microemulsions are thermodynamically stable, are formed spontaneously and contain particles that are extremely small. Droplet diameters in microemulsions typically range from 10 to 100 nm. In contrast, the term macroemulsion refers to an emulsion of droplets with diameters greater than 100 nm. As described herein, liposomes are closed lipid vesicles comprising lipid bilayers that encircle aqueous interiors. Liposomes typically have diameters of 25 nm to 1 µm (see, e.g., D. O. Shah (ed), 1998, Micelles, Microemulsions, and Monolayers: Science and Technology, Marcel Dekker; A. S. Janoff (ed), 1998, Liposomes: Rational Design, Marcel Dekker).

Lipid vehicles of the present invention may carry a bioactive agent (e.g., a nucleic acid, polypeptide, peptide, or antibody molecule) or drug (e.g., one or more pepper extract compounds such as capsaicin, resiniferatoxin, tinyatoxin and other vanilloids, as well as antibiotics, anti-inflammatory agents and antispasmodics). As used herein, the terms nucleic acid and polynucleotide are synonymous, and refer to purine- and pyrimidine-containing polymers of any length, either polyribonucleotides or polydeoxyribonucleotides or mixed polyribo-polydeoxyribonucleotides. The terms protein and polypeptide are synonymous as used herein, and refer to polymers comprising amino acid residues linked by peptide bonds. Peptides are defined as fragments or portions of polypeptides, preferably fragments or portions having at least one functional activity (e.g., binding, antigenic, or catalytic activity) as the complete polypeptide sequence (see, e.g., by H. Lodish et al., 1999, Molecular Cell Biology, W. H. Freedman and Sons, NY; L. Stryer, 2001, Biochemistry, W. H. Freedman and Sons, NY; B. Lewin, 1999, Genes VII, Oxford University Press).

In one embodiment, the lipid vehicle is a liposome formulation in which a drug is contained therein. In a preferred embodiment, the drug is an organic or inorganic small molecule.

As used herein, the terms nucleic acid and polynucleotide are synonymous, and refer to purine- and pyrimidine-containing polymers of any length, either polyribonucleotides or polydeoxyribonucleotides or mixed polyribo-polydeoxyribonucleotides.

As used herein, the terms protein and polypeptide are synonymous and refer to polymers comprising amino acid residues linked by peptide bonds.

As used herein, the term peptides is defined as fragments or portions of polypeptides, preferably fragments or portions having at least one functional activity (e.g., binding, antigenic, or catalytic activity) as the complete polypeptide sequence (see, e.g., by H. Lodish et al., 1999, Molecular Cell Biology, W. H. Freedman and Sons, NY; L. Stryer, 2001, Biochemistry, W. H. Freedman and Sons, NY; B. Lewin, 1999, Genes VII, Oxford University Press).

The liposomes comprising the pharmaceutical composition of the present invention differ from so called "empty" liposomes known in the art, i.e, liposomes that serve as vehicles that encompass active agents but which themselves are biologically inert. Rather, the inventive liposomes are themselves biologically effective active agents.

A liposome used for the preparation of a vehicle of the invention is, in simplest form, composed of two lipid layers. The lipid layer may be a monolayer, or may be multilamellar and include multiple layers. Constituents of the liposome may include, for example, phosphatidylcholine, cholesterol, phosphatidylethanolamine, etc. Phosphatidic acid, which imparts an electric charge, may also be added. Exemplary amounts of these constituents used for the production of the liposome include, for instance, 0.3 to 1 mol, preferably 0.4 to 0.6 mol of cholesterol; 0.01 to 0.2 mol, preferably 0.02 to 0.1 mol of phosphatidylethanolamine; 0.0 to 0.4 mol, preferably 0 to 0.15 mol of phosphatidic acid per 1 mol of phosphatidylcholine.

Liposomes are self-assembling structures which include concentric amphipathic lipid (e.g., phospholipid) bilayers separated by aqueous compartments (see, e.g., Reimer, K. et al., 1997, Dermatology 195(2):S93, 1997). The amphipathic lipid molecules include a polar headgroup region covalently linked to one or two non-polar acyl chains. The energetically unfavorable contact between the hydrophobic acyl chains and the aqueous solution surrounding the lipid molecules cause the polar headgroups and acyl chains to rearrange. The polar headgroups become oriented toward the aqueous solution while the acyl chains orient towards the interior part of the bilayer. The lipid bilayer structure thus includes two opposing monolayers in which the acyl chains are shielded from contact with the surrounding medium.

Liposomes of the present invention can be constructed by well-known techniques (see, e.g., Gregoriadis, G. (ed.), Liposome Technology, Vols. 1-3, CRC Press, Boca Raton, Fla., 1993). Lipids typically are dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water, optionally containing a buffer and/or electrolyte, is added and the vessel agitated to suspend the lipid. Optionally, the suspension then is subjected to ultrasound, either in an ultrasonic bath or with a probe sonicator until the particles are reduced in size and the suspension is of the desired clarity.

The exact composition of the liposomes will depend on the particular circumstances for which they are to be used. Those of ordinary skill in the art will find it a routine matter to determine a suitable composition.

In an embodiment, the liposomes of the present invention consist essentially of a single type of phospholipid. In such embodiments, the phospholipid is phosphatidylcholine (PC), more preferably sphingomyelin. In another preferred embodiment, the liposomes of the present invention comprise sphingomyelin metabolites in a mixture with a synthetic lipid, such as, for example and without limitation, 1,2-distearoyl-sn-glycero-3-phosphocholine (DSPC) and 1,2-dioleoylphosphatidylcholine (DOPC).

Liposomes can be produced in accordance with established methods. For example, a mixture of the above-mentioned lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, Proc. Natl. Acad. Sci. USA 75:4194-4198, 1978). Unilamellar vesicles also can be prepared by sonication or extrusion. Sonication is generally performed with a bath-type sonifier, such as a Branson tip sonifier (G. Heinemann Ultrashall und Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes also can be formed by extrusion through an asymmetric ceramic filter, such as a Ceraflow Microfilter (commercially available from the Norton Company, Worcester, Mass.).

Following liposome preparation, the liposomes that have not been sized during formation may be sized by extrusion to achieve a desired size range and relatively narrow distribution of liposome sizes. A size range of about 0.2-0.4 microns will allow the liposome suspension to be sterilized by filtration through a conventional filter (e.g., a 0.22 micron filter). The filter sterilization method can be carried out on a high throughput basis.

Several techniques are available for sizing liposomes to a desired size, including, ultrasonication, high-speed homogenization, and pressure filtration (M. J. Hope et al., 1985, Biochimica et Biophysica Acta 812:55; U.S. Pat. Nos. 4,529, 561 and 4,737,323). Sonicating a liposome suspension either by bath or probe sonication produces a progressive size reduction down to small unilamellar vesicles less than about 0.05 microns in size. Multilamellar vesicles can be recirculated through a standard emulsion homogenizer until selected liposome sizes, typically between about 0.1 and 0.5 microns.

The size of the liposomal vesicles may be determined by quasi-elastic light scattering (QELS) (see Bloomfield, 1981, Ann. Rev. Biophys. Bioeng. 10:421-450). Average liposome diameter may be reduced by sonication of formed liposomes. Intermittent sonication cycles may be alternated with QELS assessment to guide efficient liposome synthesis.

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present invention, liposomes have a size of about 0.05 microns to about 0.5 microns. More preferred are liposomes having a size of about 0.05 to about 0.2 microns.

Various conditions can be used to trigger the liposome to release its payload or active agent, including pH, ionic strength, controlled release and antibody attachment. Research related to pH-sensitive liposomes has focused principally on anionic liposomes comprised largely of phosphatidylethanolamine (PE) bilayers (see, Huang et al., 1989, Biochemistry 28:9508-9514; Duzgunes et al., 1990, "pH-Sensitive Liposomes," Membrane Fusion, J. Wilschut and D. Hoekstra (eds.), Marcel-Decker Inc., New York, N.Y. pp. 713-730; Yatvin et al., 1980, Science, 210, 1253-1255). More recently, pH-sensitive cationic liposomes have been developed to mediate transfer of DNA into cells. For instance, researchers have described a series of amphiphiles with headgroups containing imidazole, methylimidazole, or aminopyridine moieties (see, Budker et al., 1996, Nature Biotech. 14:760-764). Also described are lipid molecules within liposome assemblies that are capable of structural reorganization upon a change in pH (see, e.g., U.S. Pat. No. 6,200,599 to Nantz et al.).

From the detailed description herein, it will be clear to those skilled in the art that the lipid vehicles of the present invention are useful for both in vitro and in vivo applications. For example, the lipid vehicles of the present invention will find use for nearly any in vitro or in vivo application requiring delivery of bioactive agents (e.g., nucleic acids, peptides, polypeptides or antibodies) and/or drugs (e.g., pain therapeutics, anticancer treatments or antibiotics) into cells.

Sphingomyelin is a phospholipid which belongs to the class of sphingolipids, a diverse family of phospholipids and glycolipids mediating cell to cell interactions through different signal transduction pathways. More than half of the total phospholipid content in eukaryotic membrane lipids is constituted by sphingomyelin or phosphatidylcholine (PC), residing mostly in the outer leaflet of plasma membranes. The structure of sphingomyelin includes a sphingosine backbone and a polar headgroup, phosphorylcholine. Sphingosine is an amino alcohol formed from palmitate and serine, in which the amino terminal is acylated with a long-chain acyl CoA, which yields ceramide. Subsequent substitution of the terminal hydroxyl group by phosphatidylcholine forms sphingomyelin. Sphingomyelin is present in all eukaryotic cell membranes, but is mainly present in cells of the nervous system.

Ceramide is formed by the hydrolysis of sphingomyelin by at least five different sphingomyelinases: neutral sphingomyelinase in the plasma membrane and cytosol, and acid sphingomyelinases in endosomes and lysosomes. Enzymatic cleavage of sphingomyelin is believed to be activated by various cytokines. It is known that enzymatic formation of ceramide from sphingomyelin can result in aggregation and partial fusion of liposomes to cell membranes. Sphingosine is generated from ceramide by the action of ceramidase.

Although both sphingomyelin and PC share the same polar headgroup, phosphorylcholine, they differ in the interfacial and hydrophobic parts of their molecules. For example, sphingomyelin has a higher average saturation state of its acyl chains and a greater capacity to form inter- and intra-molecular hydrogen bonds, which can result in significant deviations in the macroscopic properties of the respective bilayers of liposomes comprised of sphingomyelin. Additionally, sphingomyelin contains both hydrogen bond donating and accepting groups, while PC only contains hydrogen bond accepting groups.

Sphingomyelin metabolites, which include, for example and without limitation, ceramide, sphingosine and sphingosine-1-phosphate, are important intracellular and intercellular signaling molecules activated by the sphingomyelin signal transduction cascade in response to inflammatory cytokines (TNF-a, IFN-g and IL-1b) to ischemia/reperfusion and by hormone first messengers. Sphingomyelin metabolites have extracellular actions through specific receptors at the cell surface, leading to the activation of downstream pathways and intracellular actions directly acting on intracellular calcium stores and on several enzymatic activities. Sphingomyelin metabolites therefore mediate a variety of cellular responses including calcium signaling, platelet activation, cell proliferation and regulation of apoptosis.

In practicing the present invention, many conventional techniques in molecular biology, microbiology, and recombinant DNA may be employed. Such techniques are well known and are explained fully in, for example, Sambrook et al., 1989, Molecular Cloning: A Laboratory Manual, Second Edition, Cold Spring Harbor Laboratory Press, Cold Spring Harbor, N.Y.; F. M. Ausubel et al. (eds), 1995, Current Protocols in Molecular Biology, John Wiley & Sons, Inc., New York, N.Y.; D. N. Glover (ed), 1985, DNA Cloning: A Practical Approach, Volumes I and II; M. L. Gait (ed), 1984, Oligonucleotide Synthesis; Hames and Higgins (eds), 1985, Nucleic Acid Hybridization; Hames and Higgins (eds), 1984, Transcription and Translation; Perbal, 1984, A Practical Guide to Molecular Cloning; The Series, Methods in Enzymology, Academic Press, Inc.; J. H. Miller and M. P. Calos (eds), 1987, Gene Transfer Vectors for Mammalian Cells, Cold Spring Harbor Laboratory; Wu and Grossman (eds), Methods in Enzymology, Vol. 154; Wu (ed), Methods in Enzymology, Vol. 155.

Nucleic acids of all types may be associated with the lipid vehicles of the present invention. In accordance with the present invention, nucleic acids may be single- or double-stranded molecules, i.e., DNA, RNA, or DNA-DNA, DNA-RNA or RNA-RNA hybrids, or protein nucleic acids (PNAs) formed by conjugating bases to an amino acid backbone. Nucleic acids may also be oligonucleotides such as antisense oligonucleotides, chimeric DNA-RNA polymers and ribozymes, as well as modified versions of these nucleic acids wherein the modification may be in the base, the sugar moiety, the phosphate linkage or in any combination thereof. The nucleic acids may comprise an essential gene or fragment thereof, in which the target cell or cells is deficient in some manner. This can occur where the gene is lacking or where the gene is mutated resulting in under- or over-expression. The nucleic acids also can comprise antisense oligonucleotides. Such antisense oligonucleotides may be constructed to inhibit expression of a target gene.

In one embodiment, DNA containing all or part of the coding sequence for a polypeptide, or a complementary sequence thereof, is incorporated into a vector and inserted into a lipid vehicle for gene therapy applications. In recent years, significant technological advances have been made in the area of gene therapy for both genetic and acquired diseases (Kay et al., 1997, Proc. Natl. Acad. Sci. USA, 94:12744-12746). Gene therapy can be defined as the transfer of DNA for therapeutic purposes. Improvement in gene transfer methods has allowed for development of gene therapy protocols for the treatment of diverse types of diseases. Gene therapy also has taken advantage of recent advances in the identification of new therapeutic genes, improvement in both viral and non-viral gene delivery systems, better understanding of gene regulation and improvement in cell isolation and transplantation. Gene therapy can be carried out according to generally accepted methods as described by, for example, Friedman, 1991, Therapy for Genetic Diseases, Friedman, Ed., Oxford University Press, pages 105-121.

Vectors for introduction of genes both for recombination and for extrachromosomal maintenance are known in the art, and any suitable vector may be used. Methods for introducing DNA into cells are known in the art, and the choice of method is within the competence of one skilled in the art (Robbins (ed), 1997, Gene Therapy Protocols, Human Press, NJ). Gene transfer systems known in the art may be useful in the practice of the gene therapy methods of the present invention. These include viral and non-viral transfer methods.

A number of viruses have been used as gene transfer vectors, including polyoma, i.e., SV40 (Madzak et al., 1992, J. Gen. Virol., 73:1533-1536), adenovirus (Berkner, 1992, Curr. Top. Microbiol. Immunol. 158:39-46; Berkner et al., 1988, Bio Techniques, 6:616-629; Gorziglia et al., 1992, J. Virol., 66:4407-4412; Quantin et al., 1992, Proc. Natl. Acad. Sci. USA, 89:2581-2584; Rosenfeld et al., 1992, Cell, 68:143-155; Wilkinson et al., 1992, Nucl. Acids Res., 20:2233-2239; Strafford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; Ohi et al., 1990, Gene, 89:279-282), herpes viruses including HSV and EBV (Margolskee, 1992, Curr. Top. Microbiol. Immunol., 158:67-90; Johnson et al., 1992, J. Virol, 66:2952-2965; Fink et al., 1992, Hum. Gene Ther., 3:11-19; Breakfield et al., 1987, Mol. Neurobiol., 1:337-371; Fresse et al., 1990, Biochem. Pharmacol., 40:2189-2199), and retroviruses of avian (Brandyopadhyay et al., 1984, Mol. Cell Biol., 4:749-754; Petropoupolos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407) and human origin (Page et al., 1990, J. Virol., 64:5370-5276; Buchschalcher et al., 1992, J. Virol., 66:2731-2739). Most human gene therapy protocols have been based on disabled murine retroviruses.

Non-viral gene transfer methods known in the art include chemical techniques such as calcium phosphate coprecipitation (Graham et al., 1973, Virology, 52:456-467; Pellicer et al., 1980, Science, 209:1414-1422), mechanical techniques, for example microinjection (Anderson et al., 1980, Proc. Natl. Acad. Sci. USA, 77:5399-5403; Gordon et al., 1980, Proc. Natl. Acad. Sci. USA, 77:7380-7384; Brinster et al., 1981, Cell, 27:223-231; Constantini et al., 1981, Nature, 294:92-94), membrane fusion-mediated transfer via liposomes (Feigner et al., 1987, Proc. Natl. Acad. Sci. USA, 84:7413-7417; Wang et al., 1989, Biochemistry, 28:9508-9514; Kaneda et al., 1989, J. Biol. Chem., 264:12126-12129; Stewart et al., 1992, Hum. Gene Ther., 3:267-275; Nabel et al., 1990, Science, 249:1285-1288; Lim et al., 1992, Circulation, 83:2007-2011) and direct DNA uptake and receptor-mediated DNA transfer (Wolff et al., 1990, Science, 247:1465-1468; Wu et al., 1991, BioTechniques, 11:474-485; Zenke et al., 1990, Proc. Natl. Acad. Sci. USA, 87:3655-3659; Wu et al., 1989, J. Biol. Chem., 264:16985-16987; Wolff et al., 1991, BioTechniques, 11:474-485; Wagner et al., 1991, Proc. Natl. Acad. Sci. USA, 88:4255-4259; Cotten et al., 1990, Proc. Natl. Acad. Sci. USA, 87:4033-4037; Curiel et al., 1991, Proc. Natl. Acad. Sci. USA, 88:8850-8854; Curiel et al., 1991, Hum. Gene Ther., 3:147-154).

In one approach, plasmid DNA is complexed with a polylysine-conjugated antibody specific to the adenovirus hexon protein, and the resulting complex is bound to an adenovirus vector. The trimolecular complex then is used to infect cells. The adenovirus vector permits efficient binding, internalization, and degradation of the endosome before the coupled DNA is damaged. In another approach, liposome/DNA is used to mediate direct in vivo gene transfer. While in standard liposome preparations the gene transfer process is non-specific, localized in vivo uptake and expression have been reported in tumor deposits, for example, following direct in situ administration (Nabel, 1992, Hum. Gene Ther., 3:399-410).

Suitable gene transfer vectors possess a promoter sequence, preferably a promoter that is cell-specific and placed upstream of the sequence to be expressed. The vectors may also contain, optionally, one or more expressible marker genes for expression as an indication of successful transfection and expression of the nucleic acid sequences contained in the vector. Additionally, vectors can be optimized to minimize undesired immunogenicity and maximize long-term expression of the desired gene product(s) (see Nabe, 1999, Proc. Natl. Acad. Sci. USA 96:324-326). Moreover, vectors can be chosen based on cell-type that is targeted for treatment.

Illustrative examples of vector constructs for transfection or infection of the host cells include replication-defective viral vectors, DNA virus or RNA virus (retrovirus) vectors such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors normally will be substantially free of any prokaryotic DNA and may comprise a number of different functional nucleic acid sequences. An example of such functional sequences may be a DNA region comprising transcriptional and translational initiation and termination regulatory sequences, including promoters (e.g., strong promoters, inducible promoters and the like) and enhancers which are active in the host cells. Also included as part of the functional sequences is an open reading frame (polynucleotide sequence) encoding a protein of interest. Flanking sequences also may be included for site-directed integration. In some situations, the 5'-flanking sequence will allow homologous recombination, thus changing the nature of the transcriptional initiation region, so as to provide for inducible or non-inducible transcription to increase or decrease the level of transcription, as an example.

In general, an encoded and expressed polypeptide may be intracellular, i.e., retained in the cytoplasm, nucleus or in an organelle, or may be secreted by the cell. For secretion, the natural signal sequence present in a polypeptide may be retained. When the polypeptide or peptide is a fragment of a protein, a signal sequence may be provided so that, upon secretion and processing at the processing site, the desired protein will have the natural sequence. Specific examples of coding sequences of interest for use in accordance with the present invention include the polypeptide-coding sequences disclosed herein.

A marker may be present for selection of cells containing the vector construct. The marker may be an inducible or non-inducible gene and will generally allow for positive selection under induction, or without induction, respectively. Examples of marker genes include neomycin, dihydrofolate reductase, glutamine synthetase and the like. The vector employed generally will also include an origin of replication and other genes that are necessary for replication in the host cells, as routinely employed by those having skill in the art.

As an example, the replication system comprising the origin of replication and any proteins associated with replication encoded by a particular virus may be included as part of the construct. The replication system must be selected so that the genes encoding products necessary for replication do not ultimately transform the cells. Such replication systems are represented by replication-defective adenovirus (see G. Acsadi et al., 1994, Hum. Mol. Genet. 3:579-584) and by Epstein-Barr virus. Examples of replication defective vectors, particularly retroviral vectors that are replication defective, are BAG, (see Price et al., 1987, Proc. Natl. Acad. Sci. USA, 84:156; Sanes et al., 1986, EMBO J., 5:3133). It will be understood that the final gene construct may contain one or more genes of interest, for example, a gene encoding a bioactive metabolic molecule. Additionally, cDNA, synthetically produced DNA, or chromosomal DNA may be employed utilizing methods and protocols known and practiced by those having skill in the art.

According to one approach for gene therapy, a vector containing an antisense sequence or encoding a polypeptide is directly injected into the recipient cells (in vivo gene therapy). Alternatively, cells from the intended recipients are explanted, genetically modified to contain the antisense or encode the polypeptide, and reimplanted into the donor (ex vivo gene therapy). An ex vivo approach provides the advantage of efficient viral gene transfer, which is superior to in vivo gene transfer approaches. In accordance with ex vivo gene therapy, the host cells are first transfected with engineered vectors containing at least one nucleic acid sequence, suspended in a physiologically acceptable carrier, excipient, or diluent such as saline or phosphate buffered saline and the like, and then administered to the host. The desired protein and/or RNA is expressed by the injected cells. The introduced gene products are thereby utilized to treat or ameliorate a disorder that is related to altered expression or function of a gene.

In one particular embodiment, an antisense nucleic acid sequence is carried by a lipid vehicle of the invention. An antisense sequence can be wholly or partially complementary to a target nucleic acid and can be DNA, or its RNA counterpart (i.e., wherein T residues of the DNA are U residues in the RNA counterpart). Antisense nucleic acids can be produced by standard techniques (see, for example, Shewmaker et al., U.S. Pat. No. 5,107,065).

An antisense nucleic acid may comprise a sequence complementary to a portion of a protein coding sequence. A portion, for example a sequence of 16 nucleotides, may be sufficient to inhibit expression of the protein. Or, an antisense nucleic acid or oligonucleotide, complementary to 5' or 3' untranslated regions, or overlapping the translation initiation codons (5' untranslated and translated regions) of target genes, or genes encoding a functional equivalent also can be effective. Accordingly, antisense nucleic acids or oligonucleotides can be used to inhibit the expression of the gene encoded by the sense strand or the mRNA transcribed from the sense strand.

Additionally, antisense nucleic acids and oligonucleotides can be constructed to bind to duplex nucleic acids either in the genes or the DNA:RNA complexes of transcription to form stable triple helix-containing or triplex nucleic acids to inhibit transcription and/or expression of a gene (Frank-Kamenetskii, M. D. and Mirkin, S. M., 1995, Ann. Rev. Biochem. 64:65-95). Such oligonucleotides of the present invention can be constructed using the base-pairing rules of triple helix formation and the nucleotide sequences of the target genes.

In preferred embodiments, at least one of the phosphodiester bonds of an antisense oligonucleotide is substituted with a structure that functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Oligonucleotides also may include species that include at least some modified base forms. Thus, purines and pyrimidines, other than those normally found in nature, may be so employed. Similarly, modifications on the furanosyl portions of the nucleotide subunits may also be affected, as long as the essential tenets of the present invention are adhered to. Examples of such modifications are 2'-O-alkyl- and 2'-halogen-substituted nucleotides. Some non-limiting examples of modifications at the 2' position of sugar moieties which are useful in the present invention include OH, SH, SCH$_3$, F, OCH$_3$, OCN, O(CH$_2$)$_n$NH$_2$ and O(CH$_2$)$_n$CH$_3$, where n is from 1 to about 10. Such oligonucleotides are functionally interchangeable with natural oligonucleotides or synthesized oligonucleotides, which have one or more differences from the natural structure. All such analogs are comprehended by the present invention so long as they function effectively to hybridize with a nucleic acid to inhibit the function thereof.

The antisense oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As defined herein, a subunit is a base and sugar combination suitably bound to adjacent subunits through phosphodiester or other bonds.

The antisense oligonucleotides used in accordance with the present invention may be conveniently and routinely made through the well-known technique of solid phase synthesis. Equipment for such synthesis is available from several vendors, including PE Applied Biosystems (Foster City, Calif.). Any other means for such synthesis may also be employed, however, the actual synthesis of the oligonucleotides is well within the abilities of the practitioner. Also well-known are methods for preparing modified oligonucleotides, such as phosphorothioates and alkylated derivatives.

The oligonucleotides of the present invention are designed to be hybridizable with target RNA (e.g., mRNA) or DNA. For example, an oligonucleotide (e.g., DNA oligonucleotide) that hybridizes to an mRNA molecule can be used to target the mRNA for RnaseH digestion. Alternatively, an oligonucleotide that hybridizes to the translation initiation site of an mRNA molecule can be used to prevent translation of the mRNA. In another approach, oligonucleotides that bind to double-stranded DNA can be administered. Such oligonucleotides can form a triplex construct and inhibit the transcription of the DNA. Triple helix pairing prevents the double helix from opening sufficiently to allow the binding of polymerases, transcription factors or regulatory molecules. Recent therapeutic advances using triplex DNA have been described (see, e.g., J. E. Gee et al., 1994, Molecular and Immunologic Approaches, Futura Publishing Co., Mt. Kisco, N.Y.).

As non-limiting examples, antisense oligonucleotides may be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region. Preferably, the complementary oligonucleotide is designed to hybridize to the most unique 5' sequence of a gene, including any of about 15 to 35 nucleotides spanning the 5' coding sequence. Appropriate oligonucleotides can be designed using OLIGO software (Molecular Biology Insights, Inc., Cascade, Colo.; http://www.oligo.net).

In accordance with the present invention, an antisense oligonucleotide can be synthesized, formulated as a pharmaceutical composition and administered to a subject. The synthesis and utilization of antisense and triplex oligonucleotides have been described previously (e.g., H. Simon et al., 1999, Antisense Nucleic Acid Drug Dev. 9:527-31; F. X. Barre et al., 2000, Proc. Natl. Acad. Sci. USA 97:3084-3088; R. Elez et al., 2000, Biochem. Biophys. Res. Commun. 269:352-6; E. R. Sauter et al., 2000, Clin. Cancer Res. 6:654-60). Alternatively, expression vectors derived from retroviruses, adenoviruses, herpes or vaccinia viruses, or from various bacterial plasmids, may be used for delivery of nucleotide sequences to the targeted organ, tissue or cell population.

Methods that are well known to those skilled in the art can be used to construct recombinant vectors which will express a nucleic acid sequence that is complementary to a target gene. These techniques are described both in Sambrook et al., 1989 and in Ausubel et al., 1992. For example, gene expression can be inhibited by transforming a cell or tissue with an expression vector that expresses high levels of untranslatable sense or antisense sequences. Even in the absence of integration into the DNA, such vectors may continue to transcribe RNA molecules until they are disabled by endogenous nucleases. Transient expression may last for a month or more with a non-replicating vector, and even longer if appropriate replication elements included in the vector system.

Various assays may be used to test the ability of antisense oligonucleotides to inhibit gene expression. For example, mRNA levels can be assessed by Northern blot analysis (Sambrook et al., 1989; Ausubel et al., 1992; J. C. Alwine et al. 1977, Proc. Natl. Acad. Sci. USA 74:5350-5354; I. M. Bird, 1998, Methods Mol. Biol. 105:325-36), quantitative or semi-quantitative RT-PCR analysis (see, e.g., W. M. Freeman et al., 1999, Biotechniques 26:112-122; Ren et al., 1998, Mol. Brain Res. 59:256-63; J. M. Cale et al., 1998, Methods Mol. Biol. 105:351-71), or in situ hybridization (reviewed by A. K. Raap, 1998, Mutat. Res. 400:287-298). Alternatively, polypeptide levels can be measured, e.g., by Western blot analysis, indirect immunofluorescence, or immunoprecipitation techniques (see, e.g., J. M. Walker, 1998, Protein Protocols on CD-ROM, Humana Press, Totowa, N.J.).

In specific embodiments, the lipid vehicles of the present invention carry nucleotide sequences encoding cytotoxins (e.g., diphtheria toxin (DT), Pseudomonas exotoxin A (PE), pertussis toxin (PT), and the pertussis adenylate cyclase (CYA)), antisense nucleic acids (e.g., NGF antisense), ribozymes, labeled nucleic acids and nucleic acids encoding tumor suppressor genes such as p53, p110Rb, and p72.

NGF antisense nucleic acids have been described by, e.g., K. A. Chang et al., 1999, J. Mol. Neurosci. 12(1):69-74; C. Culmsee et al., 1999, Neurochem. Int. 35(1):47-57; F. Hallbook et al., 1997, Antisense Nucleic Acid Drug Dev. 7(2):89-100. Such antisense nucleic acids can be used with the lipid vehicles of the invention for treating NGF-related diseases, including disorders of the brain (e.g., Alzheimer's) (see, e.g., K. A. Chang et al., 1999, J. Mol. Neurosci. 12(1):69-74; R. Hellweg et al., 1998, Int. J. Dev. Neurosci. 16 78:787-94) and bladder (e.g., inflammation and dysfunction) (see, e.g., M. A. Vizzard, 2000, Exp. Neurol. 161(1):273-84; D. Oddiah et al., 1998, Neuroreport. 9(7):1455-8; M. C. Dupont et al., 1995, Adv. Exp. Med. Biol. 385:41-54).

The lipid vehicles of the present invention can be conjugated to antibodies, i.e., polyclonal and/or monoclonal antibodies, fragments thereof or immunologic binding equivalents thereof. The term antibody is used both to refer to a homogeneous molecular entity, or a mixture such as a serum product made up of a plurality of different molecular entities. Antibodies can include whole antibody molecules, hybrid antibodies, chimeric antibodies and univalent antibodies. Also included are antibody fragments, including Fc, Fv, $Fab_1$, and $F(ab)_2$ fragments of antibodies.

Antibodies may be obtained from commercial sources, e.g., Jackson ImmunoResearch Laboratories, Inc., West Grove, Pa.; Advanced Targeting Systems, San Diego, Calif.; Connex GmbH (Martinsried, Germany), Covance Research Products, Cumberland, Va.; Pierce Endogen, Rockford, Ill.; DiaSorin, Stillwater, Minn.; and DAKO Corporation, Carpinteria, Calif. Alternatively, antibodies may be produced in an animal host (e.g., rabbit, goat, mouse, or other non-human mammal) by immunization with immunogenic components. Antibodies also may be produced by in vitro immunization (sensitization) of immune cells. The antibodies also may be produced in recombinant systems programmed with appropriate antibody-encoding DNA. Alternatively, the antibodies may be constructed by biochemical reconstitution of purified heavy and light chains.

An isolated polypeptide or portion thereof can be used as an immunogen to generate antibodies using standard techniques for polyclonal and monoclonal antibody preparation (see, e.g., E. Harlow and D. Lane, 1988, Antibodies: A Laboratory Manual, Cold Spring Harbor Laboratory, Cold Spring Harbor, N.Y.). A full-length polypeptide can be used or, alternatively, antigenic peptide portions can be used as immunogens. An antigenic peptide typically comprises at least 5 contiguous amino acid residues and encompasses an epitope of a polypeptide such that an antibody raised against the peptide forms a specific immune complex with the peptide. The immunogenic polypeptides or peptides for use with the present invention may be isolated from cells or may be chemically synthesized.

An appropriate immunogenic preparation can contain, for example, a recombinantly produced polypeptide or a chemically synthesized polypeptide, or portions thereof. The preparation can further include an adjuvant or similar immunostimulatory agent. A number of adjuvants are known and used by those skilled in the art. Non-limiting examples of suitable adjuvants include incomplete Freund's adjuvant, mineral gels such as alum, aluminum phosphate, aluminum hydroxide, aluminum silica and surface-active substances, such as lysolecithin, pluronic polyols, polyanions, peptides, oil emulsions, keyhole limpet hemocyanin and dinitrophenol.

Further examples of adjuvants include N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-Lalanyl-D-isoglutaminyl-L-alanine-2-(1'-2'-dipa-lmitoyl-sn-glycero-3 hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/ TWEEN®80 emulsion. A particularly useful adjuvant comprises 5% (wt/vol) squalene, 2.5% Pluronic L121 polymer and 0.2% polysorbate in phosphate buffered saline (Kwak et al., 1992, New Eng. J. Med. 327:1209 1215). Preferred adjuvants include complete BCG, Detox, (RIBI, Immunochem Research Inc.), ISCOMS, and aluminum hydroxide adjuvant (Superphos, Biosector). The effectiveness of an adjuvant may be determined by measuring the amount of antibodies directed against the immunogenic peptide.

Polyclonal antibodies to polypeptides can be prepared as described above by immunizing a suitable subject with an immunogen. The antibody titer in the immunized subject can be monitored over time by standard techniques, such as with an enzyme linked immunosorbent assay (ELISA) using immobilized polypeptide or peptide. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique (see Kohler and Milstein, 1975, Nature 256:495-497; Brown et al., 1981, J. Immunol. 127:539-46; Brown et al., 1980, J. Biol. Chem. 255:4980-83; Yeh et al., 1976, PNAS 76:2927-31; and Yeh et al., 1982, Int. J. Cancer 29:269-75), the human B cell hybridoma technique (Kozbor et al., 1983, Immunol. Today 4:72), the EBV-hybridoma technique (Cole et al., 1985, Monoclonal Antibodies and Cancer Therapy, Alan R. Liss, Inc., pp. 77 96) or trioma techniques.

The technology for producing hybridomas is well-known (see generally R. H. Kenneth, 1980, Monoclonal Antibodies: A New Dimension In Biological Analyses, Plenum Publishing Corp., New York, N.Y.; E. A. Lerner, 1981, Yale J. Biol. Med., 54:387-402; M. L. Gefter et al., 1977, Somatic Cell Genet. 3:231-36). In general, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptides or peptides.

Alternative to preparing monoclonal antibody-secreting hybridomas, a monoclonal antibody can be identified and isolated by screening a recombinant combinatorial immunoglobulin library (e.g., an antibody phage display library) with the corresponding polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP® Phage Display Kit, Catalog No. 240612).

Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al., PCT International Publication No. WO 92/01047;

Garrard et al., PCT International Publication No. WO 92/09690; Ladner et al., PCT International Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J 12:725-734; Hawkins et al., 1992, J. Mol. Biol. 226:889-896; Clarkson et al., 1991, Nature 352:624-628; Gram et al., 1992, PNAS 89:3576-3580; Garrad et al., 1991, Bio/Technology 9:1373-1377; Hoogenboom et al., 1991, Nuc. Acid Res. 19:4133-4137; Barbas et al., 1991, PNAS 88:7978-7982; and McCafferty et al., 1990, Nature 348:552-55.

Additionally, recombinant antibodies, such as chimeric and humanized monoclonal antibodies comprising both human and non-human portions, can be made using standard recombinant DNA techniques. Such chimeric and humanized monoclonal antibodies can be produced by recombinant DNA techniques known in the art, for example using methods described in Robinson et al., International Application No. PCT/US86/02269; Akira, et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al., 1988, Science 240:1041-1043; Liu et al., 1987, PNAS 84:3439-3443; Liu et al., 1987, J. Immunol. 139:3521-3526; Sun et al., 1987, PNAS 84:214-218; Nishimura et al., 1987, Canc. Res. 47:999-1005; Wood et al., 1985, Nature 314:446-449; and Shaw et al., 1988, J. Natl. Cancer Inst. 80:1553-1559; S. L. Morrison, 1985, Science 229:1202-1207; Oi et al., 1986, BioTechniques 4:214; Winter U.S. Pat. No. 5,225,539; Jones et al., 1986, Nature 321:552 525; Verhoeyan et al., 1988, Science 239:1534; and Beidler et al., 1988, J. Immunol. 141:4053-4060.

Fv fragments of monoclonal antibodies may be produced in bacteria using single chain antibody technology (U.S. Pat. No. 4,946,778 and PCT International Application No. WO 88/09344). Additionally, Fv fragments can be genetically engineered to contain glycosylation sites. These engineered Fv fragments then can be produced in mammalian cells, to result in a fragment containing carbohydrate moieties. Fab or F(ab')$_2$ fragments of monoclonal antibodies may be produced by enzymatic cleavage of whole IgG which is produced by a hybridoma or a transfected cell line (e.g., a myeloma or a cell line such as Chinese Hamster Ovary (CHO) cells), using pepsin or papain digestion, respectively.

The antibodies or antibody fragments can be conjugated to liposomes using conventional techniques (see, e.g., M. J. Ostro (ed.) 1987, Liposomes: from Biophysics to Therapeutics, Marcel Dekker, New York, N.Y.). One preferred method of preparing liposomes and conjugating immunoglobulins to their surface is described by Y. Ishimoto et al., 1984, J. Immunol. Met. 75:351-360. In accordance with this method, multilamillar liposomes composed of dipalmitoylphosphatidylcholine, cholesterol, and phosphotidylethanolamine are prepared. Purified fragments then are coupled to the phosphatidylethanolamine by the cross-linking agent N-hydroxysuccinimidyl 3-(2-pyridyldithio)propionate. The coupling of the antibody or fragment to the liposome is demonstrated by the release of a pre-trapped marker, e.g., carboxyfluorescence, from the liposomes. This release occurs upon incubation with a secondary antibody against the conjugated antibody, fragment, or complement.

The antibodies or antibody fragments also can be coupled to a liposome or another carrier of the invention via carbohydrate moieties. Such coupling can be used provided that the carbohydrate moiety is not in the hypervariable region or at the antibody binding sites. In this way, conjugation via the cross-linking with the carbohydrate will not affect binding and the binding sites will still be available to bind to cell surface antigens. One preferred method for coupling antibodies or antibody fragments of the invention (other than Fv) to a polymer backbone or a liposome involves conjugation through the carbohydrate moieties in the constant regions. This maximizes the number of available antigen-binding sites. Methods for derivatizing sugar ring moieties to create hydrazide groups for coupling with antibody fragments (and antibodies) have been established (see J. D. Rodwell et al., 1986, Proc. Natl. Acad. Sci. USA 83:2632-36). Several immunoconjugates prepared in this way are in clinical studies or pending approval for routine clinical uses.

Binding of a monoclonal antibody to the surface of a liposome also may be accomplished by the formation of cross-linkage between phosphatidylethanolamine and the antibody using glutaraldehyde. Alternatively, a thiolated antibody can be allowed to react with a liposome comprising a lipid into which a maleimide group has been incorporated. Remaining maleimide groups on the surface of the liposome may be further reacted with a compound containing thiolated polyalkyleneglycol moiety. Thiolation of an antibody or antibody fragment may be achieved through use of N-succinimidyl-3-(2-pyridyidithio)propionate (SPDP), which usually is used for thiolation of protein, iminothiolane, or mercaptoalkylimidate. Alternatively, a dithiol group endogenous to an antibody may be reduced to form a thiol group. The latter method is preferred for maintaining antibody function. In accordance with another method, whole antibodies are treated with an enzyme such as pepsin to form F(ab)$_2$ fragments, which then are reduced with dithiothreitol (DTT) to form Fab fragments, which results in the production of one to three thiol groups. The conjugation of the thiolated antibody to the maleimide group-containing liposome may be accomplished by reacting the components in a neutral buffer solution at pH 6.5 to 7.5 for 2 to 16 hours.

In specific embodiments, the lipid vehicles of the present invention are conjugated to antibodies or antibody fragments directed to NGF receptor or uroplakin.

The lipid vehicles and methods of the present invention can be used to deliver a broad range of pharmaceutical compositions and drugs. In addition to the aforementioned nucleic acids, the lipid vehicles of the present invention can carry small organic or inorganic compounds as bioactive agents. Suitable pharmaceuticals or bioactive agents include, but are not limited to, antimicrobials, antibiotics, antimycobacterial, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics and diagnostic agents.

In certain preferred aspects, the bioactive agent will be an antineoplastic agent, such as vincristine, doxorubicin, mitoxantrone, camptothecin, cisplatin, bleomycin, cyclophosphamide, methotrexate, streptozotocin and the like. Especially preferred antitumor agents include, for example, actinomycin D, vincristine, vinblastine, cystine arabinoside, anthracyclines, alkylative agents, platinum compounds, antimetabolites and nucleoside analogs, such as methotrexate and purine and pyrimidine analogs. Anticancer agents further include carcinostatic agents such as adriamycin, daunomycin, mitomycin, epirubicin, 5-FU, and aclacinomycin, toxins such as ricin A and diphtheria toxin and antisense RNA. Encapsulation of an anticancer agent into lipid vehicles can be accomplished by hydration of the lipids with an aqueous solution of the anticancer agent. Adriamycin, daunomycin, and epirubicin may be encapsulated into a liposome by means of a remote loading method that takes advantage of a pH gradient (D. M. Lawrence et al., 1989, Cancer Research 49:5922).

In certain aspects, the lipid vehicles of the present invention can be used to deliver anti-infective agents. The lipid vehicles of the present invention also can be used for the selective delivery of other drugs including, but not limited to, local anesthetics (e.g., dibucaine and chlorpromazine); beta-adrenergic blockers (e.g., propranolol, timolol and labetolol); antihypertensive agents (e.g., clonidine and hydralazine); anti-depressants (e.g., imipramine, amitriptyline and doxepim); anticonversants (e.g., phenytoin; antihistamines, e.g., diphenhydramine, chlorphenirimine and promethazine); antibiotic/antibacterial agents, e.g., gentamycin, ciprofloxacin, and cefoxitin. Also included are antibiotics such as macrolides and lincosamines (e.g., lincomycin, erythromycin, dirithromycin, clindamycin, clarithromycin, and azithromycin); ample spectrum penicillins (e.g., ticarcillin, piperacillin, mezlocillin, carbenicillin indanyl, bacampicillin, ampicillin, and amoxicillin); penicillins and beta-lactamase inhibitors (e.g., amoxicillin-clavulanic acid, ampicillin-sulbactam, benzylpenicillin, cloxacillin, dicloxacillin, methicillin, oxacillin, penicillin G (benzathine, potassium, procaine), penicillin V, piperacillin plus tazobactam and ticarcillin plus clavulanic acid); aminoglycosides (e.g., amikacin, gentamicin, kanamycin, neomycin, netilmicin, streptomycin, and tobramycin); and tetracyclines (e.g., tetracycline, oxytetracycline, minocycline, methacycline, doxycycline and demedocycline). Further included are antifungal agents (e.g., miconazole, terconazole, econazole, isoconazole, butaconazole, clotrimazole, itraconazole, nystatin, naftifine and amphotericin B); antiparasitic agents, hormones, hormone antagonists, immunomodulators, neurotransmitter antagonists, antiglaucoma agents, vitamins, narcotics and imaging agents. Those of skill in the art will know of other agents suitable for use with the formulations and methods of the present invention.

In specific embodiments, the lipid vehicles of the present invention deliver vanilloid components (e.g., resiniferatoxin, capsaicin, tinyatoxin and related compounds). Additionally, the lipid vehicles may deliver toxins (e.g., botulinum toxins, such as botulinum toxin A, botulinum toxin B, botulinum toxin C, botulinum toxin D, botulinum toxin E, botulinum toxin F and botulinum toxin G). Lipid vehicles can be formulated as described herein, or by other methods known in the art (e.g., U.S. Pat. No. 6,334,999 to Gilbert et al.; U.S. Pat. No. 6,083,530 to Mayer et al.; U.S. Pat. No. 5,939,096 to Clerc et al.; U.S. Pat. No. 5,795,589 to Mayer et al.; U.S. Pat. No. 5,744,158 to Mayer et al.; and U.S. Pat. No. 5,616,341 to Mayer et al., which are incorporated herein by reference).

Preferably, a composition (e.g., pharmaceutical composition) includes, in admixture, a pharmaceutically acceptable excipient, carrier, or diluent, and one or more of a bioactive agent (e.g., nucleic acid, polypeptide, peptide, or antibody), drug (e.g., resiniferatoxin, capsaicin, tinyatoxin, or other vanilloid compounds), or toxin (e.g., botulinum toxin), as described herein, as an active ingredient. The preparation of pharmaceutical compositions that contain bioactive agents as active ingredients is well understood in the art. Typically, such compositions are prepared as injectables, either as liquid solutions or suspensions, however, solid forms suitable for solution in, or suspension in, liquid prior to injection also can be prepared. The preparation also can be emulsified. The active therapeutic ingredient often is mixed with excipients which are pharmaceutically acceptable and compatible with the active ingredient. Suitable excipients are, for example, water, saline, dextrose, glycerol, ethanol, or the like and combinations thereof. Preferred carriers, excipients, and diluents of the invention comprise physiological saline (i.e., 0.9% NaCl). Additionally, if desired, the composition can contain minor amounts of auxiliary substances such as wetting or emulsifying agents or pH-buffering agents, which enhance the effectiveness of the active ingredient.

A bioactive agent or drug can be formulated into the pharmaceutical composition as neutralized physiologically acceptable salt forms. Suitable salts include the acid addition salts (i.e., formed with the free amino groups of the polypeptide or antibody molecule) and which are formed with inorganic acids such as, for example, hydrochloric or phosphoric acids, or such organic acids as acetic, oxalic, tartaric, mandelic and the like. Salts formed from the free carboxyl groups also can be derived from inorganic bases such as, for example, sodium, potassium, ammonium, calcium, or ferric hydroxides, and such organic bases such as isopropylamine, trimethylamine, 2-ethylamino ethanol, histidine, procaine and the like.

The pharmaceutical compositions and lipid vehicles can be administered systemically by oral or parenteral routes. Non-limiting parenteral routes of administration include subcutaneous, intravesical, intramuscular, intraperitoneal, intravenous, transdermal, inhalation, intranasal, intra-arterial, intrathecal, enteral, sublingual, or rectal. Intravenous administration, for example, can be performed by injection of a unit dose. The term unit dose when used in reference to a pharmaceutical composition of the present invention refers to physically discrete units suitable as unitary dosage for humans, each unit containing a predetermined quantity of active material calculated to produce the desired therapeutic effect in association with the required diluent, i.e., carrier. The disclosed pharmaceutical compositions and vehicles also can be administered via pulmonary inhaler or mucoactive aerosol therapy (nasal spray; see, e.g., M. Fuloria and B. K. Rubin, 2000, Respir. Care 45:868-873; 1. Gonda, 2000, J. Pharm. Sci. 89:940-945; R. Dhand, 2000, Curr. Opin. Pulm. Med. 6(1):59-70; B. K. Rubin, 2000, Respir. Care 45(6):684-94; S. Suarez and A. J. Hickey, 2000, Respir. Care. 45(6):652-66). Additionally, topical administration can be used. Preferably, the disclosed pharmaceutical compositions and vehicles are administered by intravesical instillation.

Pharmaceutical compositions can be administered in a manner compatible with the dosage formulation and in a therapeutically effective amount. The quantity to be administered depends on the subject to be treated, capacity of the subject's immune system to utilize the active ingredient and degree of modulation required. Precise amounts of active ingredient required to be administered depend on the judgment of the practitioner and are specific for each individual. However, suitable dosages may range from between about 0.1 to 20 mg, preferably from between about 0.5 to about 10 mg, and more preferably from between about one to several milligrams of active ingredient per kilogram body weight of individual per day and depending on the route of administration.

Suitable regimes for initial administration and booster shots also are variable, but are typified by an initial administration followed by repeated doses at one or more hour intervals by a subsequent injection or other administration. Alternatively, continuous intravenous infusions sufficient to maintain concentrations of 10 nM to 10 µM in the blood are contemplated. An exemplary pharmaceutical formulation comprises: a peptide or polypeptide (5.0 mg/ml); sodium bisulfite USP (3.2 mg/ml); disodium edetate USP (0.1 mg/ml); and water for injection q.s.a.d. (1.0 ml). As used herein, pg means picogram, ng means nanogram, µg means microgram, mg means milligram, µl means microliter, ml means milliliter and l means L.

Further guidance in preparing pharmaceutical formulations is found in, e.g., Gilman et al. (eds), 1990, Goodman and Gilman's: The Pharmacological Basis of Therapeutics, 8th ed., Pergamon Press; and Remington's Pharmaceutical Sciences, 17th ed., 1990, Mack Publishing Co., Easton, Pa.; Avis et al. (eds), 1993, Pharmaceutical Dosage Forms: Parenteral Medications, Dekker, N.Y.; Lieberman et al. (eds), 1990, Pharmaceutical Dosage Forms: Disperse Systems, Dekker, N.Y.

In various aspects, the present invention encompasses novel methods of treatment that utilize the disclosed liposomes and lipid vehicles. In particular, treatments are provided for cancers, infections, pain (e.g., neuropathic pain) and other conditions relating to the bladder, genitourinary tract, gastrointestinal tract, pulmonary system and other organs or body systems. Specifically encompassed are treatments for urinary system components, e.g., kidneys, ureters, bladders, sphincter muscles and urethras. Non-limiting examples of gastrointestinal organs include the esophagus, stomach, large intestine and small intestine. Pulmonary system organs include, among other organs, the trachea, lungs, bronchi, bronchioles, alveoli and cilia. Genitourinary tract organs include, but are not limited to, the bladder, kidney, urethra, ureter, prostate, penis, testes, seminiferous tubules, epididymis, vas deferens, seminal vesicles, bulbourethral (Cowper) glands, uterus, vagina and fallopian tubes. Non-limiting examples of bladder conditions include spastic neurogenic bladder, hypotonic neurogenic bladder, bladder hyperactivity, pain, irritation, inflammation, micturition pattern alteration, incontinence, infection and cancer. Bladder cancers suitable for treatment include, for example, transitional cell carcinomas, squamous cell carcinomas and adenocarcinomas. Also included are conditions relating to IC and UDSD.

The present invention further encompasses methods of treating conditions associated with involuntary muscle contractions, including but not limited to, tremor (voice, head, and limb tremor); palatal myoclonus; dysthyroid myopathy; hemifacial spasms; tics; strabismus (e.g., concomitant strabismus and vertical strabismus); nystagmus; eyelid entropion; myokymia; bruxism (TMJ); tardive dyskinetic syndrome; lateral rectus palsy; hyperkinesias following hypoglossal-facial anastomosis; myoclonus of spinal cord origin; voice defects (e.g., stuttering); painful rigidity; tension headaches; lumbosacral strain and back spasm (myofascial); radiculopathy with secondary muscle spasm; spasticity; IC; spastic bladder; UDSD; achalasia (esophageal); pelvirectal spasms (anismus and vaginismus); segmental dystonia; focal dystonia (e.g., blepharospasm (lid apraxia), oromandibular dystonia, facial dystonia, lingual dystonia, cervical dystonia (torticollis) and spasticity); laryngeal dystonia (spasmodic dysphonia; adductor spasmodic dysphonia, and abductor spasmodic dysphonia); task-specific dystonia (occupational cramps, such as writer's cramps); idiopathic and secondary focal distonia; and other spastic disorders. Treatments of involuntary contractions may be directed to any muscle group, including those associated with control of the eye(s), lip(s), tongue, mouth, jaw, head, neck, face, arm, hand, finger, leg, trunk, vagina, cervix, bladder and sphincter (e.g., esophageal, cardiac, pyloric, ileocaecal, O'Beirne, anal, urethra and bladder neck sphincters). Treatments also are provided for furrows of the face and neck, including frown lines and facial wrinkles.

The methods of the present invention can be used to treat an animal, preferably a mammal, more preferably a human subject. The disclosed methods comprise administering a liposome or lipid vehicle to a mammal suffering from one or more of these conditions. In one aspect, a lipid vehicle can carry a biological agent (e.g., nucleic acid, peptide, polypeptide or antibody), drug (e.g., pain therapeutics, anticancer treatments or antibiotics), or toxin (e.g., botulinum toxin). For example, if the disease is the result of infection by a pathogen, the nucleic acid can be an antisense oligonucleotide targeted against a DNA sequence in the pathogen that is essential for development, metabolism or reproduction of the pathogen. As another example, if the disease is related to a genetic defect (i.e., wherein certain endogenous DNA is missing or has been mutated), resulting in under- or over-expression, the nucleic acid may be the normal DNA sequence.

Several methods of in vivo lipofection have been reported. In the case of whole animals, the liposome or lipid vehicle may be injected into the blood stream, directly into a tissue, into the peritoneum, instilled into the trachea or converted to an aerosol, which the animal breathes. For example, a single intravenous injection of 100 micrograms of a mixture of DNA and DOTMA:dioleoylphosphatidylethanaolamine can be used to efficiently transfect all tissues (Zhu et al., 1993, Science 261:209-211). It also is possible to use a catheter to implant liposomes or lipid vehicles in a blood vessel wall, which can result in successful transfection of several cell types, including endothelial and vascular smooth muscle cells. In particular, aerosol delivery of a chloramphenicol acetyltransferase (CAT) expression plasmid complexed to cationic liposomes produces high-level, lung-specific CAT gene expression in vivo for at least 21 days (Stribling et al., 1992, Proc. Natl. Acad. Sci. USA 89:11277-11281). One representative method for aerosol delivery has been performed as follows: (1) 6 mg plasmid DNA and 12 µM DOTMA/DOPE liposomes were each diluted to 8 ml with water and mixed; (2) equal volumes were placed into two Acorn I nebulizers (Marquest, Englewood, Colo.; (3) animals were loaded into an Intox small-animal exposure chamber (Albuquerque) and an air flow rate of 4 L/min was used to generate the aerosol (about 90 min were required to aerosolize this volume); (4) the animals were removed from the chamber for 1 to 2 hrs and the procedure was repeated.

Specific targeting moieties can be used with the lipid vehicles of the present invention to target specific cells or tissues. In one embodiment, the targeting moiety, such as an antibody or antibody fragment, is attached to a hydrophilic polymer and is combined with the lipid vehicle after vehicle formation. Thus, the use of a targeting moiety in combination with a lipid vehicle provides the ability to conveniently customize the vehicle for delivery to specific cells and tissues. In specific embodiments, the disclosed lipid vehicles carrying drugs (e.g., pain remedies, anticancer or antibiotics) and/or bioactive agents (e.g., nucleic acids, polypeptides, peptides or antibodies) specifically can be targeted to cancer cells, immune cells (e.g., B and T cells) and cells of the bladder, genitourinary tract, gastrointestinal tract, pulmonary system or other body organs or systems. Such cells can be targeted using antibodies or antibody fragments against cell surface antigens, including various receptors or markers.

For example, many cancers are characterized by overexpression of cell surface markers such as HER2, which is expressed in breast cancer cells, or IL-13 receptor, which is expressed in gliomas (reviewed in, e.g., J. Baselga et al., 1997, Oncology (Huntingt) 11(3 Suppl 2):43-8; S. Menard et al., 2000, J. Cell. Physiol. 182(2):150-62; W. Debinski, 1998Crit. Rev. Oncog. 9(3 4):255-68). Certain urogenitary tract cancers are characterized by expression of the uroplakin marker (see, e.g., X. Xu et al., 2001, Cancer 93(3):216-21; J. J. Lu et al., 2000, Clin. Cancer Res. 6(8):3166-71; U. Kaufmann et al., 2000, Am. J. Clin. Pathol. 113(5):683-7; S. M. Li et al., 1999, J. Urol. 162(3 Pt 1):931-5; I. Yuasa et al., 1999, Int. J. Urol. 6(6):286-92; I. Yuasa et al., 1998, Jpn. J. Cancer Res. 89(9):879-82; R. L. Wu et al., 1998, Cancer Res. 58(6): 1291-7). Additionally, neurons are characterized by the expression of NGF receptor (reviewed by, e.g., L. Tessarollo, 1998, Cytokine Growth Factor Rev. 9(2):125-37; E. C. Yuen E C, et al., 1996, Brain Dev. 18(5):362-8; S. B. McMahon, 1996, Philos. Trans. R. Soc. Lond. B. Biol. Sci. 351(1338): 431-40; G. Dechant et al., 1994, Prog. Neurobiol. 42(2):347-52). Thus, targeting moieties such as anti-HER2, anti-IL-13 receptor and anti-NGF receptor antibodies or antibody fragments can be used to deliver the lipid vehicle to the cell of choice. The bioactive agent and/or drug thereby is delivered to the specific cell type, providing a useful and specific therapeutic treatment.

Cationic lipid-assisted drug delivery can be accomplished in accordance with well-established methods. For drugs that are soluble in organic solvents, such as chloroform, the drug and cationic lipid are mixed in solvents in which both are soluble and the solvent is then removed under vacuum. The lipid-drug residue then is dispersed in an appropriate aqueous solvent, e.g., sterile physiological saline. Optionally, the suspension is subjected to up to several freeze/thaw cycles. The suspension then is sonicated to reduce the coarseness of the dispersion or to reduce the particle size to 20 to 30 nm diameter. This will depend on whether a large or small particle size is most efficacious in the desired application. For some applications, it may be useful to generate extruded liposomes by forming the suspension through a filter with pores of 100 nm diameter or smaller. Additionally, it may be useful to include cholesterol or natural phospholipids in the mixture to generate lipid-drug aggregates.

The lipid vehicles of the present invention that carry a bioactive agent can be delivered in any suitable manner. For agents that are soluble in aqueous solution and insoluble in organic solvents, the lipid mixture to be used for the lipid dispersion or liposomes can be coated on the inside surface of a flask or tube by evaporating the solvent from a solution of the mixture. In general, the lipid mixture should be capable of forming vesicles having single or multiple lipid bilayer walls and encapsulating an aqueous core. The aqueous phase containing the dissolved agent (e.g., physiological saline solution) then can be added to the lipid, agitated to generate a suspension and then optionally frozen and thawed up to several times.

In particular embodiments, the lipid vehicles of the invention can be used with or without vanilloid (e.g., capsaicin) and/or botulinum toxin (e.g., botulinum toxin D), which then can be used alone or in combination with a chemotherapeutic agent, targeting antibody, or DNA construct designed for the treatment of bladder cancer. Specifically, liposomes or lipid vehicles comprising vanilloid and/or botulinum toxin can be used to prevent, treat or ameliorate pain or voiding dysfunction associated with bladder cancer. Lipid-based treatments for bladder cancer that employ chemotherapeutic agents (see, e.g., J. B. Bassett et al., 1986, J. Urol. 135(3):612-5; C. P. Dinney et al., 1995, J. Interferon Cytokine Res. 15(6):585-92; T. Tsuruta et al., 1997, J. Urol. 1997 157(5):1652-4; H Kiyokawa et al., 1999, J. Urol. 161(2):665-7), targeting antibodies (see, e.g., J. Morgan et al., 1994, Photochem. Photobiol. 60(5):486-96; A. Aicher et al., 1994, Urol. Res. 22(1):25-32) and DNA constructs (e.g., Y. Horiguchi et al., 2000, Gene Ther. 7(10):844-51; L. A. Larchian et al., 2000, Clin. Cancer Res. 6(7):2913-20; M. Cemazar et al., 2002, Cancer Gene Ther. 9(4):399-406) are known in the art.

In another embodiment, lipid vehicles of the present invention may be used with or without vanilloid (e.g., capsaicin) and/or botulinum toxin (e.g., botulinum toxin D), which then can be used alone or in combination with one or more antibacterial agents. Specifically, liposomes or lipid vehicles comprising vanilloid and/or botulinum toxin can be used to prevent, treat or ameliorate pain or voiding dysfunction associated with a urinary system infection. Lipid-based treatments for infection are generally known in the art, including those employing tetracycline and doxycycline (L. Sangare et al., 1999, J. Med. Microbiol. 48(7):689-93; L. Sangare et al., 1998, J. Antimicrob. Chemother. 42(6):831-4.); tobramycin (C. Beaulac et al., 1999, J. Drug Target. 7(1):33-41); gentamycin and ceftazidime (R. M. Schiffelers et al., 2001, Int. J. Pharm. 214(12):103-5; R. M. Schiffelers et al., 2001, J. Pharm. Exp. Ther. 298(1)369-75); anthracycline (N. Dos Santos et al., 2002, Biochem. Biophys. Acta 1561(2):188-201); ciprofloxacin (B. Wiechens et al., 1999, Ophthalmologica 213(2):120-8), and other anti-infectives.

To generate small liposomes, the suspension can be subjected to ultrasonic waves for a time necessary to reduce the liposomes to the desired average size. If large liposomes are desired, the suspension can be agitated by hand or on a vortex mixer until a uniform dispersion is obtained, i.e., until visually observable large particles are present. For lipid vehicles comprising a bioactive agent or drug, alone, the agent or drug in the aqueous phase is eliminated by dialysis or by passage through a gel-filtration chromatographic column (e.g., agarose) equilibrated with the aqueous phase containing all normal components except the agent or drug. The lipid mixture used can contain cholesterol or natural lipids in addition to the liposome compounds of the present invention. The liposome-drug aggregate then may be delivered in any suitable manner (see above).

The present invention includes, but is not limited to, the following embodiments: a method of treating pain in an organ in a mammalian subject which comprises administering to the subject a pharmaceutical composition comprising a lipid vehicle in an amount effective to treat the condition; the method of the preceding embodiment, wherein the lipid vehicle is a liposome; the method of any one of the preceding embodiments, wherein the organ is a genitourinary tract organ; the method of any one of the preceding embodiments, wherein the genitourinary tract organ is selected from the group consisting of bladder, kidney, urethra, ureter, prostate, penis, testes, seminiferous tubules, epididymis, vas deferens, seminal vesicles, bulbourethral glands, uterus, vagina and fallopian tubes; the method of any one of the preceding embodiments, wherein the organ is a gastrointestinal tract organ; the method of any one of the preceding embodiments, wherein the gastrointestinal tract organ is selected from the group consisting of esophagus, stomach, large intestine and small intestine; the method of any one of the preceding embodiments, wherein the pain is associated with a condition selected from the group consisting of infection, inflammation, irritation, cancer and spasticity; the method of any one of the preceding embodiments, wherein the lipid vehicle is administered using a method selected from the group consisting of intravesical instillation, intravenous, topical, nasal spray, pulmonary inhaler and oral administration; the method of any one of the preceding embodiments, wherein the lipid vehicle further comprises a vanilloid compound; the method of any one of the preceding embodiments, wherein the vanilloid is selected from the group consisting of capsaicin, resiniferatoxin and tinyatoxin; the method of any one of the preceding embodiments, wherein the lipid vehicle is a liposome; the method of any one of the preceding embodiments, wherein the organ is a genitourinary tract organ; the method of any one of the preceding embodiments, wherein the genitourinary tract organ is selected from the group consisting of a bladder, kidney, urethra, ureter, prostate, penis, testes, seminiferous tubules, epididymis, vas deferens, seminal vesicles, bulbourethral (Cowper) glands, uterus, vagina and fallopian tubes; the method of any one of the preceding embodiments, wherein the organ is a gastrointestinal tract organ; the method of any one of the preceding embodiments, wherein the gastrointestinal tract organ is selected from the group consisting of esophagus, stomach, large intestine and small intestine; the method of any one of the preceding embodiments, wherein the organ is a pulmonary system organ; the method of any one of the preceding embodiments, wherein the pulmonary system organ is selected from the group consisting of trachea, lungs, bronchi, bronchioles, alveoli, and cilia; the method of any one of the preceding embodiments, wherein the lipid vehicle is administered by a method selected from the group consisting of intravesical instillation, intravenous, topical, nasal spray, pulmonary inhaler and oral administration; the method of any one of the preceding embodiments, wherein the carrier, excipient or diluent comprises physiological saline.

The present invention includes, but is not limited to, the following embodiments: a method of treating involuntary muscle contraction in a mammalian subject which comprises administering to the subject a pharmaceutical composition comprising a lipid vehicle carrying botulinum toxin in an amount effective to treat the contraction; The method of the preceding embodiment, wherein the lipid vehicle is a liposome; the method of any one of the preceding embodiments, wherein the botulinum toxin is selected from the group consisting of botulinum toxins A through G; the method of any one of the preceding embodiments, wherein the involuntary muscle contraction affects a body part selected from the group consisting of the eye(s), lip(s), tongue, mouth, jaw, head, neck, face, arm, hand, finger, leg, trunk, vagina, cervix and bladder; the method of any one of the preceding embodiments, wherein the involuntary muscle contraction affects a sphincter selected from the group consisting of esophageal, cardiac, pyloric, ileocaecal, O'Beirne, anal, urethra and bladder neck sphincters; the method of any one of the preceding embodiments, wherein the involuntary muscle contraction is associated with a condition selected from the group consisting of tremors, hemifacial spasms, tics, strabismus, nystagmus, eyelid entropion, myokymia, bruxism, tardive dyskinetic syndrome, lateral rectus palsy, stuttering, painful rigidity, tension headache, back spasm, radiculopathy, spasticity, spastic bladder, urinary detrusor-sphincter dyssynergia, achalasia, anismus, vaginismus, segmental dystonia, idiopathic dystonia and secondary focal distonia; the method of any one of the preceding embodiments, wherein the involuntary muscle contraction is associated with a focal dystonia selected from the group consisting of blepharospasm, oromandiibular distonia, facial dystonia, lingual dystonia, cervical dystonia, torticollis, spasmodic dysphonia and task-specific dystonia; the method of any one of the preceding embodiments, wherein the lipid vehicle is administered by a method selected from the group consisting of intravesical instillation, intravenous, topical, nasal spray, pulmonary inhaler and oral administration; the method of any one of the preceding embodiments, wherein the carrier, excipient or diluent comprises physiological saline.

The present invention is more particularly described in the following examples, which are intended to be illustrative only, as numerous modifications and variations therein will be apparent to those skilled in the art.

EXAMPLES

The following Examples 1-4 describe investigations undertaken to determine liposomal properties with respect to charge and structure, i.e., the bioactive component(s) in egg phosphaditylcholine (PC), responsible for reducing bladder hyperactivity in a rat model of bladder injury. Previous studies have shown that the egg PCs used in the studies were only 60% pure. In particular, these investigations evaluated the effect of liposomes prepared from various natural and synthetic lipids, such as lipids having acyl chain length similar to natural lipids but varying in degree of saturation and charge on the headgroup, in the rat bladder injury model.

Example 1

The optimal lipid characteristics (e.g., head groups, length and degree of saturation) for making lipid vehicles of the present invention were determined, as well as the effect of lipid headgroup charge in reducing bladder hyperactivity Materials and Methods Bladder reflex activity in thirty-four (34) female Sprague-Dawley rats (200-250 g) was studied by cystometry performed under anesthesia with urethane (1.2 g/kg) administered by subcutaneous injection. Body temperature was maintained in the physiologic range using a heating lamp. A transurethral bladder catheter (PE-50) connected by a three-way stopcock to a pressure transducer and to a syringe pump was used to record intravesical pressure and to infuse solutions into the bladder. A control cystometrogram (CMG) was performed by slowly filling the bladder with saline at a rate of 0.04 ml/min to elicit repetitive voiding. The bladder contraction frequency of the reflex bladder contractions were recorded. After performing control CMGs with saline infusion for 3 hours, protamine sulfate (PS) (Sigma Chemical; 10 mg/ml) was infused at a rate of 0.04 ml/min for 1 hour to increase epithelial permeability followed by infusion of the irritant KCl (500 mM) for 1 hour. Subsequently, liposomes made from lipids of various compositions then were infused in the presence of a high concentration of KCl for 2 hours.

The effect of charge on the lipid headgroup in reducing bladder activity in three animal groups (n=5) was determined. Neutrally charged liposomes prepared with L-α-PC (a zwitterionic lipid egg PC) were compared against liposomes having either a positively or negatively charged polar headgroup, namely, 1,2-dioleoyl-3-trimethylammonium-propane (DOTAP) and 1-α-phosphatidylserine (POPS), respectively.

Liposomes were prepared as described by Kirby and Gregoriadis (Kirby, C. J. and Gregoriadia, G., "A simple procedure for preparing liposomes capable of high encapsulation efficiency under mild conditions," Liposome Technology, G. Gregnoriadis, Ed., C.R.C. Press, Inc., Boca Raton, Fla., 1984, Vol. 1, p. 20, 1984). Briefly, liposomes were constructed as a 2:1 molar ratio of L-α-phosphatidylcholine and cholesterol (Sigma Chemical Co., St. Louis, Mo.) to a final lipid concentration of 1-2 mg/ml in saline. Lipids in chloroform were dried down together in the proper ratio under nitrogen. The residues were reconstituted as liposomes in saline or 500 mM KCl by intense sonication. This lipid composition produced liposomes with no net charge.

Statistical analyses were performed using Student's t test for paired or unpaired data, where applicable. A P-value less than 0.05 was considered significant. All data were expressed as means±S.E. (standard error).

Results

As shown in FIG. 1, liposomes made from lipids with a phosphaditylchloine (PC) head group were able to suppress chemically induced bladder hyperactivity to a significantly greater extent ($p<0.01$) than liposomes made from lipids having a cationic or anionic charge, such as DOTAP and POPS, respectively. Specifically, L-α-PC was able to produce a three-fold higher (33±5.3%) reduction in bladder contraction frequency over its pretreatment control compared to DOTAP (10±0.09%) and POPS (5±0.02%).

Figure 2A:
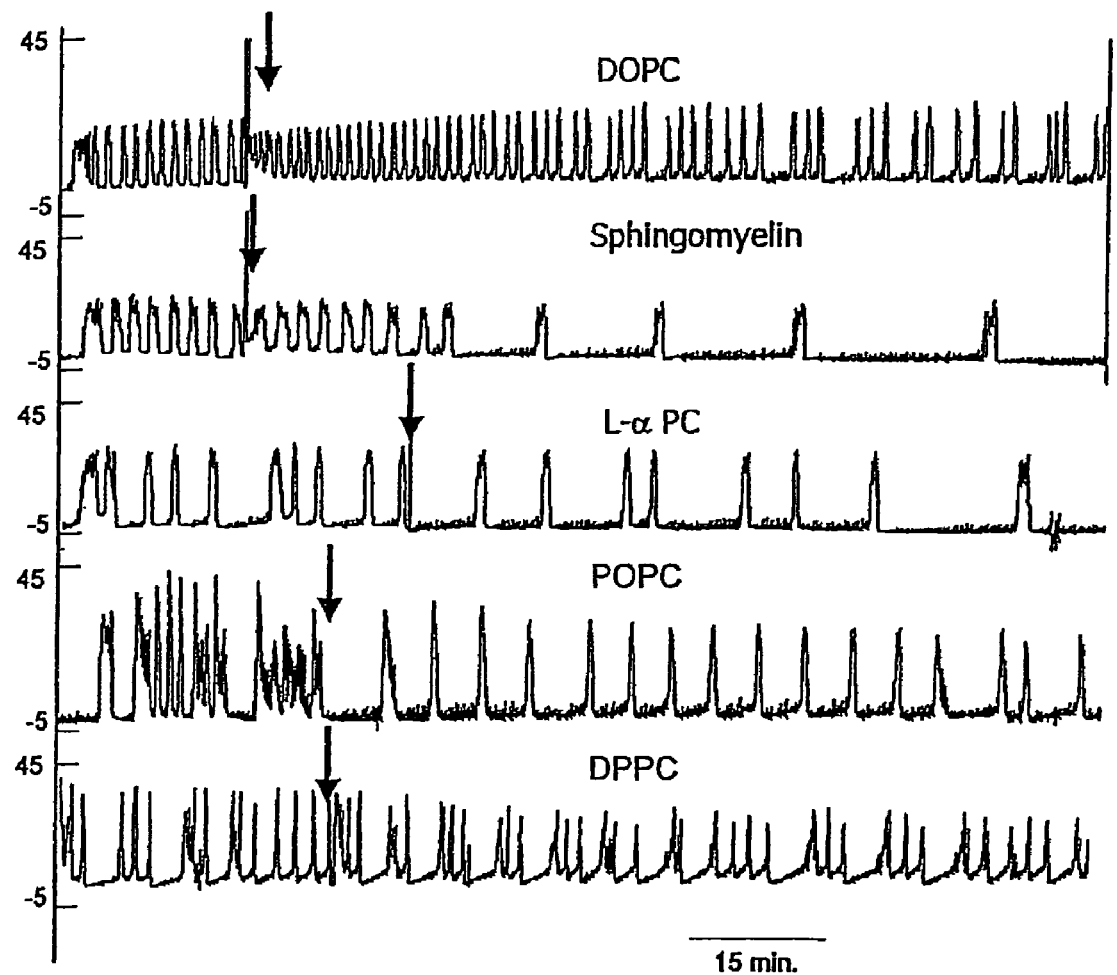
FIGS. 2A-2B shows the effect of various acyl chains in lipids having PC headgroup on suppression of bladder hyperactivity. (A): The lipids used were 1,2Dioleoyl sn-Glycero-3-Phosphocholine (DOPC); sphingomyelin; 1-Palmitoyl-2-Oleoyl-sn-Glycero-3-Phosphocholine (POPC); L-□-Phosphatidylcholine (PC) and 1,2-Dipalmitoyl-sn-Glycero-3-Phosphocholine (DPPC) The number of peaks per unit time were reduced significantly in the sphingomyelin treated bladder compared to other groups. (B): The structures of lipids are shown.
Figure 2B:
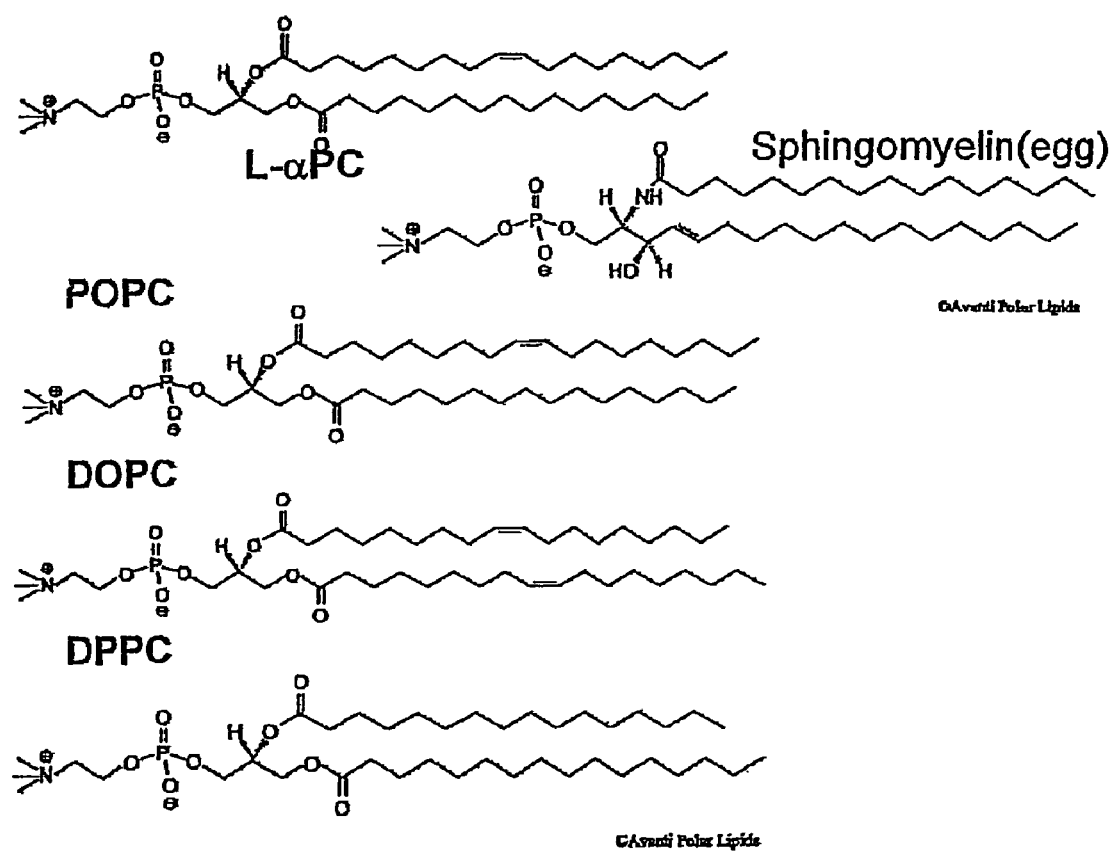

Sphingomyelin was found to be the best among the lipids with a PC head group in reducing bladder contraction frequency as compared to DOPC, 1-α-PC, POPC and DPPC (FIG. 2A). Optimal activity was found when only one of the linked acyl chains was unsaturated. All liposomes were prepared at the lipid concentration of 2 mg/ml in 500 mM KCl. The structures of the lipids are shown in FIG. 2B.

Example 2

This example demonstrates the effect of sphingomyelin liposomes in reducing bladder hyperactivity.

Material and Methods

Neutrally charged liposomes prepared with sphingomyelin were compared against liposomes prepared from dihydrosphingomyelin and two pure synthetic lipids: 1,2-distearoyl-sn-glycero-3-phosphocholine (DSPC) and 1,-oleoyl-2-stearoyl-sn-glycero-3-phosphocholine (OSPC).

The methodology of this investigation is the same as described above in Example 1 with the exception that the preparation of liposomes was modified from Example 1. Briefly, liposomes were constructed as a 2:1 molar ratio of sphingomyelin and cholesterol (Sigma Chemical Co., St. Louis, Mo.) to a final lipid concentration of 1-2 mg/ml in saline. Lipids in chloroform were dried down together in the proper ratio under nitrogen. The residues were reconstituted as liposomes in saline or 500 mM KCl by intense sonication. This lipid composition produced sphingomyelin liposomes with no net charge.

Results

As shown in FIG. 2, sphingomyelin liposomes were able to reduce the bladder hyperactivity in the presence of KCl significantly more than dihydrosphingomyelin, DSPC and OSPC, as evidenced from the decreased bladder contraction frequency following the start of liposome infusion. The black arrow marks the start of infusion of the liposomes in the presence of 500 mM KCl.

Example 3

This example demonstrates the effect of DSPC liposomes formulated with sphingomyelin or sphingomyelin metabolites on bladder hyperactivity.

Materials and Methods

Sphingomyelin devoid of its phosphorylcholine head group generates the molecule ceramide, a well known lipid second messenger which mediates a wide range of cellular responses to external stimuli, and also is used for the biosynthesis of sphingomyelin and glycosphingolipids. Because ceramide cannot form stable liposomes by itself, its effect on bladder hyperactivity was tested by including it at 1 mol % in an inert lipid, namely, 1,2-distearoyl-sn-glycero-3-phosphocholine (DSPC).

The methodology of this investigation is the same as described above in Example 1 with the exception that the preparation of liposomes was modified from Example 1. Briefly, liposomes were constructed as a 2:1 molar ratio of DSPC/sphingomyelin and cholesterol, DSPC/ceramide and cholesterol, DSPC/sphingosine and cholesterol or DSPC/sphingosine 1-phosphate and cholesterol, to a final lipid concentration of 1-2 mg/ml in saline. Lipids in chloroform were dried down together in the proper ratio under nitrogen. The residues were reconstituted as liposomes in saline or 500 mM KCl by intense sonication. This lipid composition produced liposomes with no net charge.

Results

Figure 3:
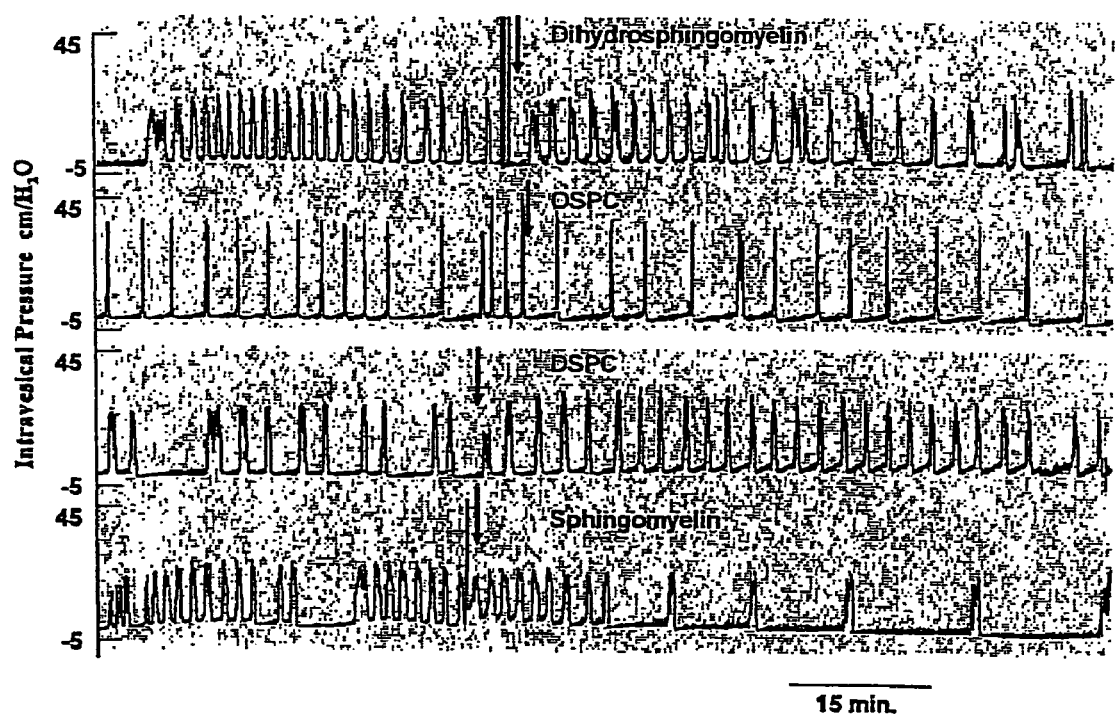
FIG. 3 is a CMG of liposomes prepared from sphingomyelin, dihydrosphingomyelin, and pure synthetic lipids having one acyl chain derived from stearic acid, namely, DSPC and OSPC.

As shown in FIG. 3, ceramide significantly increased the efficacy of DSPC in reducing bladder contraction frequency. Inclusion of 1 mol % of sphingosine, another sphingomyelin metabolite, into DSPC also had a similar effect. Inclusion of the sphingomyelin metabolite sphingosine 1-phosphate at 1 mol % into DSPC did not show a similar beneficial effect, but was equally effective as ceramide and sphingosine at reducing bladder contraction frequency when included in DSPC at higher mol percentages, such as 1-5 mol % (data not shown). Interestingly, inclusion of sphingomyelin into DSPC at 1 mol % did not increase the efficacy of the DSPC liposomes.

The results from this set of experiments indicate that metabolites of sphingomyelin (SPM), when included in pure synthetic liposomes, such as DSPC, at low concentrations of 1 mol %, are significantly more active than the parent compound itself in reducing bladder contraction frequency in rats.

Example 4

This example demonstrates the effect of liposomes formulated with cerebroside on bladder hyperactivity.

Materials and Methods

Figure 4:
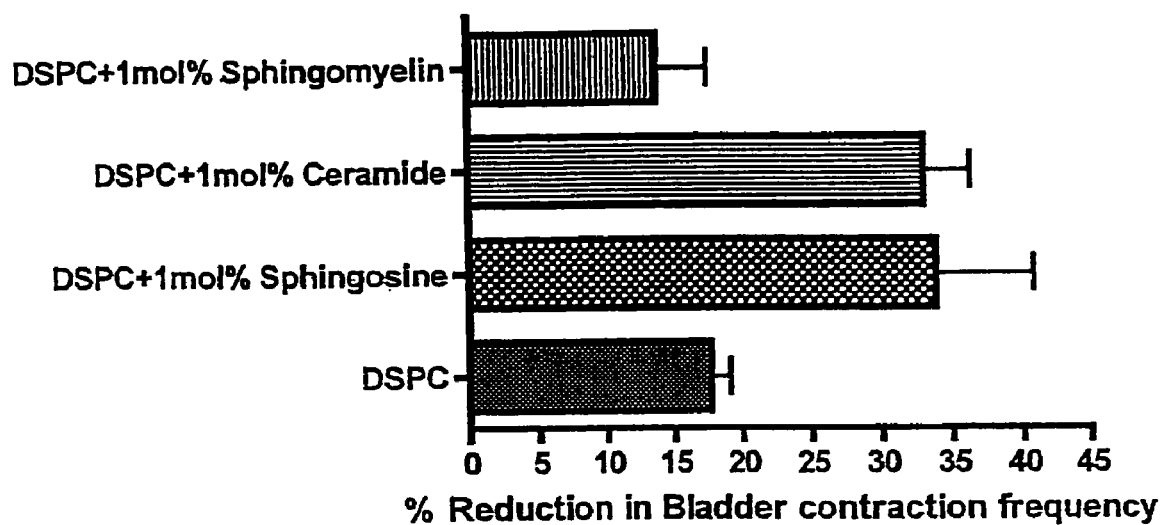
FIG. 4 is a bar graph showing the effect of adding sphingomyelin and sphingomyelin metabolites to DSPC liposomes on bladder hyperactivity.

Cerebroside is a sphingoglycolipid and is a precursor of ceramide. Cerebroside has a polar head consisting of a monosaccharide, such as glucose or galactose. FIG. 4 shows a cerebroside molecule having a β-galactose polar head.

The methodology of this investigation is the same as described above in Example 3 with the exception that liposomes were constructed as a 2:1 molar ratio of DSPC/cerebroside and cholesterol to a final lipid concentration of 1-2 mg/ml in saline. Lipids in chloroform were dried down together in the proper ratio under nitrogen. The residues were reconstituted as liposomes in saline or 500 mM KCl by intense sonication. This lipid composition produced liposomes with no net charge.

Results

Figure 5:
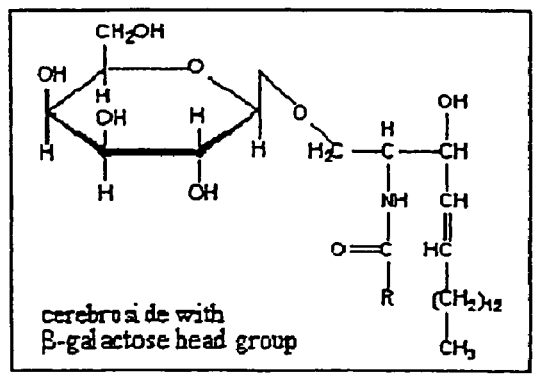
FIG. 5 shows the chemical structure of the sphingoglycolipid cerebroside, which is a precursor of ceramide.

As shown in FIG. 5, cerebroside significantly increased the efficacy of DSPC in reducing bladder contraction frequency. After the start of infusion of DSPC/cerebroside liposomes (shown by the black arrow in the tracing), the time interval between the peaks were increased, indicating a reduction in bladder contraction frequency.

Summary of Examples 1-4

The results from Examples 1-4 demonstrated that liposomes constituted with sphingomyelin or with liposomes constituted with sphingomyelin metabolites, such as ceramide, sphingosine, sphingosine 1-phosphate or cerebroside, significantly decreased bladder hyperactivity in a rat model compared to other liposomes, such as dihydrosphingomyelin, or liposomes devoid of sphingomyelin metabolites. Sphingomyelin is one of several lipids constituting the 13% of neutral lipids in impure egg PC. Not all of the lipids present in egg PC were effective in reducing bladder hyperactivity. In particular, one lipid, which is the ether ester analog of PC, 1-alkyl-2-acetoyl-sn-glycero-3-phosphocholine, platelet activating factor (PAF), when instilled alone or when included with DSPC liposomes at 1-5 mol % actually aggravated the bladder reflex activity.

Figure 6:
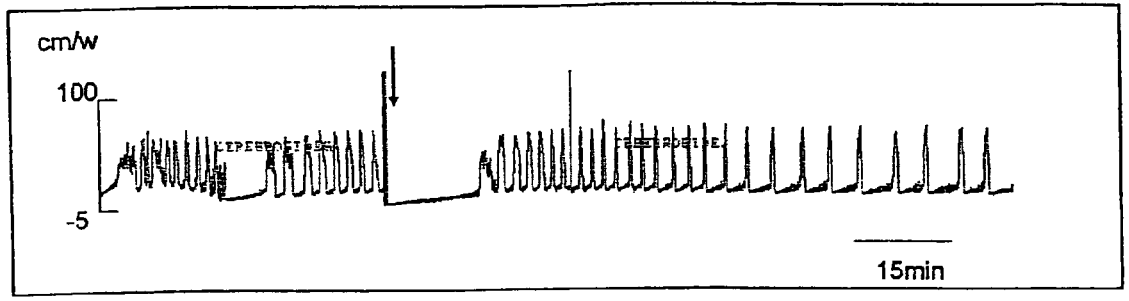
FIG. 6 is a CMG showing the effect of adding cerebroside, a sphingoglycolipid, to DSPC liposomes on bladder hyperactivity.

FIG. 6 depicts a proposed mechanism for the activity of sphingomyelin liposomes on bladder hyperactivity in the rat model. The reduction in bladder contraction frequency observed after instillation of sphingomyelin liposomes or its metabolites may be due to an anti-inflammatory effect of these compounds. Both ceramide and sphingosine are known negative effectors of protein kinase C (PKC), an intracellular enzyme known to possess anti-inflammatory effects. Additionally, it is believed that ceramide may reduce IL-2 production in Jurkat cells by inhibiting PKC-mediated activation of NF-κB.

Example 5

A hyperactive bladder model in Sprague-Dawley rats was established by exposure to acetic acid, or protamine sulfate (PS) in KCl solution. This was followed by instillation of liposomes (LP) in saline (in the case of the former) or LP/KCl. Continuous CMG changes were examined and results were compared with control (saline instillation), hyperactive bladder (acetic acid or PS/KCl) and treatment with LP.

Materials and Methods

Intravesical bladder pressure was recorded via a transurethral catheter in adult female Sprague-Dawley rats anesthetized with urethane (1.2 g/kg) administered by subcutaneous injection (sc). Some animals were pretreated with capsaicin (125 mg/kg, sc) four days prior to the experiments. Continuous CMGs were performed by slowly filling the bladder (0.04 ml/min) with solutions of various composition including saline, acetic acid (0.1%), KCL (500 mM), protamine sulfate (PS) (10 mg/ml), LP, PS/KCL, or LP/KCl. Parameters measured included intercontraction interval (ICI), amplitude of bladder contractions, compliance and micturition pressure threshold (PT).

Animal Preparation. Thirty-four female Sprague-Dawley rats (250-300 g) were used in this study. Animals were anesthetized with urethane (1.2 g/kg, sc). Body temperature was maintained in the physiological range using a heating lamp.

Cystometrogram (CMG). A transurethral bladder catheter (PE-50) was connected via a three-way stopcock to a pressure transducer and to a syringe pump. This was used to record intravesical pressure and to infuse solutions into the bladder. A control CMG was performed by slowly filling the bladder with saline (0.04 ml/min) to elicit repetitive voiding. The parameters recorded were amplitude, PT, compliance, and ICI of reflex bladder contractions. Measurements in each animal represented the average of 3 to 5 bladder contractions.

Figure 7:
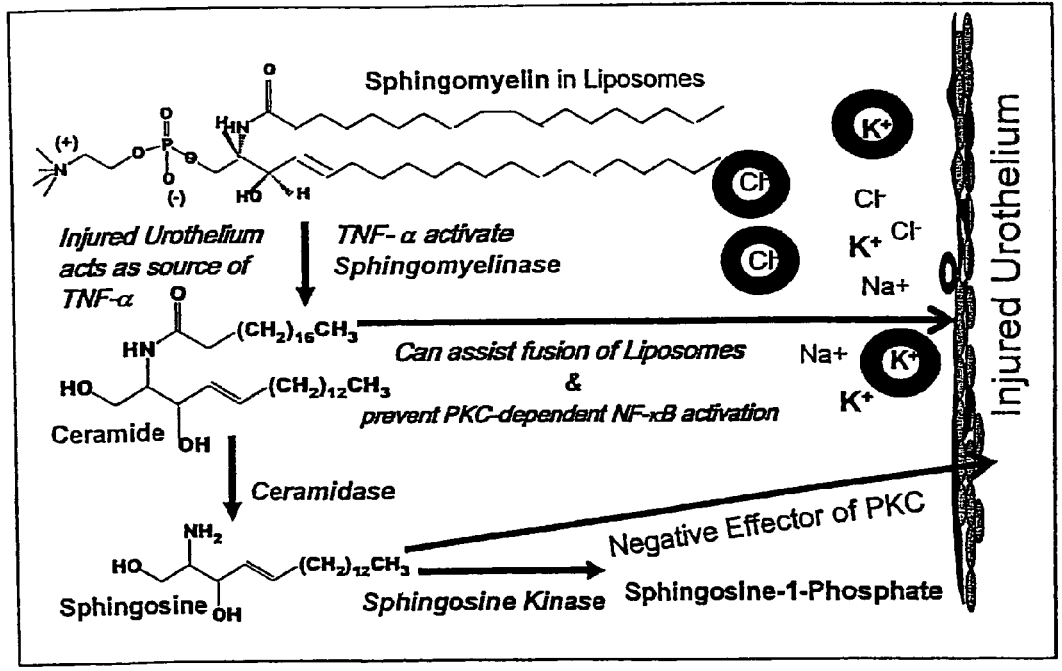
FIG. 7 illustrates a proposed mechanism for the activity of sphingomyelin liposomes based on rat experiments and literature reports.

Induction of a Hyperactive Bladder. After performing control CMGs with saline infusion, five intravesical infusion experiments were performed in parallel: (1) infusion of PS (Sigma Chemical Co. 10 mg/ml) for one hour (N=6) to increase epithelial permeability; (2) infusion of KCl (500 mM) for one hour, then infusion with PS/KCl for another one hour, followed by infusion of either KCl for two hours (N=6) or LP/KCl for two hours (N=6); (3) infusion of acetic acid (AA) (0.1%) for one hour, followed by infusion of saline (N=6) or LP (N=6) for two hours; (4) infusion of LP for one hour, followed by infusion of AA for one hour (N=6); and (5) infusion of AA (N=4) for two hours in animals subcutaneously injected with capsaicin (125 mg/kg in 10% ethanol, 10% TWEEN®80, 80% saline) four days before the experiment (C. L. Cheng et al., 1993, Am. J. Physiol. 265:R132-138). The experimental design is illustrated in FIG. 7. The KCl concentration used was within the range of concentrations present in normal rat urine (M. Ohnishi et al., 2001, Toxicol. Appl. Pharmacol. 174:122-129).

Preparation of Liposomes (LP). LP were prepared as described by Kirby and Gregoriadis (C. J. Kirby and G. Gregoriadia, 1984, "A simple procedure for preparing liposomes capable of high encapsulation efficiency under mild conditions," Liposome Technology; G. Gregnoriadis, Ed., C.R.C. Press, Inc., Boca Raton, Fla., Vol. 1, p. 20). Briefly, LP were constructed as a 2:1 molar ratio of L-α-phosphatidylcholine and cholesterol (Sigma Chemical Co., St. Louis, Mo.) to a final lipid concentration of 2 mg/ml in saline. Lipids in chloroform were dried down together in the proper ratio under nitrogen. The residues were reconstituted as LP in saline or 500 mM KCl by intense sonication. This lipid composition produced LP with no net charge.

Statistical Analyis. Statistical analyses were performed using Student's t test for paired or unpaired data, where applicable. A p-value less than 0.05 was considered significant. All data are expressed in Example 2 (below) as means±S.E.

Example 6

The results of the experiments described in Example 5 are presented herein below. In summary, intercontraction interval (ICI) was decreased after exposure to acetic acid (AA) (79.8% decrease) or PS/KCl (81% decrease). However, ICI was not changed by LP, PS or KCl alone. The decrease in ICI was partly reversed after infusion of LP (172.8% increase) or LP/KCl (63% increase), but was not significantly changed after saline or KCl administration. Pretreatment with capsaicin delayed the onset of the irritative effects of AA by approximately 30 to 60 min, but did not change the magnitude after two hours of infusion.

Figure 8:
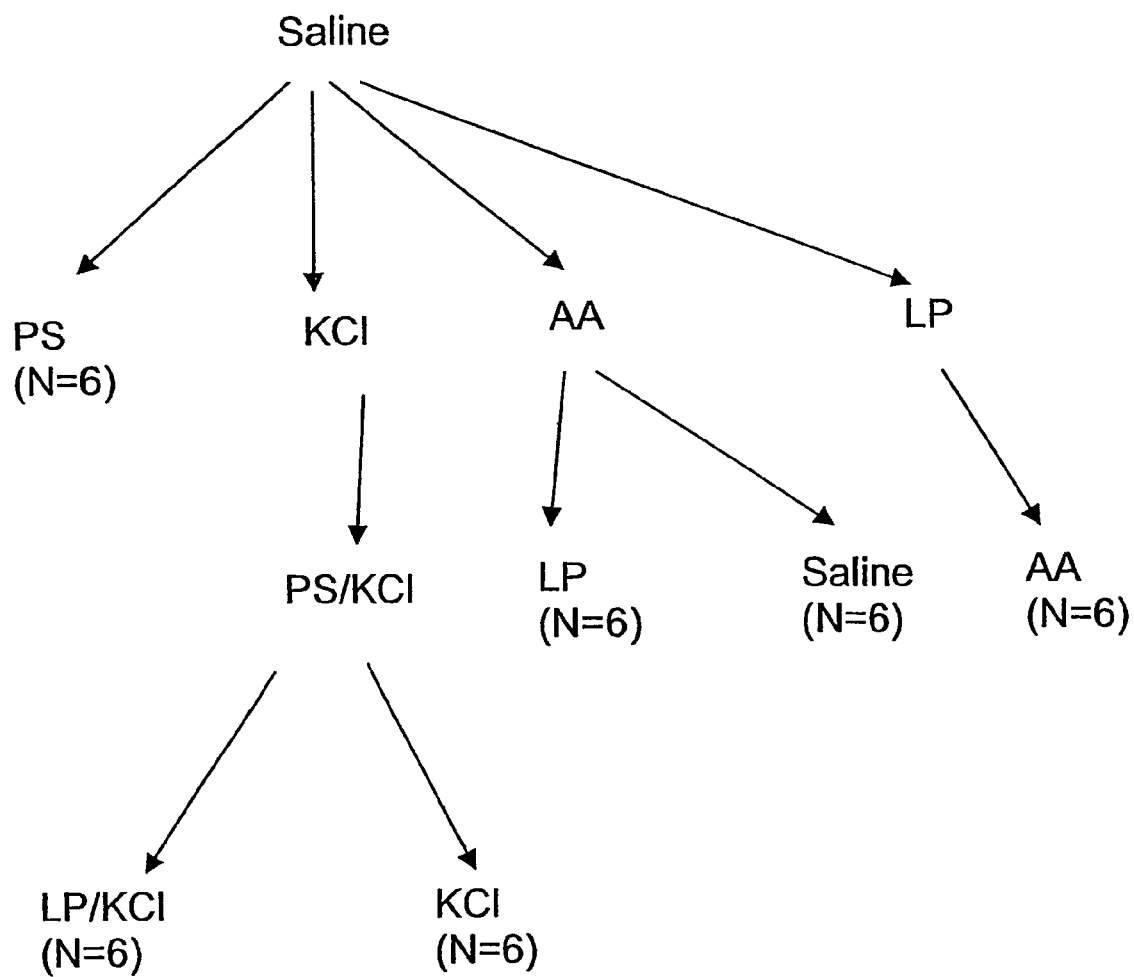
FIG. 8 shows the experimental design for the studies described in Examples 5-6 (below)

As shown in Tables 1A-1C, infusion of PS (10 mg/ml) or KCl (500 mM) alone did not significantly change the CMGs. However, infusion of PS/KCl provided an irritative effect after a delay of 30 to 40 min (FIGS. 8B, 8D). The ICI and compliance were significantly reduced by 79 to 83% (from 15.8±1.4 to 2.7±1.0 min or from 16.3±1.5 to 3.4±0.7 min) and 58 to 75% (from 0.284±0.028 to 0.070±0.019 ml/cm $H_2O$ or from 0.226±0.050 to 0.096±0.037 ml/cm $H_2O$) in two series of experiments.

Bladder contraction amplitude was significantly increased (23%) in one series (Table 1C), but not in the other series (Table 1B). However, taking the average of the two series, bladder contraction amplitude showed a significant increase (16%). PT was not significantly changed. When the infusion fluid was switched to LP/KCl after a delay of 10 to 20 min, the ICI was significantly increased (63%, from 2.7±1.0 to 4.4±1.2 min). Switching to KCl alone did not alter the ICI for periods as long as 120 min (FIGS. 8E, 8F; Tables 1B 1C). PT was significantly increased after shifting to LP/KCl or KCl infusion. Compliance was not significantly changed after shifting to LP/KCl infusion, but was further reduced (from 0.096±0.037 to 0.043±0.014 ml/cm $H_2O$) after shifting to KCl infusion.

TABLE 1A

Effects of saline and protamine sulfate (PS) on CMG parameters

| | ICI (min) | Compliance (ml/cm H$_2$O) | PT (cm H$_2$O) | Amplitude (cm H$_2$O) |
|---|---|---|---|---|
| Saline | 13.8 ± 3.1 | 0.197 ± 0.030 | 7.6 ± 0.7 | 23.5 ± 1.7 |
| PS (10 mg/ml) | 14.9 ± 1.7 | 0.210 ± 0.031 | 5.9 ± 0.9 | 27.5 ± 0.7 |

Parameters included intercontraction interval (ICI), compliance, pressure threshold (PT), and amplitude. No statistically significant differences were observed between saline and 1 hour of treatment with PS. Values are means ± S.E., N = 6.

TABLE 1B

Effects of saline, KCl, PS/KCl, and LP/KCl on CMG parameters

| | ICI (min) | Compliance (ml/cm H$_2$O) | PT (cm H$_2$O) | Amplitude (cm H$_2$O) |
|---|---|---|---|---|
| Saline | 15.6 ± 2.1 | 0.270 ± 0.020 | 7.3 ± 0.8 | 26.5 ± 1.1 |
| KCl | 15.8 ± 1.4 | 0.284 ± 0.028 | 8.2 ± 0.9 | 28.8 ± 1.2 |
| PS/KCl | 2.7 ± 1.0* | 0.070 ± 0.019* | 6.7 ± 0.7 | 31.2 ± 1.0 |
| LP/KCl | 4.4 ± 1.2* | 0.065 ± 0.029 | 10.3 ± 0.6* | 31.3 ± 2.8 |

Parameters included intercontraction interval (ICI), compliance, pressure threshold (PT), and amplitude. Values are means ± S.E., N = 6.
*P < 0.05, in comparison with pretreatment.

TABLE 1C

Effects of saline, KCl, PS/KCl, and KCl on CMG parameters

| | ICI (min) | Compliance (ml/cm H$_2$O) | PT (cm H$_2$O) | Amplitude (cm H$_2$O) |
|---|---|---|---|---|
| Saline | 18.0 ± 2.0 | 0.270 ± 0.022 | 6.3 ± 0.7 | 25.7 ± 1.6 |
| KCl | 16.3 ± 1.5 | 0.226 ± 0.050 | 6.8 ± 0.6 | 28.8 ± 2.2 |
| PS/KCl | 3.4 ± 0.7* | 0.096 ± 0.037* | 7.3 ± 0.4 | 35.3 ± 2.6* |
| KCl | 2.9 ± 0.5 | 0.043 ± 0.014* | 11.8 ± 1.6* | 33.0 ± 2.3 |

Parameters included intercontraction interval (ICI), compliance, pressure threshold (PT), and amplitude. Values are means ± S.E., N = 6.
*P < 0.05, in comparison with pretreatment.

Figure 9A:
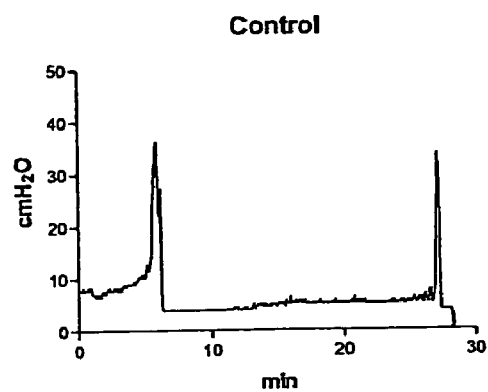
FIGS. 9A-9F shows CMG tracing results. Treatments included saline (control), protamine sulfate (PS) in potassium chloride (PS/KCl) and liposomes (LP) in potassium chloride (KCl) (LP/KCl) or KCl alone. PS/KCl elicited bladder hyperactivity. LP/KCl partly reversed the irritative effect of LP/KCl and this reversal was maintained after switching to KCl.
Figure 9B:
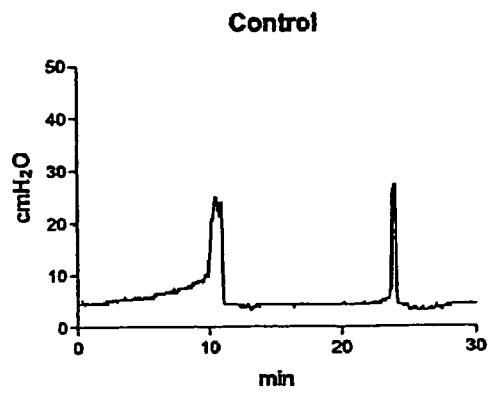
Figure 9C:
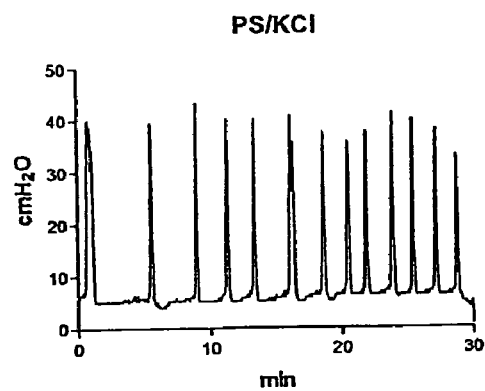
Figure 9D:
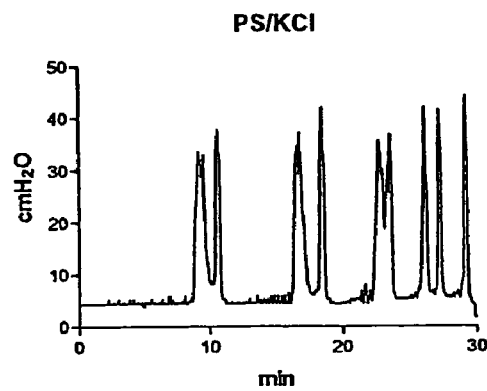
Figure 9E:
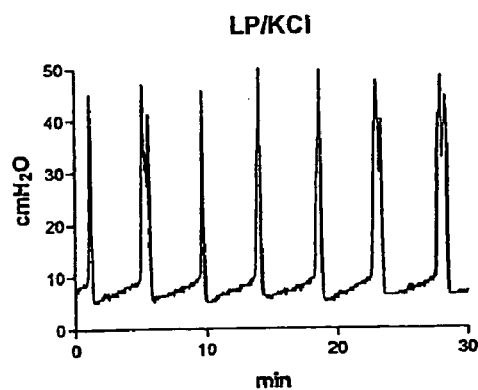
Figure 9F:
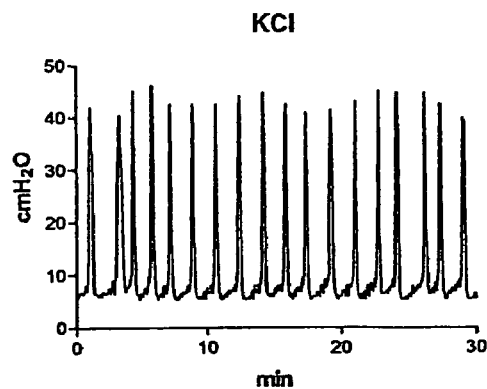
Figure 10A:
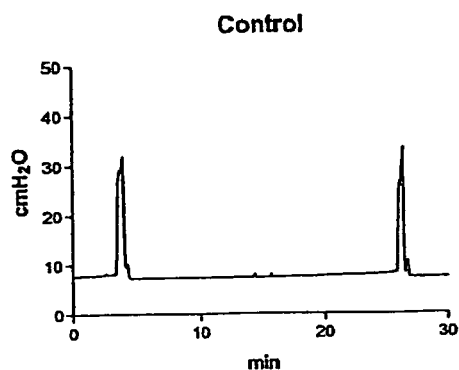
FIGS. 10A-10F shows CMG tracing results. Treatments included saline (control), acetic acid (AA) and liposomes (LP) or saline. AA elicited bladder hyperactivity. LP partly reversed the irritative effect of AA and this reversal was maintained after switching to saline.
Figure 10B:
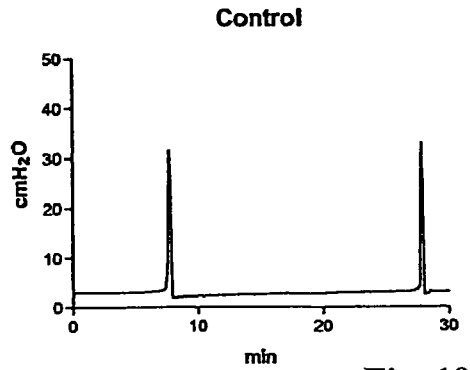
Figure 10C:
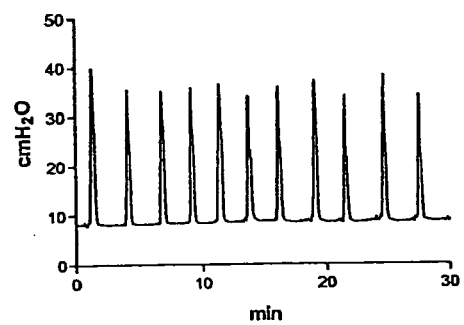
Figure 10D:
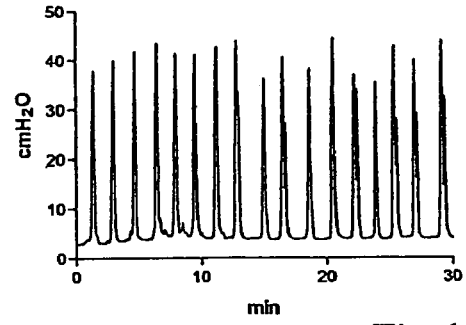
Figure 10E:
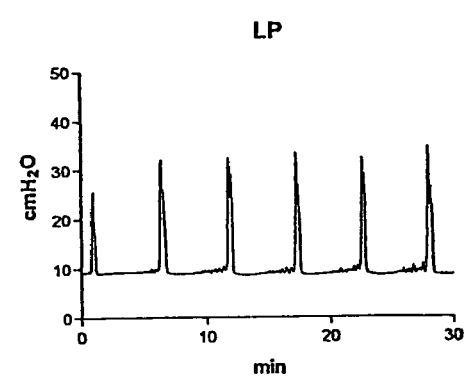
Figure 10F:
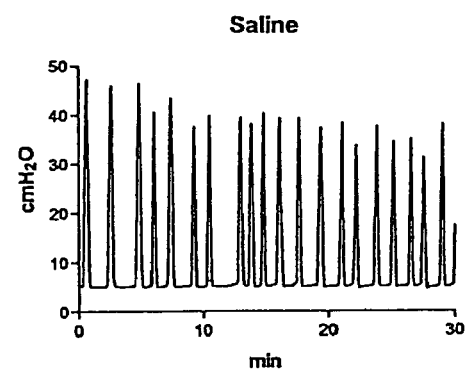
Figure 11A:
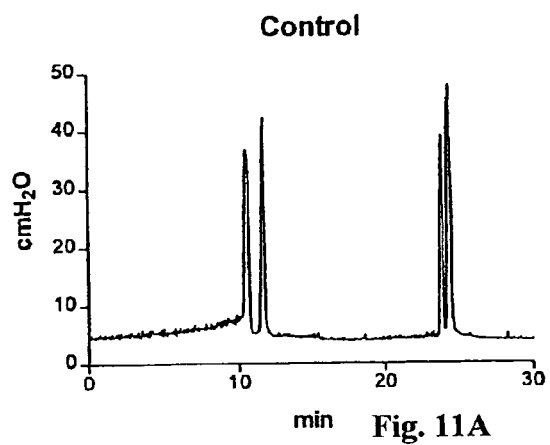
FIGS. 11A-11D shows CMG tracing results. Treatments included saline (control) and various concentrations of protamine sulfate (PS). High concentrations of PS induced bladder hyperactivity (decreased ICI), whereas low concentrations of PS produced no effect.
Figure 11B:
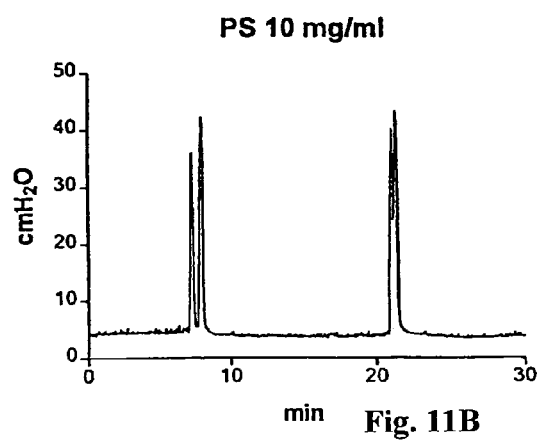
Figure 11C:
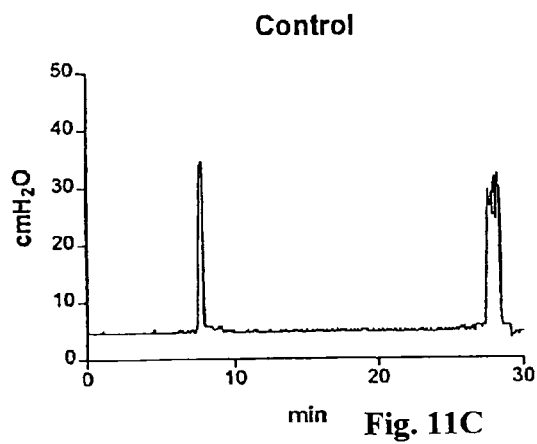
Figure 11D:
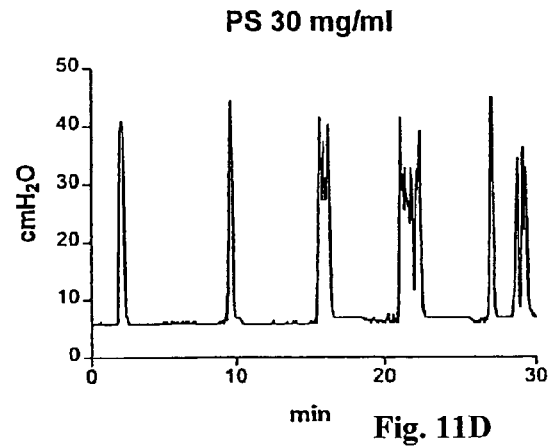

CMGs in AA Infusion Group. The irritative effect of AA was evident at about 20 to 30 min following infusion. ICI and compliance were significantly reduced by 75 84% (from 15.3±2.2 to 2.4±0.5 min or from 12.6±2.0 to 3.2±1.3 min) and 71-76% (from 0.296±0.040 to 0.071±0.016 ml/cm H$_2$O or from 0.275±0.048 to 0.079±0.026 ml/cm H$_2$O) in two series of experiments (FIGS. 9A-9F; Tables 2A-2B). Amplitude was less affected, showing a slight increase, and PT was not significantly changed. Upon subsequent infusion of LP, ICI and compliance were significantly increased (179%, from 2.4±0.5 to 6.7±1.5 min; and 38%, from 0.071±0.016 ml/cm H$_2$O to 0.114±0.020 ml/cm H$_2$O) after approximately 10 to 20 min (FIGS. 9E, 9F; Tables 2A-2B). This increase persisted for as long as 120 min after switching to infusion of saline. LP infusion alone for 1 hour did not change the micturition reflex in untreated animals (Table 2C); and the effect of an M infusion was not reduced by prior intravesical administration of LP.

TABLE 2A

Effects of saline, acetic acid (AA), and liposomes (LP) on CMG parameters

| | ICI (min) | Compliance (ml/cm H$_2$O) | PT (cm H$_2$O) | Amplitude (cm H$_2$O) |
|---|---|---|---|---|
| Saline | 15.3 ± 2.2 | 0.296 ± 0.040 | 6.6 ± 0.9 | 28.7 ± 1.7 |
| AA | 2.4 ± 0.5* | 0.071 ± 0.016* | 8.3 ± 0.9 | 36.8 ± 6.5 |
| LP | 6.7 ± 1.5* | 0.114 ± 0.020* | 10.2 ± 1.8 | 30.8 ± 6.5 |

Parameters included intercontraction interval (ICI), compliance, pressure threshold (PT), and amplitude. Values are means ± S.E., N = 6.
*P < 0.05, in comparison with pretreatment.

TABLE 2B

Effects of saline, AA, and saline on CMG parameters

| | ICI (min) | Compliance (ml/cm H$_2$O) | PT (cm H$_2$O) | Amplitude (cm H$_2$O) |
|---|---|---|---|---|
| Saline | 12.6 ± 2.0 | 0.275 ± 0.048 | 7.2 ± 1.0 | 28.2 ± 3.2 |
| AA | 2.9 ± 0.9* | 0.079 ± 0.026* | 9.1 ± 1.4 | 37.0 ± 7.0 |
| Saline | 3.2 ± 1.3 | 0.063 ± 0.011 | 8.6 ± 1.2 | 28.2 ± 7.0* |

Parameters included intercontraction interval (ICI), compliance, pressure threshold (PT), and amplitude. Values are means ± S.E., N = 6.
*P < 0.05, in comparison with pretreatment.

Table 2C

Effects of saline, LP, and AA on CMG parameters

| | ICI (min) | Compliance (ml/cm H$_2$O) | PT (cm H$_2$O) | Amplitude (cm H$_2$O) |
|---|---|---|---|---|
| Saline | 14.7 ± 3.0 | 0.254 ± 0.028 | 7.0 ± 0.8 | 29.8 ± 2.4 |
| LP | 16.0 ± 1.9 | 0.255 ± 0.023 | 6.7 ± 0.6 | 30.0 ± 2.3 |
| AA | 3.1 ± 0.8* | 0.071 ± 0.022* | 6.7 ± 0.7 | 38.0 ± 1.3* |

Parameters included intercontraction interval (ICI), compliance, pressure threshold (PT), and amplitude. Values are means ± S.E., N = 6.
*P < 0.05, in comparison with pretreatment.

In capsaicin pretreated animals, bladder hyperactivity evoked by AA was delayed for 0.5-1 hour. ICI and compliance were reduced in magnitude by 51% and 33% at 1 hour (from 21.0±2.4 to 10.2±3.0 min and from 0.226±0.033 to 0.152±0.028 ml/cm H$_2$O), but at 2 hours was similar to the effect in untreated animals (78% decrease to 4.6±1.2 min and 64% decrease to 0.082±0.024 ml/cm H$_2$O) (Table 3). In addition, the reduction of ICI (10.2±3.0 min) after 1 hour application of AA in capsaicin-pretreated rats (Table 3) was significantly longer (p<0.05) compared to the ICI (2.9±0.9 min) measured within 1 hour of application in untreated rats (Table 2B). This indicated that C-fiber desensitization by capsaicin pretreatment suppressed AA-induced bladder hyperactivity and delayed the onset of AA-induced hyperactivity.

TABLE

Effects of saline and AA on CMG parameters in capsaicin pretreated rats

| | ICI (min) | Compliance (ml/cm H$_2$O) | PT (cm H$_2$O) | Amplitude (cm H$_2$O) |
|---|---|---|---|---|
| Saline | 21.0 ± 2.4 | 0.226 ± 0.033 | 7.9 ± 0.8 | 21.1 ± 1.3 |
| AA (1 hr) | 10.2 ± 3.0* | 0.152 ± 0.028* | 6.7 ± 0.2 | 20.9 ± 2.5 |
| AA (2 hr) | 4.6 ± 1.2 | 0.082 ± 0.024* | 6.7 ± 0.7 | 23.6 ± 5.7 |

Parameters included intercontraction interval (ICI), compliance, pressure threshold (PT), and amplitude. Values are means ± S. E., N = 4.
*P < 0.05, in comparison with pretreatment.

Summary of Examples 5-6

The sum of the results from Examples 5-6 indicated that (1) intravesical administration of LP suppressed chemically-induced bladder hyperactivity; and (2) low-dose PS treatment in the presence of physiological KCl produced sustained bladder hyperactivity. The administration of LP thereby represents new treatment approaches for a damaged or leaky urothelium, while low-dose PS provides a pharmacological model for examination of drugs that might restore the leaky urothelium. Additionally, it is of interest that AA-induced hyperactivity also was reduced by LP. This indicated that chemically-induced irritation/inflammation of the bladder mucosa, as well as direct breakdown of the urothelial barrier by PS, could both be reversed by LP. Without wishing to be bound by theory, it is possible that the effects of LP, as observed above, were mediated by the production of a film on the urothelium that reduced the influx of irritants. It also is possible that LP stabilized neuronal membranes and reduced the hyper-excitability of afferent receptors.

From these experiments, it became clear that bladder afferents played a key role in the mechanism of action of AA in the induction of bladder hyperactivity. Previous experiments have shown that infusion of AA into the bladder stimulates nociceptive afferent fibers, induces an inflammatory reaction and evokes a hyperactive bladder (Y. Yu and W. C. de Groat, 1998, Brain Res. 807:11 18; L. A. Birder and W. C. de Groat, 1992, J. Neurosci. 12:4878 4889; K. B. Thor and M. A. Muhlhauser, 1999, Am. J. Physiol. 277:R1002 1012). The stimulation of silent C-fibers has been implicated to play a central role in the pathogenesis of some hyperactive bladders, whereas A-δ afferents usually are thought to be primarily responsible for triggering normal voiding function (Y. Yu and W. C. de Groat, 1998, Brain Res. 807:11 18 13; C. L. Cheng et al., 1993, Am. J. Physiol. 265:R132 138; K. B. Thor and M. A. Muhlhauser, 1999, Am. J. Physiol. 277:R1002 1012). However, as shown above, capsaicin pretreatments at a dose known to desensitize C-fiber bladder afferents delayed and reduced the effect of intravesical AA. This suggested that sensitization of myelinated A-δ afferents also may play a role in bladder hyperactivity induced by AA. The concentration of AA used in these experiments was 0.1%, which could dissolve the GAG layer, damage the urothelial barrier and facilitate deeper penetration of irritant (M. Leppilahti et al., 1999, Urol. Res. 27:272-276). AA also could produce bladder hyperactivity through the VR1 receptors or proton sensitive channels (J. M. Welch et al., 2000, Proc. Natl. Acad. Sci. USA 97(25):13889-13894).

The prevailing theories for the pathogenesis of IC describe a leaky and dysfunctional urothelium that allows transepithelial migration of irritants, such as potassium, into the deep layers of bladder wall. There, the irritants depolarize afferent nerves and induce abnormal sensations as well as frequent voiding (C. L. Parsons et al., 1991, J. Urol. 145:732-735; C. L. Parsons et al., 1994, Br. J. Urol. 73:504 507; G. Hohlbrugger, 1999, Br. J. Urol. 83(suppl. 2):22-28; J. I. Bade et al., 1997, Br. J. Urol. 79:168-171). PS, which increases epithelial permeability (K. B. Thor and M. A. Muhlhauser, 1999, Am. J. Physiol. 277:R1002-1012), was used in the above experiments to increase the penetration of KCl through the urothelial barrier and induce a similar activation of afferent neurons. Prior to PS treatment, the same concentration of KCl did not alter voiding function. Additionally, PS alone did not elicit bladder hyperactivity. Thus, it seems reasonable to assume that PS was not acting as a primary bladder irritant, and that under normal conditions KCl in the bladder lumen would not alter the excitability of afferent nerves in the bladder wall. However, combined exposure to these agents (see above) mimicked the condition observed in IC patients.

The use of PS/KCl, as described above, resulted in a decrease in ICI and compliance, an increase in bladder contraction amplitude and no change in PT. High concentration of potassium has been used as a provocative test for IC patients (C. L. Parsons et al., 1998, J. Urol. 159:1862-1867). A previous study has shown that a high concentration of potassium triggers C-afferent fibers and causes further release of neurotransmitters or neuromodulators (J. Morrison et al., 1999, Scand. J. Urol. Nephrol. suppl 201:73-75). Subsequently, potassium induces the depolarization of detrusor muscle and provokes muscle contraction or tissue damage (G. Hohlbrugger, 1999, Br. J. Urol. 83(suppl. 2):22-28; C. L. Parsons et al., 1998, J. Urol. 159:1862-1867). The acute exposure of high concentration of potassium to the detrusor causes a decrease in bladder compliance and capacity (P. C. Stein et al., 1996, J. Urol. 155:1133-1138). In agreement with this, the experiments described above showed that ICI and compliance were decreased, but PT was not changed. However, it is known that high concentrations of potassium can irritate the urethra and cause high outlet resistance (G. Hohlbrugger, 1999, Br. J. Urol. 83(suppl. 2):22-28). Consistent with this, bladder contraction amplitude was elevated in the combination of our two series shown above.

The surface GAG layer has been proposed as a protective barrier that coats the transitional cell surface (J. I. Bade et al., 1997, J. Urol. 79:168-171; G. Hohlbrugger, 1995, J. Urol. 154:6 15; C. L. Parsons et al., 1980, Science 208:605-607). A GAG layer defect has been suggested in a subset of IC patients (C. L. Parsons et al., 1991, J. Urol. 145:732-735; C. L. Parsons et al., 1994, Br. J. Urol. 73:504-507). Liposomes (LP) are comprised of phospholipids in a system of concentric closed membranes and are used as a carrier for drugs or DNA constructs (K. Reimer et al., 1997, Dermatology 195 (suppl. 2):93-99; M. Nishikawa et al., 2001, Human Gene Therapy 12:861-870; G. Gregoriadis, 1976, New Eng. J. Med. 295:704-710). LP-based compositions provide a high-moisture film for wounds and mediate wound healing without chronic inflammatory-reaction in the neodermal layer (K. Reimer et al., 1997, Dermatology 195(suppl. 2):93-99; M. Schafer-Korting et al., 1989, J. Am. Acad. Dermatol. 21:1271 1275). Other investigators have suggested that LP interact with cells by stable absorption, endocytosis, lipid transfer and fusion (R. B. Egerdie et al., J. Urol. 142:390 398). As demonstrated herein, administration of LP to the wounded urothelium can be used as a novel method for treating patients with hyperactive bladder, IC or other urinary system disorders.

Example 7

An animal model for acute hyperactive bladder in rats was developed using intravesical infusion of PS, an agent used to break down urothelial barrier function and physiological concentrations of KCl.

Materials and Methods

Continuous CMGs were performed in urethane-anesthetized female rats. The bladder was filled (0.04 ml/min) with normal saline followed by intravesical infusion for a 60 minute period with a test solution comprising either KCl (100 or 500 mM) or PS (10 or 30 mg/ml). Following this, 10 mg/ml PS treated animals were infused intravesically with 100, 300 or 500 mM KCl. Some animals were pretreated with capsaicin (125 mg/ml, sc) four days before the experiments.

Animal Preparation. The study was performed on 40 female Sprague-Dawley rats weighing 250-300 gm. Animals were anesthetized with 1.2 gm/kg urethane injected subcutaneously. Body temperature was maintained in the physiological range using a heating lamp.

Cystometrogram (CMG). PE-50 tubing (Clay-Adams, Parsippany, N.J.) was inserted into the bladder through the urethra and connected via a three-way stopcock to a pressure transducer and to a syringe pump. This was used for recording intravesical pressure and for infusing solutions into the bladder. A control CMG was performed by slowly filling the bladder with saline (0.04 ml/min) to elicit repetitive voiding. The amplitude, PT, compliance and intercontraction interval (ICI) of reflex bladder contractions were recorded. Pressure threshold (PT) represents the pressure that induces the initial bladder contraction. PT often has been used as a parameter corresponding to afferent nerve activity for the induction of reflex bladder contractions. Measurements in each animal represented the average of 3 to 5 bladder contractions.

After performing control CMGs with saline infusion, three intravesical infusion experiments were performed in parallel: (1) infusion of KCl (100 or 500 mM in saline) for one hour (N=4 in each group); (2) infusion of PS (Sigma Chemical Co.; 30 mg/ml in saline) for one hour (N=6); and (3) infusion of PS (10 mg/ml) for one hour, followed by 100, 300 or 500 mM KCl for one hour (N=6, in each subgroup). In four animals, capsaicin dissolved in a vehicle containing 10% ethanol, 10% TWEEN®80 and 80% physiological saline, at a concentration of 20 mg/ml was given subcutaneously in divided doses on 2 consecutive days. The doses included 25 and 50 mg/kg at a 12-hour interval on the first day and 50 mg/kg on the second day, as previously described (C. L. Cheng et al., 1993, Am. J. Physiol. 265:R132-138). All injections were performed under halothane anesthesia. Four days after the last dosage of capsaicin, the animals were anesthetized and treated with intravesical administration of PS (10 mg/ml) for 1 hour followed by KCl (500 mM) infusion.

Suppression of Micturition Reflex. To evaluate the direct effects of potassium on detrusor muscle, micturition reflex was blocked in 4 animals by either intravenous hexamethonium injection (25 mg/kg) (N=2) or transection of bilateral pelvic nerves (N=2).

Statistical Analysis. Statistical analyses were performed using Student's t test for paired or unpaired data, as applicable, with p<0.05 considered significant. Quantitative data are expressed in Example 8 (below) as means plus or minus standard error.

Example 8

The results of the experiments described in Example 7 are presented herein below. In summary, the intravesical administration of high concentrations of PS (30 mg/ml) produced irritative effects with decreases in intercontraction interval (ICI decreased by 80.6%). This was not observed with administration of KCl (100 or 500 mM) or a low concentration of PS (10 mg/ml). Following infusion of a low concentration of PS, infusion of 300 or 500 mM KCl produced irritative effects (ICI decreased by 76.9 or 82.9%, respectively). The onset of irritation occurred more rapidly following 500 mM KCl (10 to 15 min) than with 300 mM KCl (20 to 30 min). Capsaicin pretreatment delayed the onset (approximate 60 min) and reduced the magnitude (ICI decreased by 35.5%) of irritative effects.

CMGs in Various Infusion Group. As shown in Table 4, the CMG parameters during infusion of 100 mM or 500 mM KCl alone were not significantly different from those during saline administration. These results indicated that the bladder barrier function was not affected by control conditions. During a one hour period of instillation with 10 mg/ml PS, there was no significant change in comparison with saline administration (FIGS. 10A-10D; Table 5). These results indicated that low-dose PS was not by itself a bladder irritant. However, instillation of 30 mg/ml PS into the bladder resulted in an irritative effect (ICI decreased by 80.6%, compliance decreased by 63.6% and PT increased by 36.8%) after a delay of 40 to 45 min (FIGS. 10A-10D; Table 5).

TABLE 4

Effects of 100 mM and 500 mM KCl on CMG parameters

| | Saline (control; N = 4) | Post 100 mM KCl | Saline (control; N = 4) | Post 500 mM KCl |
|---|---|---|---|---|
| PT (cm H$_2$O) | 7.2 ± 0.5 | 5.9 ± 0.5 | 7.3 ± 0.8 | 8.2 ± 0.9 |
| Amplitude (cm H$_2$O) | 25.5 ± 1.4 | 28.2 ± 0.5 | 26.5 ± 1.1 | 28.8 ± 1.2 |
| Compliance (ml/cm H$_2$O) | 0.206 ± 0.013 | 0.205 ± 0.032 | 0.268 ± 0.013 | 0.237 ± 0.023 |
| ICI (min) | 13.9 ± 2.4 | 13.8 ± 2.0 | 15.6 ± 2.1 | 15.8 ± 2.4 |

Parameters included volume pressure threshold (PT), amplitude, compliance, and intercontraction interval (ICI). No statistically significant differences were observed between 100 and 500 mM KCl treatment (N = 4 in each group). Values are means ± S.E.

TABLE 5

Effects of 10 and 30 mg/ml PS on CMG parameters

| | Saline (control; N = 18) | Post 10 mg/ml PS | Saline (control; N = 6) | Post 30 mg/ml PS |
|---|---|---|---|---|
| PT (cm H$_2$O) | 4.2 ± 0.8 | 3.4 ± 0.9 | 5.7 ± 0.6 | 7.8 ± 1.1* |
| Amplitude (cm H$_2$O) | 24.1 ± 2.4 | 25.3 ± 2.0 | 27.7 ± 0.8 | 28.3 ± 3.1 |
| Compliance (ml/cm H$_2$O) | 0.169 ± 0.012 | 0.176 ± 0.013 | 0.228 ± 0.024 | 0.083 ± 0.022* |
| ICI (min) | 16.8 ± 0.9 | 17.8 ± 0.7 | 13.9 ± 2.1 | 2.7 ± 0.7* |

N = 4 in each group. Parameters included volume pressure threshold (PT), amplitude, compliance, and intercontraction interval (ICI). Values are means ± S.E.
*P < 0.05, in comparison with control.

Effect of KCl following low concentrations of PS (10 mg/ml) infusion, as shown in FIGS. 11A-11F and Table 6, CMGs performed with 300 or 500 mM KCl infusion significantly changed the ICI (76.9 or 82.9% decrease), compliance (60 or 63.4% decrease) and contraction amplitude (23.7 or 21.4% increase). However, the PT was not significantly altered. The effect mediated by 300 mM KCl occurred after a delay of 20 to 30 min, whereas the effect mediated by 500 mM KCl occurred after a delay of about 10 to 15 min. This implied that higher concentrations of KCl yielded faster penetration. One hour of infusion of 100 mM KCl did not produce significant changes in the CMG parameters.

Summary of Examples 7-8

In summary, the results from Examples 7-8 demonstrated that: (1) low dose PS (10 mg/ml) was not a bladder irritant, but a noncytotoxic affront to urothelial barrier function; and (2) the use of "physiological" normal saline, versus more appropriately physiological 300 or 500 mM KCl (M. Ohnishi et al., 2001, Toxicol. Appl. Pharmacol. 174:122-129; J. Morrison et al., 1999, Scand. J. Urol. Nephrol. suppl 201:73-75) for cystometry affected the function of the lower urinary tract in animal models of hyperactive bladder. It has been postulated that a critical component of IC is a leaky urothelium (C. L. Parsons et al., 1991, J. Urol. 145:732-735; C. L. Parsons et al.,

TABLE 6

Effects of 100, 300 and 500 mM KCl on CMG following 10 mg/ml PS

| | Saline (control; N = 6) | Post 100 mM KCl | Saline (control; N = 6) | Post 300 mM KCl | Saline (control; N = 6) | Post 500 mM KCl |
|---|---|---|---|---|---|---|
| PT (cm $H_2O$) | 3.1 ± 1.2 | 3.0 ± 1.3 | 2.9 ± 0.6 | 3.3 ± 0.9 | 4.0 ± 0.9 | 5.4 ± 1.0 |
| Amplitude (cm $H_2O$) | 26.8 ± 3.7 | 28.2 ± 3.7 | 25.3 ± 0.9 | 31.3 ± 0.7* | 24.3 ± 2.1 | 29.5 ± 3.4* |
| Compliance (ml/cm $H_2O$) | 0.161 ± 0.022 | 0.157 ± 0.022 | 0.165 ± 0.027 | 0.066 ± 0.012* | 0.205 ± 0.018 | 0.075 ± 0.009* |
| ICI (min) | 17.2 ± 1.3 | 18.8 ± 2.1 | 17.4 ± 2.0 | 5.2 ± 1.7* | 18.8 ± 1.7 | 3.2 ± 1.3* |

N = 6 in each group. Parameters included volume pressure threshold (PT), amplitude, and intercontraction interval (ICI). Statistically significant differences were observed between control and 300/500 mM KCl treatment. Values are means ± S.E.
*P < 0.05, in comparison with control.

CMGs in Animals Pretreated with Capsaicin. In capsaicin pretreated animals, hyperactive bladder from the sequential infusion of PS (10 mg/ml) and KCl (500 mM) was delayed by about 1 hour. Additionally, the changes in ICI and compliance were reduced by 36 and 55% after 2 hours of infusion (ICI decreased from 20.3±1.2 to 13.1±2.8 min; compliance decreased from 0.224 to 0.100 ml/cm $H_2O$; Table 7). After sequential infusion of PS (10 mg/ml) and KCl (500 mM) in capsaicin-pretreated rats (Table 7), the ICI (13.1±2.8 min) was significantly longer (p<0.05) than the ICI (3.2±1.3 min) following intravesical application of PS (10 mg/ml) and KCl (500 mM) in untreated rats (Table 6). This indicated that C-fiber desensitization by capsaicin pretreatment suppressed PS/KCl-induced bladder hyperactivity.

1994, Br. J. Urol. 73:504-507; S. Keay et al., 1999, J. Urol. 162:1487-1489). A compromised urothelial barrier is believed to result in an influx of highly concentrated, noxious substances that are normally passed through the urinary tract without reabsorption (G. Hohlbrugger, 1999, Br. J. Urol. 83:22-28; C. L. Parsons et al., 1998, J. Urol. 159:1862-1867). Where the urothelial barrier is broken down, these substances can cross back into the bladder, where they stimulate activity of resident C-fiber afferents. This transmits pain sensations and causes sensory symptoms (C. L. Parsons et al., 1998, J. Urol. 159:1862-1867). According to one theory, the influx of concentrated potassium from the urine to the submucosal region depolarizes bladder wall sensory afferents and initiates hyperactive bladder (G. Hohlbrugger, 1999, Br. J. Urol. 83:22-28; C. L. Parsons et al., 1998, J. Urol. 159:1862-1867).

TABLE 7

Effects of KCl (500 mM) on CMG following one hour infusion of PS (10 mg/ml) in capsaicin pretreated animals

| | Saline (control; N = 4) | KCl (1 hr) | KCl (2 hr) |
|---|---|---|---|
| PT (cm $H_2O$) | 8.4 ± 0.9 | 5.8 ± 0.5 | 7.6 ± 1.7 |
| Amplitude (cm $H_2O$) | 18.3 ± 1.5 | 20.3 ± 0.3 | 16.0 ± 1.7 |
| Compliance (ml/cm $H_2O$) | 0.244 ± 0.007 | 0.218 ± 0.013 | 0.100 ± 0.016* |
| ICI (min) | 20.3 ± 1.2 | 21.3 ± 2.8 | 13.1 ± 2.8* |

N = 4 in each group. Parameters included volume pressure threshold (PT), amplitude, compliance, and intercontraction interval (ICI). Values are means ± S.E.
*P < 0.05, in comparison with control.

Figure 12A:
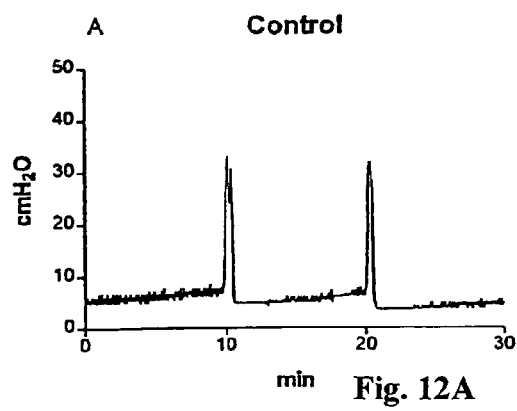
FIGS. 12A-12F shows CMG tracing results. Treatments included saline (control) and various concentrations of KCl following one hour of PS (10 mg/ml). High concentrations of KCl induced bladder hyperactivity (decrease ICI), whereas low concentrations of KCl had no effect.
Figure 12B:
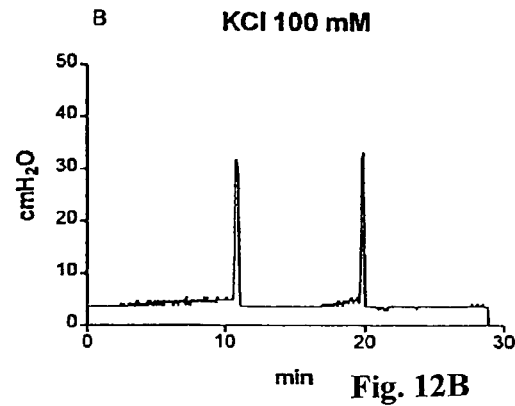
Figure 12C:
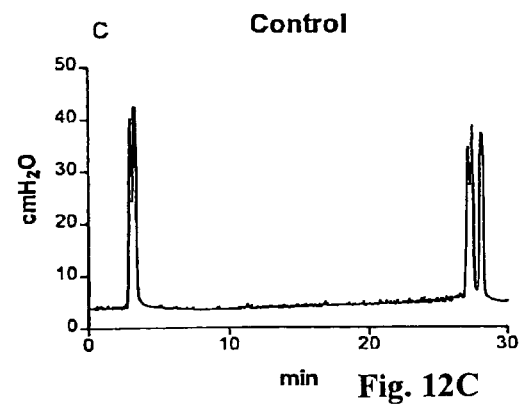
Figure 12D:
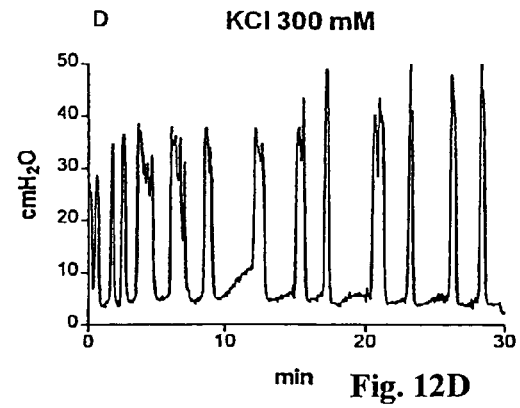
Figure 12E:
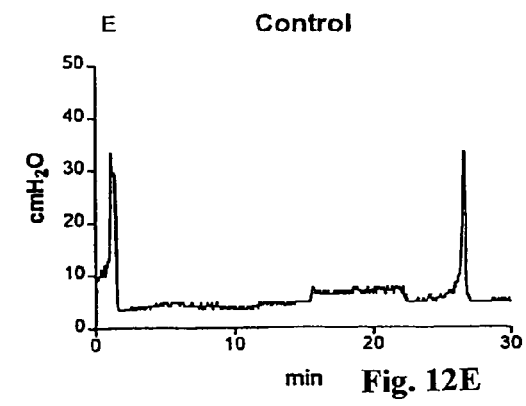
Figure 12F:
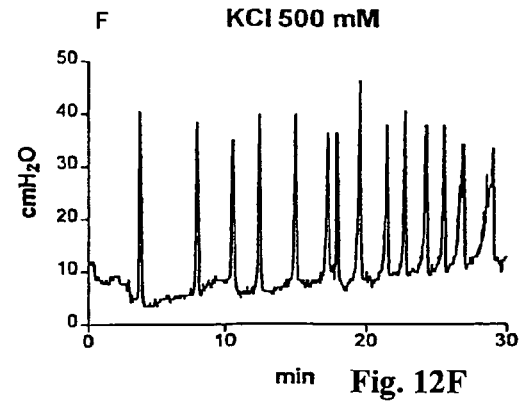

CMGs in Micturition Reflex Suppressed Animals. As shown in FIGS. 12A-12B, infusion of normal saline did not induce micturition reflex. This indicated that micturition reflex was blocked by hexamethonium injection or pelvic nerve transection. Infusion of KCl (500 mM) following PS (10 mg/ml) instillation decreased compliance by 55.9% (from 0.093±0.026 to 0.041±0.011 ml/cm $H_2O$). This indicated that potassium affected the direct stimulation of the detrusor muscle and caused the decrease in compliance.

The penetration of high concentrations of potassium through a leaky urothelium also is known to directly stimulate detrusor muscle and contribute to the decrease in bladder compliance (G. Hohlbrugger, 1999, Br. J. Urol. 83:22-28; G. Hohlbrugger, 1995, J. Urol. 154:6-15). The methods described herein block the micturition reflex by an autonomic ganglion blockade (hexamethonium) or a pelvic nerve transection, but decreases are still observed in the compliance after intravesical infusion of KCl following PS treatment.

This provides evidence of the stimulation of detrusor by high concentration of potassium. As shown herein, ICI was decreased, but PT was not changed. High concentration of potassium has been known to irritate the bladder neck and cause high outlet resistance (G. Hohlbrugger, 1999, Br. J. Urol. 83:22-28). Consistent with this, the bladder contraction amplitude was elevated in some of the results shown above.

The use of PS has been well established as a model for bladder injury. Previous experiments showed distension of the bladder for 45 min with 1 ml of 10 mg/ml PS (P. C. Stein et al., 1996, J. Urol. 155:1133-1138). It is known that prolonged over-distension of the bladder alters the properties of the bladder wall (S. Keay et al., 1999, J. Urol. 162:1487-1489; G. Hohlbrugger, 1995, J. Urol. 154:6-15). This may enhance the cytodestructive effects of PS and result in immediate urothelial sloughing (P. C. Stein et al., 1996, J. Urol. 155: 1133-1138). However, in the open CMG method described herein, one hour exposure of urothelium to the same concentration of PS did not cause obvious changes in CMG. Yet, urothelial barrier function was compromised and resulted in influx of high concentrations of potassium and bladder stimulation. Prior to PS treatment, the same concentration of potassium did not induce a hyperactive bladder. These data support the idea that abnormal epithelial permeability with an addition of high concentration of potassium in the urine is a key component to induce the symptoms of bladder hypersensitivity. It is hypothesized that without mechanical destruction of urothelium, prolonged exposure of PS might still lead to a subtle change but breakdown the barrier function. This model might elucidate the mechanism involved in the potassium test for the diagnosis of IC (C. L. Parsons et al., 1998, J. Urol. 159:1862-1867).

Other investigators have reported that intravesical instillation of 150 mM KCl through a pair of bladder dome catheters at a rate of 0.250 ml/min to a maximal pressure of 30 mm Hg can excite the afferent activity in hypogastric nerves, but is rarely detected in pelvic nerves (N. G. Moss et al., 1997, Am. J. Physiol. 272:R695-703). In these experiments, the average bladder volume used was 1.5 ml. This is 2 to 3 fold of normal bladder capacity in the rats and can result in over-distension of the bladder (N. G. Moss et al., 1997, Am. J. Physiol. 272:R695 703; M. Leppilahti et al., 1999, Urol. Res. 27:272-276; Y. C. Chuang et al., 2001, J. Urol. 165:975-979). Additionally, previous experiments showed the reduction of bladder capacity after a period of delay in a closed CMG method with intravesical isotonic KCl treatment (G. Hohlbrugger and P. Lentsch, 1985, Eur. Urol. 11:127-130). These effects were enhanced by pretreatment with 50% DMSO (G. Hohlbrugger and P. Lentsch, 1985, Eur. Urol. 11:127-130). However, the experiments described above showed that continuous infusion of KCl (500 mM) for 1 hour without pretreatment with PS did not induce significant bladder irritation. It is possible that altering the urothelium properties by either over-distension or DMSO installation could increase the bladder permeability and induce afferent firing and hyperactive bladder by KCl administration.

In conclusion, the use of 300 or 500 mM KCl for cystometry, versus physiological saline, affects the function of the lower urinary tract in animal models of hyperactive bladder. Accordingly, pharmaceutical compositions for the treatment of urinary system conditions preferably include excipients, diluents or carriers comprising physiological saline, as described in detail herein.

Example 9

Figure 13A:
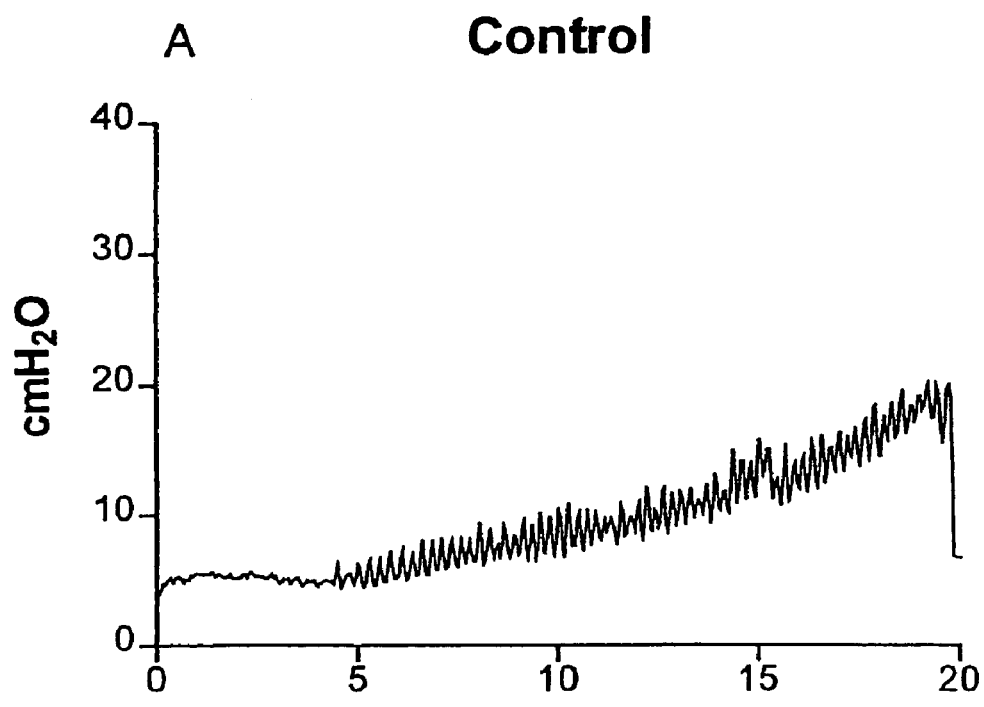
FIGS. 13A-13B shows. CMG tracing results. Treatments included saline (control) and KCl (500 mM) infusion following PS (10 mg/ml) infusion in micturition reflex suppressed animals. KCl stimulated the detrusor muscle and decreased bladder compliance.
Figure 13B:
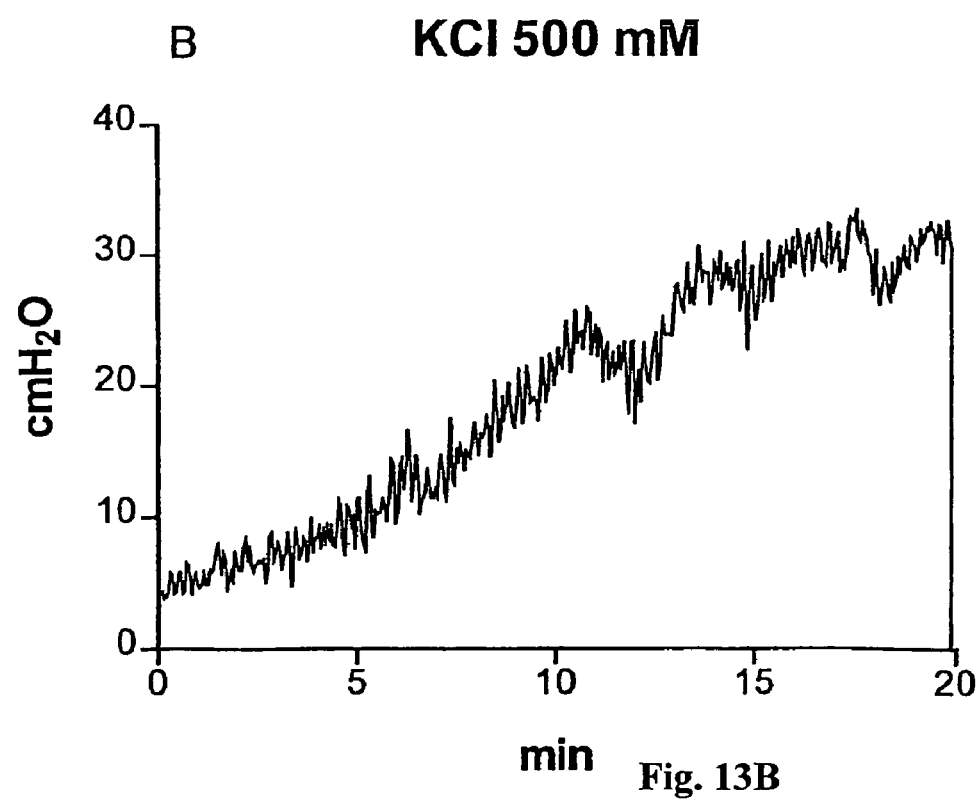
Figure 14:
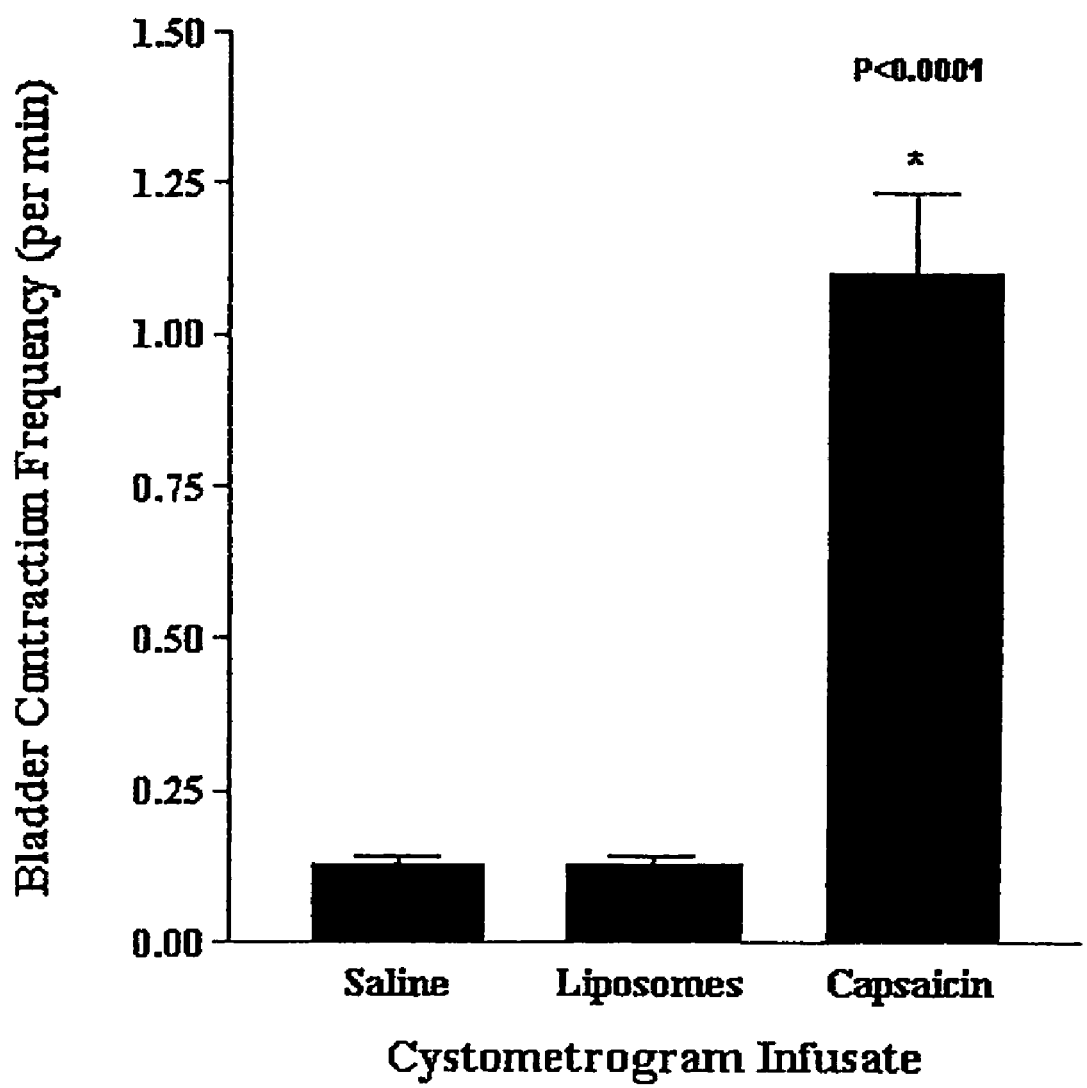
FIG. 14 shows the efficacy of liposomal delivery of capsaicin utilizing bladder contraction frequency as a bioassay of the irritative effects of the vanilloid. Column 1: saline; Column 2: liposomes; Column 3: liposomes plus capsaicin. Inclusion of capsaicin into the liposomal preparation allowed for effective capsaicin delivery. The addition of saline or liposomes produced no change in bladder contraction frequency. The combination of liposome and capsaicin produced a significant increase in bladder contraction frequency.

Intravesical vanilloid therapy has been used to treat detrusor hyperreflexia in spinal cord injury (SCI) and multiple sclerosis (MS) patients. Capsaicin (CAP) treatment requires high concentrations of ethanol (30% or greater) to achieve an effective dose. This level of ethanol is tissue toxic, and may, by itself, cause hemorrhagic cystitis. The lipoidal phase of liposomes (LP), concentric phospholipid bilayers, may provide an attractive alternative to high concentrations of ethanol. In an attempt to address this possibility, liposomal delivery of CAP was tested in urethane anesthetized rats.
Materials and Methods Open transurethral cystometry (0.04 ml/min) was performed under urethane anesthesia (1.2 g/kg) in 15 female S-D rats (250 300 g). Following a two-hour control period of saline infusion, the infusate was switched to either LP with 1 mM CAP (LP/CAP), or LP alone for 30 minutes followed by LP/CAP. The efficacy of CAP delivery was determined by the onset time of initial evidence of bladder irritation and subsequent desensitization and bladder contraction frequency. LP were constructed as described in Example 5, above. Briefly, a 2:1 molar ratio of phosphatidylcholine and cholesterol was dried down from chloroform solvent under nitrogen, with or without CAP. The resultant residue was brought into a saline suspension at 2 mg/ml total lipid by intense sonication.
Results LP alone had no effect on bladder contraction frequency (0.13±0.02 vs. 0.13±0.01) bladder contractions/min for control and LP, respectively (FIG. 13). However, LP/CAP resulted in a dramatic increase in bladder contraction frequency (1.11±0.08 bladder contractions/min, p<0.0001) within minutes of beginning the infusion (FIG. 13). Bladder contraction frequency subsequently slowed and finally halted by 124±24 minutes.
Conclusions LP are capable of highly effective delivery of at least one hydrophobic drug, CAP, as evidenced by a dramatic increase in bladder contraction frequency and subsequent desensitization. Moreover, LP alone had no effect on the micturition reflex in the un-irritated state. In combination with other experiments that have demonstrated a protective effect of LP, this suggested that the LP vehicle may partially protect against the compromise of urothelial barrier function due to the neuro-inflammatory response caused by irritants, such as CAP. This experiment indicates that LP could be used for other drugs, such as antibiotics and cancer treatments. Description of the experiments in this example can also be found in Y. C. Chuang et al., 100th Annual Meeting American Urological Association (AUA), Abstract; 2002, J. Urol. 167: 41A, which are hereby incorporated herein by reference.

Example 10

The effects of botulinum toxin (Btx) and liposome injections on autonomic (bladder) innervation of the lower urinary tract were investigated as follows.
Materials and Methods Liposomes were prepared as described in Example 5. Female S-D rats (250) were anesthetized with urethane (1.2 g/kg). Animals received intravesical liposomes plus instillation of Btx D (5.7 ng/gm body weight; Sigma, St Louis, Mo.). Control animals received no injections. All animals received tracheotomies and treated animals were artificially respired. Transvesical catheters were inserted and 6 hr after Btx injection, the bladder was harvested for strip studies.

For contractility experiments, bladder strips (20-30 g) were mounted in a double-jacketed organ bath at 36° C. in oxygenated Krebs solution. Electrical field stimulation was delivered through platinum electrodes positioned at the top and bottom using trains of 100 shocks at 20 Hz with maximal voltage every 100 sec. Strip fatigue was tested by trains applied every 20 sec. Fatigue amplitude and area, as well as recovery amplitude and area, were calculated as percent of the control value and compared between groups.

Results

Mean in vitro recovery amplitude of liposomes plus Btx was 68% that of the control value. It was concluded that liposomes carrying Btx significantly decreased bladder contractility.

The contents of all patents, patent applications, published articles, books, reference manuals, texts and abstracts cited herein are hereby incorporated by reference in their entirety to more fully describe the state of the art to which the present invention pertains.

It will be appreciated by those skilled in the art, that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

The invention claimed is:

1. A method of treating a bladder disorder selected from the group consisting of interstitial cystitis, urinary detrusor-sphincter dyssynergia, spastic neurogenic bladder, hyperactive bladder, bladder pain, bladder inflammation, and voiding dysfunction in animals or humans in need thereof, comprising administering to the animal or human by filling the bladder by intravesical instillation a therapeutically effective amount of an aqueous suspension of liposomes having entrapped therein a therapeutically effective amount of a botulinum toxin for the treatment of the bladder disorder.

2. The method according to claim 1, wherein the therapeutically effective amount of the botulinum toxin ranges from a dosage of about 0.1 mg to about 20 mg per kilogram body weight of the animal or human.

3. The method according to claim 1, wherein the therapeutically effective amount of the botulinum toxin ranges from a dosage of about 0.5 mg to about 10 mg per kilogram body weight of the animal or human.

4. The method according to claim 1, wherein the therapeutically effective amount of the botulinum toxin ranges from a dosage of about 1.0 mg to about 5.0 mg per kilogram body weight of the animal or human.

5. The method according to claim 1, wherein the liposomes are formulated from lipids selected from the group consisting of phospholipids, glycolipids, sphingolipids, sphingophospholipids, and sphingoglycolipds.

6. The method according to claim 5, wherein the lipids are selected from the group consisting of phosphatidylcholine, phosphatidylethanolamine, phosphatidylserine, phosphatidylinositol, phosphatidylglycerol, cardiolipin, glycolipids, sphingomyelin, sphingosine 1-phosphate, ceramide galactopyranoside, gangliosides, cerebroside, cholesterol, 1,2-distearoyl-sn-glycero-3-phosphocholine, 1,2-dioleoylphosphatidylcholine and combinations thereof.

7. The method according to claim 6, wherein the lipids are sphingomyelin.

8. The method according to claim 1, wherein the voiding dysfunction is incontinence.

9. The method of claim 1, wherein the botulinum toxin is selected from botulinum toxin A, botulinum toxin B, botulinum toxin C, botulinum toxin D, botulinum toxin E, botulinum toxin F and botulinum toxin G.

* * * * *

UNITED STATES PATENT AND TRADEMARK OFFICE
CERTIFICATE OF CORRECTION

| | | |
|---|---|---|
| PATENT NO. | : 8,110,217 B2 | Page 1 of 1 |
| APPLICATION NO. | : 11/546025 | |
| DATED | : February 7, 2012 | |
| INVENTOR(S) | : Michael B. Chancellor et al. | |

It is certified that error appears in the above-identified patent and that said Letters Patent is hereby corrected as shown below:

Column 1, line 20, insert

--STATEMENT REGARDING FEDERALLY SPONSORED RESEARCH
AND DEVELOPMENT

This invention was made with government support under Grant Number DK006885, awarded by the National Institutes of Health. The government has certain rights in the invention.--.

Signed and Sealed this
Fourth Day of December, 2012

David J. Kappos
*Director of the United States Patent and Trademark Office*

UNITED STATES PATENT AND TRADEMARK OFFICE
CERTIFICATE OF CORRECTION

PATENT NO.        : 8,110,217 B2                            Page 1 of 2
APPLICATION NO.   : 11/546025
DATED             : February 7, 2012
INVENTOR(S)       : Michael B. Chancellor et al.

It is certified that error appears in the above-identified patent and that said Letters Patent is hereby corrected as shown below:

Title page, column 1, Item (60), replace paragraph 1 under the title "Related U.S. Application Data" with the following paragraph: --Continuation-in-part of application No. 11/438,912, filed on May 22, 2006, now abandoned, which is a division of application No. 10/218,797, filed on Aug. 13, 2002, now Pat. No. 7,063,860.--.

Title page, column 1, Item (60), replace paragraph 2 under the title "Related U.S. Application Data" with the following paragraph: --Provisional application No. 60/725,402, filed on Oct. 11, 2005, provisional application No. 60/311,868, filed on Aug. 13, 2001.--.

In the Specification

Column 1, lines 8-19, replace the paragraph under the title "Cross-Reference to Related Applications" with the following paragraph: --This application claims the benefit of U.S. Provisional Application No. 60/725,402, filed Oct. 11, 2005. This application is also a Continuation-in-Part of U.S. application Ser. No. 11/438,912, filed May 22, 2006, now abandoned, which is a Division of U.S. Ser. No. 10/218,797, filed August 13, 2002, now U.S. Pat. No. 7,063,860, which claims the benefit of U.S. Provisional Application No. 60/311,868 filed Aug. 13, 2001, all of which are incorporated herein by reference.--.

Column 7, line 40, replace "(500 mM);" with --(500 mM).--.
Column 7, line 45, replace "L-☐-Phosphatidylcholine" with --L-α-Phosphatidylcholine--.
Column 7, line 47, replace "(DPPC) The" with --(DPPC). The--.
Column 7, line 54, replace "OSPC;" with --OSPC.--.
Column 7, line 57, replace "hyperactivity;" with --hyperactivity.--.
Column 7, line 59, replace "ceramide;" with --ceramide.--.
Column 7, line 62, replace "activity; and" with --activity.--.
Column 7, line 67, replace "(below);" with --(below).--.
Column 8, line 11, replace "respectively;" with --respectively.--.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,110,217 B2

Column 8, line 21, replace "respectively;" with --respectively.--.
Column 8, line 44, replace "shows. CMG" with --shows CMG--.
Column 22, line 45, replace "elements included" with --elements are included--.
Column 25, line 55, replace "multilamillar" with --multilamellar--.
Column 34, line 30, replace "hyperactivity" with --hyperactivity.--.
Column 35, line 10, replace "phosphaditylchloine" with --phosphatidylcholine--.
Column 36, line 56, replace "interval" with --intervals--.
Column 39, line 51, replace "75 84%" with --75-84%--.
Column 47, line 31, replace "breakdown" with --break down--.

In the Claims

Claim 5, column 50, line 16, replace "sphingoglycolipds" with --sphingoglycolipids--.